United States Patent
Brynda et al.

(10) Patent No.: US 9,290,529 B2
(45) Date of Patent: Mar. 22, 2016

(54) CARBONIC ANHYDRASE INHIBITORS AND METHOD OF THEIR PRODUCTION

(71) Applicants: USTAV ORGANICKE CHEMIE A BIOCHEMIE AKADEMIE VED CESKE REPUBLIKY, v.v.i., Prague (CZ); USTAV MOLEKULARNI GENETIKY AKADEMIE VED CESKE REPUBLIKY, v.v.i., Prague (CZ); USTAV ANORGANICKE CHEMIE AKADEMIE VED CESKE REPUBLIKY, v.v.i., Husinec-Rez (CZ); UNIVERZITA PALACKEHO V OLOMOUCI, Olomouc (CZ)

(72) Inventors: Jiri Brynda, Prague (CZ); Petr Cigler, Prague (CZ); Bohumir Gruner, Brandysek (CZ); Pavlina Maloy Rezacova, Velvary (CZ); Pavel Mader, Prague (CZ); Vaclav Sicha, Prague (CZ); Mario Bakardjiev, Prague (CZ); Josef Holub, Prague (CZ); Petr Dzubak, Brodek u Prerova (CZ); Marian Hajduch, Moravsky Beraun (CZ)

(73) Assignees: USTAV ORGANICKE CHEMIE A BIOCHEMIE AKADEMIE VED CESKE REPUBLIKY, V.V.I., Prague (CZ); USTAV MOLEKULARNI GENETIKY AKADEMIE VED CESKE REPUBLIKY, V.V.I., Prague (CZ); USTAV ANORGANICKE CHEMIE AKADEMIE VED CESKE REPUBLIKY, V.V.I., Husinec-Rez (CZ); UNIVERZITA PALACKEHO V OLOMOUCI, Olomouc (CZ)

( * ) Notice: Subject to any disclaimer, the term of this patent is extended or adjusted under 35 U.S.C. 154(b) by 50 days.

(21) Appl. No.: 14/352,210
(22) PCT Filed: Oct. 24, 2012
(86) PCT No.: PCT/CZ2012/000106
§ 371 (c)(1),
(2) Date: Apr. 16, 2014
(87) PCT Pub. No.: WO2013/060307
PCT Pub. Date: May 2, 2013

(65) Prior Publication Data
US 2014/0303390 A1 Oct. 9, 2014

(30) Foreign Application Priority Data

Oct. 24, 2011 (CZ) .............................. PV 2011-676

(51) Int. Cl.
C07F 15/02 (2006.01)
C07F 5/05 (2006.01)
(Continued)

(52) U.S. Cl.
CPC ................. *C07F 15/06* (2013.01); *C07F 5/027* (2013.01); *C07F 5/05* (2013.01); *C07F 15/02* (2013.01)

(58) Field of Classification Search
CPC ............ C07F 5/027; C07F 5/05; C07F 15/02; C07F 15/06
USPC ..................................... 556/8; 568/5
See application file for complete search history.

(56) References Cited

U.S. PATENT DOCUMENTS

| 4,975,447 A | 12/1990 | Schoenwald et al. |
| 5,010,204 A | 4/1991 | Antonaroli et al. |

(Continued)

FOREIGN PATENT DOCUMENTS

DE 10 2007 026701 12/2008

OTHER PUBLICATIONS

Benfodda Z et al: "Synthesis and investigation of inhibition effect of fluorinated sulfonamide derivatives on carbonic anhydrase", European J Med Chem, vol. 45, Mar. 1, 2010, pp. 1225-1229.

(Continued)

*Primary Examiner* — Porfirio Nazario Gonzalez
(74) *Attorney, Agent, or Firm* — Notaro, Michalos & Zaccaria P.C.

(57) ABSTRACT

Derivatives of boron cluster compounds of general formula I and their pharmaceutically acceptable salts and solvates, and their specific inhibition effect on the enzyme carbonic anhydrase IX, a protein overexpressed in cancer tissues. Methods of synthesis and the use of the novel derivatives. These inhibitors of human carbonic anhydrase IX can be used as active compounds of pharmaceuticals for diagnostics and/or therapy of cancer diseases.

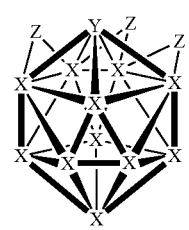

(I)

25 Claims, 13 Drawing Sheets

(51) Int. Cl.
  *C07F 15/06* (2006.01)
  *C07F 5/02* (2006.01)

(56) References Cited

U.S. PATENT DOCUMENTS

| | | |
|---|---|---|
| 5,055,480 A | 10/1991 | Pierce, Jr. |
| 5,059,613 A | 10/1991 | Pierce, Jr. |
| 5,093,332 A | 3/1992 | Shepard et al. |
| 5,225,424 A | 7/1993 | Schoenwald et al. |
| 5,242,937 A | 9/1993 | Pierce, Jr. |
| 5,424,448 A | 6/1995 | Dean et al. |
| 5,538,966 A | 7/1996 | May et al. |
| 5,646,142 A | 7/1997 | Dantanarayana et al. |
| 6,248,735 B1 | 6/2001 | Baldwin |
| 6,316,443 B1 | 11/2001 | Baldwin |
| 2004/0146955 A1 | 7/2004 | Supuran |

OTHER PUBLICATIONS

Chai-Ho Lee: "Preparation of Boronated Heterocyclic Compounds Using Intramolecular Cyclization Reaction", Bull. Korean Chem. Soc., vol. 29(2), Jan. 1, 2008, pp. 357-362.

Lee J D et al: "A convenient synthesis of the novel carboranyl• substituted tetrahydroisoquinolines: application to the biologically active agent for BNCT", Tetrahedron Lett, vol. 43, Jul. 29, 2002, pp. 5483-5486.

International Search Report and Written Opinion for PCT/CZ2012/000106.

International Preliminary Report on Patentability for PCT/CZ2012/000106 filed on Oct. 24, 2012.

○ C bearing R¹
● C-H

○ C bearing R[1]

● C-H

○ C bearing R$^1$
● C-H

CB-5am

CB-19am

○ C bearing R[1]
● C-H

CB-8a_am

CB-8b_am

CB-13am

○ C bearing R¹
● C-H

CARBONIC ANHYDRASE INHIBITORS AND METHOD OF THEIR PRODUCTION

FIELD OF ART

The present invention describes new derivatives of boron-containing clusters and their specific inhibitory effect toward the enzyme carbonic anhydrase IX, a protein overexpressed in cancer tissues. The invention also includes the synthetic procedure and the use of the above mentioned derivatives. The inhibitors of human carbonic anhydrase IX described in this invention can be used as active ingredients in pharmaceuticals used in cancer therapy.

BACKGROUND ART

Carbonic Anhydrases and Inhibitors Thereof

Various forms of the enzyme carbonic anhydrase (CA) catalyse hydration of carbon dioxide to generate bicarbonate anion ($HCO_3^-$) and a proton. Substrates of the reaction which is catalyzed by CA regulate a number of physiological processes, including formation and transport of $CO_2$, protons and bicarbonate anion, such as respiration, maintenance of pH levels, bone development and other processes. In the human organism, 12 catalytically active CA isoenzymes were identified which differ in their cellular localization and their expression in various tissues.

Clinical regulation of the activity of human carbonic anhydrase (hCA) by small molecular inhibitors proved to be reliable therapeutic method for a number of human diseases and already for several decades it remains a major component of therapy for high blood pressure, glaucoma, hyperthyrosis and hypoglycemia (reviewed in: Supuran, *Nat. Rev. Drug Discov.*, 7, 2008, 168). Classical inhibitors of carbonic anhydrasese, binding into the active site of CA, are aromatic or heteroaromatic sulfonamides.

Clinically used inhibitors of hCA which are derivatives of sulfonamide heterocyclic derivatives include for example brinzolamide (see patents U.S. Pat. No. 5,646,142, U.S. Pat. No. 5,424,448, U.S. Pat. No. 5,093,332, U.S. Pat. No. 5,538,966), dorzolamide (patents: U.S. Pat. No. 6,316,443, U.S. Pat. No. 6,248,735, LT 3368 and others), ethoxzolamide (for example patents U.S. Pat. No. 5,059,613, U.S. Pat. No. 4,975,447), acetazolamide and methazolamide (for example US 20040146955, U.S. Pat. No. 5,242,937, U.S. Pat. No. 5,225,424, U.S. Pat. No. 5,055,480, U.S. Pat. No. 5,010,204). Inhibitors from the group of aromatic sulfonamides include clinically used inhibitors dichlorphenamide and indisulam.

Although a large number of various inhibitors of CA was developed, a major problem is their nonspecificity and non-selectivity. As a consequence of non-specific inhibition of all hCA forms present in the human body, the clinically used inhibitors have many side effects including toxicity. Development of inhibitors specific toward certain isoform of hCA thus still remains a current and important task.

Human carbonic anhydrase IX (hCA IX) is an isoform bound to the outer cell membrane (its catalytic domain is located in the extracellular space). At physiological conditions, hCAIX is expressed only in specific tissues of gastrointestinal tract. Its overexpression was shown during hypoxia in cancer cells both in vitro and in vivo. Expression of hCAIX was detected in carcinomas of cervix, ovaries, kidneys, esophagus, lungs, breasts and brain. In tumors, hCAIX is a molecule crucial for the maintenance of intracellular pH on normal level and its expression provides the hypoxic tumor cells with an advantage in growth at acidic conditions ((J. Chiche et al., *Cancer Res.*, 69, 2009, 358). hCAIX enzyme is thus a convenient target for development of specific inhibitors used as anti-cancer therapeutics with new mechanism of action (D. Neri and C. Supuran, *Nature Reviews*, 10, 2011, 767).

Boron Cluster Compounds and their Use in Medicinal Chemistry

Basic archetype for stable cluster borane space geometry is the highly symmetric closed icosahedron (closo-compounds) and its open fragments, which can be derived by notional removal of one to three (or even more) vertices followed by addition of extra protons to cluster edges present at the open cluster face. This in simplicity leads to open structures classified as nido-, arachno- and hypho-skeletal types. Notional replacement of one or more borane cage BH units by main group elements furnishes heteroboranes (e.g. carboranes, thiaboranes, azaboranes, etc.), whereas in case of fragments containing transition metal atom it leads to metallaheteroboranes. Structure of the molecule, number of skeletal bonding electrons, number of heteroatoms that can be present in the particular cluster type and overall cluster charge can be predicted using the electron counting structure formalism introduced by Wade and Williams (e.g. Williams, R. E., *Chem. Rev.* 92, 1992, 177). At least one hydrogen atom is bonded to each of the skeletal boron or carbon atoms. This is bound by classical two electron-two center bond and points out of the molecule. In case of open cages, extra hydrogen atoms can be either connected in the same manner or more frequently localized at the edge interconnecting two boron atoms, and in this case bound by three center bond as bridge hydrogen. Hydrogen atoms can be replaced by a wide variety of substituents known from organic chemistry. The variety of known structural archetypes is currently rather rich and the number of known compounds can be estimated as being higher than 50 000. The boron cluster species represent thus an interesting counterpart to organic pharmacophores as result of their space geometries, different types of skeletal bonding and in general, higher chemical stabilities of closo-a nido-compounds.

Until recently, the boron cluster compounds have found medicinal applications almost exclusively in Boron. Neutron Capture Therapy (BNCT) of brain tumors (glioblastoma) and skin cancer (melanoma). In principle, this method is based on selective accumulation of $^{10}B$ nuclide-rich compounds in the malignant tissue and subsequent irradiation by a beam of thermal or epithermal neutrons. A subsequent nuclear reaction destroys the malignant cells. Several hundreds of compounds have been designed ranging from simple compounds like $[B_{12}H_{11}SH]^{2-}$ to sophisticated systems based on polyamines, steroids, porphyrines, phtalocyanines, antigens, monoclonal antibodies, nucleosides, nucleotides, liposomes, etc. as the vehicles to enhance the selective accumulation of the boron in tumors. The area of BNCT has been reviewed many times, for information see the recent review articles, e.g. Soloway et al., *Chem. Rev.* 98, 1998, 1515; Hawthorne and Lee, *J. Neuro-Oncol.* 62, 2003, 33.

Another application of boron clusters in medicine reports the use of compounds substituted by iodine or bromine in radioimaging or as contrast agents with heavy load of radioactive I, $^{59}Co$ or as tritiated compounds, i.e. compounds labelled by radionuclides for use in nuclear medicine (Hawthorne and Maderna, *Chem. Rev.* 99, 1999, 3421).

All the above compounds however have been assumed to play only the role of inert carriers of boron or radioactive tracers into patient's tissues and usually have not been studied for their truly therapeutic action. In respect to this application, main importance of results acquired in BNCT file consists in the proof that boron compounds can penetrate from blood stream and further into malignant tissues. Another important feature is that the stable 12- (closo-) and 11- (nido-) vertex compounds have been proven to show low toxicity even at high concentrations, when the respective data are available. Indeed, the concentrations necessary for BNCT treatment are several orders higher than those assumed for the therapeutic action of similar compounds.

Design and development of boron cluster compounds having pharmaceutical effect, lying beyond the scope of BNCT, emerged over past 10 or 15 years. The progress in this area is described in several recent review articles (Valliant, *Coord. Chem. Rew.*, 232, 2002, 173; Lesnikowski, *Collect. Czech. Chem. Commun.*, 72, 2007, 1646; Sivaev and Bregadze, *Eur. J. Inorg. Chem.*, 2009, 1433; Fatiah et al., *Chem Rev.* 111, 2011, 5701). Until now, main focus has been paid on molecular systems, which typically contained neutral icosahedral carboranes used here as hydrophobic pharmacophore replacing the phenyl ring present in known active substances. There are several reports in the literature describing isocahedral carboranes as potential antineoplastic and cytotoxic agents, estrogen agonists and antagonists, protein kinase C modulators and transthyretin amyloidosis inhibitors, the respective references can be found in the above-mentioned review articles.

The area of biological effects of metallacarboranes is significantly less developed. A cytotoxic effect of salts comprising cationic 11-vertex cationic ferratricarbadekaboranyl complexes has been described. A distinct cytotoxic effect was observed also in the case of halide complexes of vanadium a niobium with 10-vertex tricarbadekaboranyl ligands, which proved to be potent cytotoxic agents against murine and human leukemia and lymphoma growth as well as HeLa suspended uterine carcinoma. Similar effect exhibited similar polyhalide complexes of vanadium and niobium with tricarbaborane ligands. (Hall and Sneddon, *J. Inorg. Biochem.* 93, 2003, 125).

Small metallacarborane complexes containing $C_2B_4$ or $C_2B_3$ ligands and Ta, Fe, Co, Mo, or W as central cations express cytotoxic activity in murine and human tissue cultured cells (Hall et al., *Anticancer Res.* 20, 2000, 2345; Hall et al., *Appl. Organomet. Chem.* 14, 2000, 108). Recently, it has been shown that ionic molecular constructions based on connection of two or more metal bis(dicarbollides) via an organic linker can serve as potent and selective inhibitors of viral HIV-1 Protease enzyme (Cigler et al., *PNAS* 102, 2005, 15394).

During last decade, complexes of some metals also emerged as carborane analogues of "cis-platin". In these compounds, exo-skeletally C-substituted neutral 12-vertex ortho a meta-closo-carboranes bearing alkyl chains or alkyl chains with terminal donor groups —$NH_2$, —SH are employed as ligands in planar platinum complexes. These complexes exhibit efficiency comparable to "cis-platin". On the other hand, these compounds have shown an increased efficiency towards carcinoma cell lines resistant against complexes bearing organic ligands. Similar characteristics are also exhibited by tin complexes with bent structures (these compounds were described in several review articles, see e.g. Sivaev and Bregadze, *Eur. J. Inorg. Chem.* 2009, 1433.)

In general, it can be stated that most of the parent 12-vertex clusters and 11-vertex species derived from the former are highly chemically stable compounds, which according to literature exhibit a relatively low toxicity (e.g. Valliant, *Coord. Chem. Rew.*, 232, 2002, 173; Lesnikowski, *Collect. Czech. Chem. Commun.*, 72, 2007, 1646). Such compounds have an abiotic character and are thus stable in biological environment, i.e., they are unusually resistant towards catabolism and degradations by enzymatic systems.

The cluster surface is composed of hydridic hydrogen atoms $B^{\delta+}$—$H^{\delta-}$, which cannot form classical hydrogen bonds. This causes repulsion of water molecules out of the surface of the cluster fragment. This effect enhances hydrophobic interactions with receptors and increases the in vivo stability (e.g. Lesnikowski, *Collect. Czech. Chem. Commun.*, 72, 2007, 1646). Namely it is well known that in the case of icosahedral ferra-a cobaltacarboranes the central central metal atom is incorporated in the complex very tightly, which precludes its cleavage (with exception of use of extreme drastic conditions), and thus it is not susceptible to any kind of interactions or chemical reactions.

Sulfamide and Sulfonamide Derivatives of Carboranes and their Possible by-Products As described above, structures of majority of known inhibitors of hCA IX a hCA II that are based on organic compounds, contain primary sulfonamide $S(O)_2$—$NH_2$ or sulfamide NH—$S(O)_2$—$NH_2$ groups. The amidic end of the molecule is coordinated to zinc atom present in the active centre of the enzyme. However no compounds containing sulfonamide or sulfamide group present simultaneously together with carborane or metallacarborane cluster in one single molecule have been published in the literature, yet. Compounds of this type are thus novel and are the subject of this patent application.

A different situation exists in case of carboranes and metallacarboranes derivatives substituted with primary amine (—$NH_2$) or ammonium (—$NH_3$) group attached either directly to skeletal boron or carbon atoms or via an aliphatic or other chain of various lengths, based primarily on carbon atoms. A relatively large number of such compounds has been described in the literature, at least one entry exists for each of the skeletal archetypes; details until 2001 can be found in review articles (Valliant, *Coord. Chem. Rew.*, 232, 2002, 173, Sivaev and Bregadze, *Collect. Czech. Chem. Commun.* 64, 1999, 783), or in original literature published during recent years (e.g. Woodhouse and Rendina, *Dalton Trans.* 2004, 3669; Olshevskaya et al. *Synlet,* 2010, 1265).

As described in the following disclosure of invention, some of these primary amines can be employed as starting compounds for introduction of sulfamide group into molecule. The largest amount of known amine derivatives has been reported in case of icosahedral dicarbaboranes, inclusive C—R—$NH_2$ (R=alkane comprising 1 to 3 carbon atoms) substituted compounds derived from basic series of o-, m- a p-carborane. In case of o-carborane, such compounds were prepared by insertion reactions of acetylenes, substituted with protected amine group, into open 10-vertex cage of bis(acetonitrile) decaborane. Alternatively, the synthesis can be performed via direct lithiation of carborane bonds (using BuLi) followed by subsequent reaction with brom alkyl-phthalimides (for $C_2$ a $C_3$ length of alkyl, but not for $C_1$ alkyl). In addition to this, some 11-vertex ammonium derivatives derivable from above mentioned 12-vertex icosahedral o-series are known, prepared by well elaborated methods of the boron atom degradation from the cage. Such degradation reactions proceed by attack of basic reagents on the cage (e.g. Valliant, *Coord. Chem. Rew.*, 232, 2002, 173, Woodhouse and Rendina, *Dalton Trans.* 2004, 3669). Other known derivatives in the icosahedral carborane series are ammonium derivatives of the $[CB_{11}H_{12}]^-$ anion substituted either on the carbon atoms or boron atom in skeletal position B(12) (see Körbe et al., *Chem. Rev.* 106, 2006, 5208). In addition, $NH_3^+$-derivatives of the $[B_{12}H_{12}]^{2-}$ anion have been also described (see Grüner et al., *Collect. Czech. Chem. Commun.* 62, 1997, 1185).

Carbon substituted derivatives of stable icosahedral metallacarborans bearing primary —$NH_2$—$NH_3^+$ groups were reported for the series of mixed and full sandwich ferratricarbollides. It should be noted that these compounds were not prepared by direct substitution, however only via metal insertion reactions into amine substituted tricarbollide ligands. (Grüner et al., *Eur. J. Inorg. Chem.:* 2004, 1402). Surprisingly enough, no C-substituted primary amines prepared neither by direct method nor by metal insertion have been reported in the series of the most extensively studied metal bis(dicarbollides), yet (see Sivaev and Bregadze, *Collect. Czech. Chem. Commun.* 64, 1999, 783, Sivaev and Bregadze, *J. Organomet. Chem.* 27, 2000, 614-615). Only compounds bearing more substituents on nitrogen atom were prepared, proceeding via metal insertion into already substituted dicarbollide ligands.

In contrast to C-substituted compounds, a wide series of B-substituted ammonium cobalt bis(dicarbollide) has been described. These species comprise the ammonium group attached in a bridging manner or bonded by single bonds to boron atom B(12). All of them can be prepared via direct substitution of the cobalt sandwich complex. Known compounds are summarized in comprehensive reviews (Sivaev and Bregadze, *Collect. Czech. Chem. Commun.* 64, 1999, 783; Sivaev and Bregadze, *Eur. J. Inorg. Chem.* 11, 2009, 1433), or described in the original literature (e.g. Šícha et al., *Dalton Trans.* 2009, 851).

Also another series of B-substituted derivatives of cobalt bis(dicarbollide) is known, which comprise compounds with ammonium group attached via a longer chain connector. Such derivatives are accessible from reactive species bearing dioxane ring (Plešek et al., *Collect. Czech Chem. Commun.* 62, 1997, 47), its analogue substituted with tetrahydropyrane (Llop et al., *Dalton Trans.* 2003, 556), or paramagnetic compounds having $Fe^{3+}$ and $Cr^{3+}$ central atoms in their structures (Plešek et al., *J. Organomet. Chem.* 692, 2007, 4801; Olejniczak et al., *Electroanalysis,* 21, 2009, 501). These compounds have cyclic ether ring attached to the cage boron atom B(12) by an oxonium oxygen atom and this ring can be thus easily cleaved using organic nucleophilic reagents. Such ring opening results in B(12)-$(OCH_2CH_2)_2$—X bonding arrangement. Those reactions have been recently widely used for introduction of metal bis(dicarbollide) fragment into various functional organic molecules designed for metal extractions and complexations, in synthesis of conducting polymers, compounds for BNCT; as has been described in a recent review article (Semioshkin et al., *Dalton Trans.* 2008, 977).

It should be noted that there exists even a larger series of known compounds beyond the above descriptions, wherein the substituent on icosahedral or 11-vertex cluster is secondary, tertiary or quarternary amine group. However, these compounds are not suitable for conversions to the sulfamide groups and thus are not considered here as building blocks for design of hCA IX inhibitors, which forms the subject-matter of the invention described below.

DISCLOSURE OF THE INVENTION

A subject-matter of this invention is the provision of a new class of inhibitors of enzyme carbonic anhydrase IX, where a selective inhibition is achieved owing to a parallel presence of two structural factors being substituted boron-containing clusters as a hydrofobic pharmacophore and a group capable of bonding to the active site of the enzyme. The high inhibitory effect of the newly prepared compounds can be ascribed to the achievement of a new type of substitution, specific for the enzyme carbonic anhydrase IX. It was experimentally verified that the parent ionic compounds, substituted on the hydrophobic clusters of carboranes and metallocarboranes, bearing an amino group or ammonium group, are ineffective for the inhibition of this enzyme.

The subject-matter of the invention are compounds of general formula I

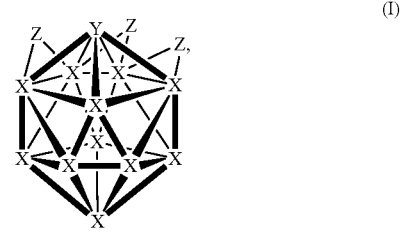

(I)

wherein

X can be selected independently from a group comprising BH, CH, $BR^1$ and $CR^1$, whereas concurrently at most four X, preferably at most three X, can be CH or $CR^1$, and whereas at least one group $BR^1$ or $CR^1$ is present;

$R^1$ in at least one substituent X is selected from a group comprising A-$NHSO_2NH_2$, A-$SO_2NH_2$ and A-O—$SO_2NH_2$, $R^1$ in other substituents X can be selected independently from a group comprising A-$NHSO_2NH_2$, A-$SO_2NH_2$, A-O—$SO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing a heteroatom O, S or N, $C_1$-$C_8$ alkoxy, $C_1$-$C_8$ alkylhydroxy, $C_1$-$C_8$ alkylmercapto, OH, $NH_2$, $NH_3^+$, $C_1$-$C_8$ alkylammonium, $C_1$-$C_8$ alkylamino, halogen;

A is selected from a group comprising a single bond or bivalent linear $C_1$-$C_{10}$ hydrocarbon chain, wherein some carbon atoms can be replaced by heteroatoms selected from a group comprising N, S, O, or by a group selected from $C_6$-$C_{10}$ arylene and $C_4$-$C_{10}$ heteroarylene, wherein the heteroatom is selected from O, N and S;

Y is selected from a group comprising BH, CH, $BR^1$, $CR^1$, $MR^2$, or Y is not present;

M is a metal of VIB or VIIIB group of periodical table, preferably Cr, Fe, Ru or Co;

$R^2$ is selected from a group comprising a structure of general formula II

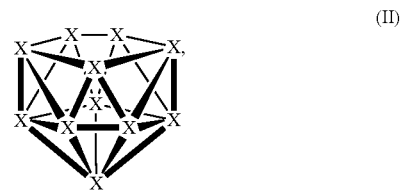

(II)

wherein X is as defined above whereas concurrently at most three X can be CH or $CR^1$; $R^1$ is selected independently from a group comprising A-O—$SO_2NH_2$, A-$SO_2NH_2$, A-$NHSO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing O, S or N as heteroatom, $C_1$-$C_8$ alkoxy, $C_1$-$C_8$ alkylhydroxy, $C_1$-$C_8$ alkylmercapto, OH, $NH_2$, $NH_3^+$, $C_1$-$C_8$ alkylammonium, $C_1$-$C_8$ alkylamino, halogen,
and A is as described above,
η$^5$-bonded cyclopentadienyl, optionally substituted by 1 to 5 methyls, and
η$^6$-bonded phenyl ring, optionally bearing from 1 to 6 $C_1$-$C_6$ alkyl groups;
Z is H or is not present; whereas from one to three Z are H only when Y is not present;
alkyl denotes a linear or branched $C_1$-$C_8$ hydrocarbon moiety not comprising multiple bonds, which can optionally be substituted by one or more substituents selected from a group comprising OH, halogen, $NH_2$, COOH, $CONH_2$, CN, $NO_2$, SH;
alkenyl denotes a linear or branched $C_2$-$C_8$ hydrocarbon chain, comprising at least one double bond, which can optionally be substituted by one or more substituents selected from a group comprising OH, halogen, $NH_2$, COOH, $CONH_2$, CN, $NO_2$, SH, $SO_3H$;
alkynyl denotes a linear or branched $C_2$-$C_8$ hydrocarbon chain, comprising at least one triple bond and optionally also at least one double bond, which can be optionally substituted by one or more substituents selected from a group comprising OH, halogen, $NH_2$, COOH, $CONH_2$, CN, $NO_2$, SH, $SO_3H$;
aryl denotes a $C_6$-$C_{10}$ aromatic carbocyclic group, comprising at least one aromatic ring or condensed aromatic rings, which can be optionally substituted by one or more substituents selected from a group comprising OH, halogen, $NH_2$, COOH, $CONH_2$, CN, $NO_2$, SH, $SO_3H$;
heteroaryl denotes a $C_4$-$C_{10}$ aromatic carbocyclic group, comprising at least one aromatic ring or condensed aromatic rings, in which at least one carbon atom is replaced by a heteroatom selected from a group comprising N, S, O, which can be optionally substituted by one or more substituents selected from a group comprising OH, halogen, $NH_2$, COOH, $CONH_2$, CN, $NO_2$, SH, $SO_3H$; alkoxyl denotes a monovalent group derived from $C_1$-$C_8$ alcohol by the separation of a hydrogen atom from hydroxygroup;
alkylamino is a group, created by a substitution of one or two hydrogen atoms of aminogroup by $C_1$-$C_8$ alkyl;
alkylmercapto is a monovalent group derived from $C_1$-$C_8$ thiol by the cleavage of a hydrogen atom from SH group;
halogen is fluorine, chlorine, bromine or iodine atom;
bivalent linear $C_1$-$C_{10}$ hydrocarbon chain refers to a chain containing single bonds, optionally also double bonds, which binds oneself by terminal carbons;
and/or their pharmaceutically acceptable salts and solvates.

Salts of cations or anions falling into the general formula I with respective counterions being acceptable for use in pharmacy are understood as pharmaceutically acceptable. Examples of pharmacologically acceptable salts are salts of alkali metals and alkali earths, ammonium salts, metal salts, salts of inorganic or organic acid anions, for example halogen salts, sulphates, carbonates, acetic salts, succinate salts and many others.

Solvates comprise, together with the molecule of compound falling into the general formula I, also molecules of water or other substances, for example solvents, which are acceptable for use in pharmaceutical formulations.

A preferred embodiment of the invention are compounds of general formula I wherein
X is as defined above,
$R^1$ in at least one substituent X is selected from a group comprising A-$SO_2NH_2$, A-O—$SO_2NH_2$,
$R^1$ in other substituents X can be selected independently from a group comprising A-$SO_2NH_2$, A-O—$SO_2NH_2$, A-$NHSO_2NH_2$, $C_6$-$C_{10}$ aryl, $C_1$-$C_8$ alkyl and $C_1$-$C_8$ alkoxy, $C_1$-$C_8$ alkylhydroxy, OH, $NH_2$, $NH_3^+$, $C_1$-$C_8$ alkylammonium, halogen;
A is as described above,
Y is selected from a group comprising BH, CH, $BR^1$, $CR^1$, $MR^2$, or Y is not present;
M is a metal of VIB or VIIIB group of periodical table, preferably Cr, Fe, Ru or Co;
$R^2$ is selected from a group comprising
a structure of general formula II

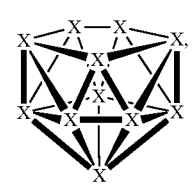

(II)

wherein X is as defined above whereas concurrently at most three X can be CH or $CR^1$; $R^1$ is selected independently from a group comprising A-O—$SO_2NH_2$, A-$SO_2NH_2$, A-$NHSO_2NH_2$, $C_1$-$C_8$ alkyl, $C_6$-$C_{10}$ aryl, $C_1$-$C_8$ alkoxy, $C_1$-$C_8$ alkylhydroxy, OH, $NH_2$, $NH_3^+$, $C_1$-$C_8$ alkylamino, $C_1$-$C_8$ alkylammonium, halogen,
wherein A is as described above,
η$^5$-bonded cyclopentadienyl, optionally substituted by 1 to 5 methyls, and
η$^6$-bonded phenyl ring, optionally bearing from 1 to 6 $C_1$-$C_6$ alkyl groups;
Z is H or is not present; whereas from one to three Z are H only when Y is not present,
and their pharmaceutically acceptable salts and solvates.

In a preferred embodiment of the invention the compound of general formula I is selected from [1,2-$C_2B_{10}H_{12}$], [1,7-$C_2B_{10}H_{12}$], [1,12-$C_2B_{10}H_{12}$], [1-$CB_{11}H_{12}$]$^-$, wherein one hydrogen atom is replaced by a substituent selected from the group comprising A-$SO_2NH_2$, A-O—$SO_2NH_2$, A-$NHSO_2NH_2$ and further at most three hydrogen atoms can be replaced by $R^1$ selected independently from a group comprising A-$SO_2NH_2$, A-O—$SO_2NH_2$, A-$NHSO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing heteroatom O, S or N, $C_1$-$C_8$ alkoxy, $C_1$-$C_8$ alkylmercapto, $C_1$-$C_8$ alkylhydroxy, OH, $NH_2$, $NH_3^+$, $C_1$-$C_8$ alkylamino, $C_1$-$C_8$ alkylammonium, halogen; wherein A has the meaning described above.

In another preferred embodiment of the invention the compound of general formula I is selected from [7-$CB_{10}H_{13}$]$^-$, [7,8-$C_2B_9H_{12}$]$^-$, [7,9-$C_2B_9H_{12}$]$^-$, [7,8,9-$C_3B_8H_{11}$]$^-$, [7,8,10-$C_3B_8H_{11}$]$^-$, wherein one hydrogen atom is replaced by selected from the group comprising A-$SO_2NH_2$, A-O—$SO_2NH_2$, A-$NHSO_2NH_2$ and further at most three hydrogen atoms can be replaced by $R^1$ selected independently from a group comprising A-$SO_2NH_2$, A-O—$SO_2NH_2$, A-$NHSO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing heteroatom O, S or N, $C_1$-$C_8$ alkoxy, $C_1$-$C_8$ alkylmercapto, $C_1$-$C_8$ alkylhydroxy, OH, $NH_2$, $NH_3^+$, $C_1$-$C_8$ alkylamino, $C_1$-$C_8$ alkylammonium, halogen; wherein A has the meaning described above.

In a further preferred embodiment of the invention the compound of general formula I is [$C_2B_9H_{10}R^1Y$] or [$C_3B_8H_{10}R^1Y$], wherein substituent $R^1$ is selected from the group comprising A-$SO_2NH_2$, A-O—$SO_2NH_2$, A-$NHSO_2NH_2$, and Y is $MR^2$, whereas M is Co and $R^2$ is $[7,8\text{-}C_2B_9H_{11}]^{2-}$, $[7,9\text{-}C_2B_9H_{11}]^{2-}$, $[7,8\text{-}C_2B_9H_{10}R^1]^{2-}$ or $[7,9\text{-}C_2B_9H_{10}R^1]^{2-}$, wherein the substituent $R^1$ is selected independently from a group comprising $A\text{-}SO_2NH_2$, $A\text{-}O\text{-}SO_2NH_2$, $A\text{-}NHSO_2NH_2$, $C_1\text{-}C_8$ alkyl, $C_2\text{-}C_8$ alkenyl, $C_6\text{-}C_{10}$ aryl, $C_2\text{-}C_8$ alkynyl, $C_4\text{-}C_{10}$ heteroaryl containing heteroatom O, S or N, $C_1\text{-}C_8$ alkoxy, $C_1\text{-}C_8$ alkylmercapto, $C_1\text{-}C_8$ alkylhydroxy, OH, $NH_2$, $NH_3^+$, $C_1\text{-}C_8$ alkylamino, $C_1\text{-}C_8$ alkylammonium, halogen; wherein. A has the meaning described above.

In another preferred embodiment of the invention the compound of general formula I is $[C_3B_8H_{10}R^1Y]$, wherein substituent $R^1$ is selected from the group comprising $A\text{-}SO_2NH_2$, $A\text{-}O\text{-}SO_2NH_2$, $A\text{-}NHSO_2NH_2$, and Y is $MR^2$, whereas M is Fe and $R^2$ is $[C_3B_8H_{10}R^1]^-$ or $[C_3B_8H_{11}]^-$, wherein the substituent $R^1$ is selected independently from a group comprising $A\text{-}SO_2NH_2$, $A\text{-}O\text{-}SO_2NH_2$, $A\text{-}NHSO_2NH_2$, $C_1\text{-}C_8$ alkyl, $C_2\text{-}C_8$ alkenyl, $C_6\text{-}C_{10}$ aryl, $C_2\text{-}C_8$ alkynyl, $C_4\text{-}C_{10}$ heteroaryl containing heteroatom O, S or N, $C_1\text{-}C_8$ alkoxy, $C_1\text{-}C_8$ alkylmercapto, $C_1\text{-}C_8$ alkylhydroxy, OH, $NH_2$, $NH_3^+$, $C_1\text{-}C_8$ alkylamino, $C_1\text{-}C_8$ alkylammonium, halogen; wherein A has the meaning described above.

In the next preferred embodiment of the invention the compound of general formula I is $[C_3B_8H_{10}R^1Y]$, wherein substituent $R^1$ is selected from the group comprising $A\text{-}SO_2NH_2$, $A\text{-}O\text{-}SO_2NH_2$, $A\text{-}NHSO_2NH_2$, and Y is $MR^2$, whereas A has the meaning described above, M is Fe and $R^2$ is $\eta^5$-bonded cyklopentadienyl, optionally substituted by 1 to 5 methyls.

In another preferred embodiment of the invention the substituent $R^1$ in general formula I consists of group $A\text{-}NHSO_2NH_2$ for at least one X and $R^1$ for another one or more X can be selected independently from a group comprising $A\text{-}SO_2NH_2$ or $A\text{-}O\text{-}SO_2NH_2$, $A\text{-}NHSO_2NH_2$, phenyl and $C_1\text{-}C_4$ alkoxy, whereas A is a bond or bivalent linear $C_1\text{-}C_6$ hydrocarbon chain, in which optionally from 1 to 2 carbon atoms are replaced by oxygen atoms.

In yet another preferred embodiment of the invention the substituent $R^1$ in general formula I consists of group $A\text{-}SO_2NH_2$ or $A\text{-}O\text{-}SO_2NH_2$ for at least one X and $R^1$ for another one or more X can be selected independently from a group comprising $A\text{-}SO_2NH_2$ or $A\text{-}O\text{-}SO_2NH_2$, $A\text{-}NHSO_2NH_2$, phenyl and $C_1\text{-}C_4$ alkoxy, whereas A is a bond or bivalent linear $C_1\text{-}C_6$ hydrocarbon chain, in which optionally from 1 to 2 carbon atoms are replaced by oxygen atoms.

Compounds according to the general formula I for use as medicaments and/or as diagnostic agents are also the object of the present invention.

The object of the present invention also consists of compounds according to the general formula I for use in treatment and/or diagnostics of cancer, proliferative and hypoxic diseases, in particular in treatment of tumor diseases comprising hyperexpression of carbonic anhydrase IX, in particular epithelial cancers, for instance colorectal, lung, breast, prostate, cervical, ovary, oesophageal and brain.

The object of the invention also consists of compounds according to the general formula I for a production of medicament for treatment of tumor diseases comprising hyperexpression of carbonic anhydrase IX, in particular epithelial cancers, for instance colorectal, lung, breast, prostate, cervical, ovary, oesophageal and brain.

The object of the present invention also includes a method of treatment and/or diagnostics of tumor diseases comprising hyperexpression of carbonic anhydrase IX, in particular epithelial cancers, for instance colorectal, lung, breast, prostate, cervical, ovary, oesophageal and brain, wherein at least one compound is administered to a subject in need of such treatment.

The object of invention is also a method of production of compounds of general formula I, in which compounds of general formula III

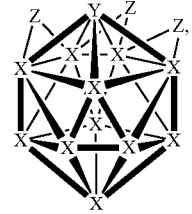

(III)

wherein

X is independently selected from a group comprising BH, CH, $BR^3$ and $CR^3$, whereas concurrently at most four X, preferably at most three X, can be CH or $CR^3$ and at least one group $BR^3$ or $CR^3$ is present;

$R^3$ consists of group $A\text{-}NH_2$ or $A\text{-}NH_3^+$ at least for one X and further substituents $R^3$ can be selected independently from a group comprising $A\text{-}NH_2$ or $A\text{-}NH_3^+$, $C_1\text{-}C_8$ alkyl, $C_2\text{-}C_8$ alkenyl, $C_6\text{-}C_{10}$ aryl, $C_2\text{-}C_8$ alkynyl, $C_4\text{-}C_{10}$ heteroaryl containing a heteroatom O, S or N, $C_1\text{-}C_8$ alkoxy, $C_1\text{-}C_8$ alkylhydroxy, $C_1\text{-}C_8$ alkylmercaptol, OH, $NH_2$, $NH_3^+$, $C_1\text{-}C_8$ alkylammonium, $C_1\text{-}C_8$ alkylamino, halogen;

A is selected from a group comprising a bond or linear $C_1\text{-}C_{10}$ hydrocarbon chain, wherein some carbon atoms can be replaced by heteroatoms chosen from a group comprising N, S, O, or by a group chosen from $C_6\text{-}C_{10}$ arylen, $C_4\text{-}C_{10}$ heteroarylen, wherein a heteroatom is chosen from O, N or S;

Y is selected from a group comprising BH, CH, $BR^3$, $CR^3$, $MR^3$, or Y is not present;

M is a metal of VIB or VIIIB group of periodical table, preferably Cr, Fe, Ru or Co;

$R^2$ is selected from a group comprising a structure of general formula II

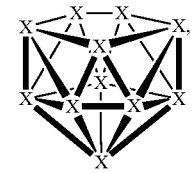

(II)

wherein X is as defined above, whereas at most three X can be concurrently CH or $CR^1$; $R^1$ is selected independently from a group comprising $A\text{-}O\text{-}SO_2NH_2$, $A\text{-}SO_2NH_2$, $A\text{-}NHSO_2NH_2$, $C_1\text{-}C_8$ alkyl, $C_2\text{-}C_8$ alkenyl, $C_6\text{-}C_{10}$ aryl, $C_2\text{-}C_8$ alkynyl, $C_4\text{-}C_{10}$ heteroaryl containing O, S or N as heteroatom, $C_1\text{-}C_8$ alkoxy, $C_1\text{-}C_8$ alkylhydroxy, $C_1\text{-}C_8$ alkylmercapto, OH, $NH_2$, $NH_3^+$, $C_1\text{-}C_8$ alkylammonium, $C_1\text{-}C_8$ alkylamino, halogen, wherein. A is as described above, η⁵-bonded cyklopentadienyl, optionally substituted by 1 to 5 methyls and η⁶-bonded phenyl ring, optionally bearing from 1 to 6 $C_1$-$C_6$ alkyl groups;

Z is H or is not present; whereas from one to three Z are H only when Y is not present, are treated by a sulfamide of formula $H_2NSO_2NH_2$.

The reaction is preferably carried out in an organic solvent, especially in an organic solvent selected from dioxan, dimethylformamide, dimethylether and dimethylether of diethylenglycol, whereas the aminogroup is replaced by sulfamide group.

The object of the invention is also a method of preparation of compound [8,8'-μ-($CH_2O(CH_3)$)-(1,2-$C_2B_9H_{10}$)$_2$-3-Co] as an intermediate for production of compounds of general formula I, wherein suspension of cobalt-bis(dicarbollide) salt in organic solvent being for example 1,2-dichloroethane is treated by para-formaldehyde or formaldehyde in presence of strong anorganic acid, selected from HCl, $H_2SO_4$ and $HSO_3CF_3$, and the product is then isolated by extraction and chromatography or used in mixture with other electroneutral products of the reaction directly for the production of compounds of general formula I.

The object of the invention is also a method of production of a compound of general formula I, characterized in that bis(dimethylsulfido) decaborane or bis(acetonitrile) decaborane of general formula ($L_2$-$B_{10}H_{12}$), where L is $Me_2S$ or $CH_3CN$, is treated by acetylene of general formula CH≡C—($CH_2$)$_n$—$NHSO_2NH_2$, where n=1-4, in a solvent selected from toluene, xylene, cumene, dioxane, dimethylformamide and dialkyether of ethylenglycol, where two carbon atoms are inserted into the borane cluster providing 1,2-carborane substituted by a sulphonamide group and the resulting products are isolated using a liquid chromatography.

The object of the invention is also a method of production of a compound of general formula I, characterized in that known compounds of formula [(HO—($CH_2$)$_n$)$_m$($C_2B_9H_{11-p}$)$_2$ Co]⁻ where n=1-3, m=1 or 2, p=0 or 1 deprotoned by $Cs_2CO_3$, sodium hydride or potassium tert-butoxide, are treated by sulfamoyl chlorid of general formula Cl—$SO_2NH_2$ in organic solvent selected from dioxane, dimethylformamide, tetrahydrofurane, dialkylether of ethylenglycol and dialkylether of diethylenglycol, or in mixture of organic solvent with toluene, xylene, cymene or cumene, where terminal oxygen atoms are substituted by sulfamoyl group.

The object of the invention is also a method of preparation of compound of general formula I, wherein the compound of formula [8,8'-μ-($CH_2O(CH_3)$)-(1,2-$C_2B_9H_{10}$)$_2$-3-Co] as described above, bearing bridging substituent {—O⁺($CH_3$)—$CH_2$—} between two atoms of boron in metallacarborane, or known compounds substituted by dioxane or tetrahydropyrane ring, being [(8-O($CH_2CH_2$)$_2$O)-(1,2-$C_2B_9H_{10}$)(1',2'-$C_2B_9H_{11}$)-3,3'-Co] or [(8-($CH_2$)$_5$O-(1',2'-$C_2B_9H_{11}$)-3,3'-CO], comprising also a reactive oxonium atom, are treated by sulfamide in an organic solvent selected from dioxane, dimethylformamide, tetrahydrofuran, dialkylether of ethylenglycol and dialkylether of diethylenglycol or in a mixture of an organic solvent with toluene, xylene, cymen or cumene, in the process an opening of the ring occurs as well as a terminal position substitution by a sulfamide group.

The object of the invention is also a method of preparation of compound of general formula I in which the icosaedric carborane 1,2-$C_2B_{10}H_{12}$ having carbon atoms in vicinal position, from which at least one is substituted by amino group, is treated by a sulfamide in a solvent selected from dioxane, dimethylformamide, dimethylether or in dialkylethers of ethylenglycol or in dialkylethers of diethylenglycol where Y being BH is splited off and concurrently a terminal amino group is substituted by sulfamide group and boron atom is substituted by a bridge group Z where Z is H.

The object of the invention is also a method of preparation of C-amino derivatives of formula [($H_2N$—($CH_2$)$_n$—$C_2B_9H_{10}$)($C_2B_9H_{11}$)Co] as precursors of compounds of general formula I, characterized in that an anhydric salt of icosaedric metallacarborane [($C_2B_9H_{11}$)$_2$Co] is treated by $R^3Li$, where $R^3$ is selected from methyl, butyl, phenyl and t-butyl, in dimethylether or diethylether of ethylenglycol and, after a balance establishment, by bromo- or iodo-alkylamine with protected amino group, where the protecting group is phtalimide, bis(trimetyl silyl) or t-Bu-carbonyl, the products are isolated by liquid chromatography and crystallization and then the protecting group is cleaved using ethylendiamine or by action of reduction agent as $NaBH_4$, acid or alkaline reagent.

The object of this invention is a method of production of of C-amino derivatives of formula [($H_3N$—($CH_2$)$_n$)$_m$($C_2B_9H_{11-p}$)Co], where n is n=1 to 3, m=1 or 2, p=0 or 1, as precursors of compounds of general formula I described in claim 1, characterized in that known C-hydroxyalkyl derivatives of icosahedral cobaltacarborane [(HO—($CH_2$)$_n$)$_m$($C_2B_9H_{11-p}$)$_2$—Co]⁻, where n is n=1 to 3, m=1 or 2, p=0 or 1, being trimethyl ammonium salts or cesium salts, are treated in presence of trimethylamine hydrochloride by toluene sulfonyl chloride or by trifluoromethyl sulfonyl chloride or by trifluoromethyl sulfonyl anhydride in acetonotrile, tetrahydrofurane or diethylether of ethylenglycol in presence of carbonate of alkalic metal, preferably cesium carbonate, or sodium hydride; resulted esters are isolated by recrystallization or by dissolution of product in aqueous methanol or ethanol, then precipitation of the tetramethyl ammonium salts and drying under vacuum and thus obtained salts are heated in acetonitrile, tetrahydrofurane or dioxane with excess of ammonia and finally isolated using a crystallization, precipitation in form of low soluble salts such as $R_4N^+$, where R is $C_1$ to $C_4$ alkane, and recrystallization or by liquid chromatography. Both monosubstituted and disubstituted alkylammonio/alkylamine compounds of the above mentioned formula can be prepared using this pathway in good yields.

The object of invention is also a method of preparation of C-amino derivatives of formula $H_2N$—($CH_2$)$_n$—$C_2B_{10}H_{10}$ substituted by aryl as precursors of compounds of general formula I characterized in that a substituted icosaedric carborane bearing at least one group $CR^1$ or $BR^1$ where $R^1$ is aryl, as it is described above, is treated by $R^3Li$, where $R^3$ is methyl, butyl, phenyl or t-butyl, in dimethylether or diethylether of ethylenglycol and, after a balance establishment, by bromo- or iodo-alkylamine with protected amino group, where the protecting group is phtalimide, bis(trimetyl silyl) or t-Bu-carbonyl, the products are isolated by liquid chromatography and by crystallization and then the protecting group is cleaved using ethylenediamine or by action of reduction agent as $NaBH_4$, acid or alkaline reagent.

The object of invention is also a method of preparation of C-amino derivative of formula 7-$H_2N$—($CH_2$)—$C_2B_9H_{10}$ as precursor of compounds of general formula I, characterized in that an icosaedric carborane of formula 1-Br—$CH_2$-1,2-$C_2B_{10}H_{11}$ is treated by aqueous ammonia in ethanol or by aqueous ammonia in toluene and product is then isolated by a liquid chromatography on silica gel.

The invention will be further illustrated by the examples which are not construed as limiting.

BRIEF DESCRIPTION OF THE DRAWINGS

FIG. 1 shows structural formulas of compounds described in examples n. 1-16.

FIG. 2 shows structural formulas of precursors described in examples n. 17-25.

FIG. 3 shows procedure for preparation of compound CB-2, which is 7-methylensulfamide-(7,8-nido-dicarbaundekaborate) (1-), described in example 2.

FIG. 4 shows procedure for preparation of compound CB-3, which is 1-sulfamide-closo-1-carbadodecaborate (1-), described in example 3.

FIG. 5 shows procedure for preparation of compound CB-4, which is 8-methylensulfamide-8'-methoxy-3,3'-commo-bis(1,2-dicarba-3-cobalta(III)-closo-dodecabor)ate (1-), described in example 4.

FIG. 6 shows procedure for preparation of compound CB-5, which is 1-methylenesulfamide-3,3'-commo-bis(1,2-dicarba-3-cobalta(III)-closo-dodecabor)ate (1-), described in example 5.

FIG. 7 shows procedure for preparation of compound CB-6, which is 7-methylensulfamide-8-phenyl-(7,8-nido-dikarbaundekabor)ate (1-), described in example 6.

FIG. 8 shows procedure for preparation of compounds CB-8a, which is 1-methylenesulfamide-9-phenyl-1,2-dicarba-closo-dodecaborane and CB-8b, which is 1-methylene-sulfamide-12-phenyl-1,2-dicarba-closo-dodecaborane, (equimolar mixture of isomers), described in example 7.

FIG. 9 shows procedure for preparation of isomeric compounds CB-10, which is 10-sulfamide-9'-amine-2,2'-commo-(1,7,10-tricarba-1',7',9'-tricarba-2-ferra(II)-closo-dodekabor)ane and CB-11, which is 9-sulfamide-10'-amine-2,2'-commo-(1,7,9-tricarba-1',7',10'-tricarba-2-ferra(II)-closo-dodekabor)ane, described in examples 8 and 9.

FIG. 10 shows procedure for preparation of compound CB-12, which is 9-sulfamide-9'-amine-2,2'-commo-bis(1,7,9-trikarba-2-ferra(II)-kloso-dodekabor)ane described in example 11.

FIG. 11 shows procedure for preparation of compound CB-13, which is 8-propylenesulfamide-7-phenyl-(7,8-nido-dicarbaundecabor)ate (1-), described in example 11.

FIG. 12 shows procedure for preparation of compound CB-15, which is 8-sulfamid-8-ethylaminomethylsulfamide-8'-methoxy-3,3'-commo-bis(decahydro-1,2-dicarba-3-cobalta(III)-closo-dodecabor)ate (1-), described in example 12.

FIG. 13 shows procedure for preparation of compound CB-15, which is 8-butyloxysulfamide-3,3'-commo-bis (decahydro-1,2-dicarba-3-cobalta(III)-closo-dodekabor)ate (1-), described in example 13.

FIG. 14 shows procedure for preparation of compound CB-17, which is 8-diethyleneoxysulfamide-3,3'-commo-bis (decahydro-1,2-dicarba-3-cobalta(III)-closo-dodekabor)ate (1-), described in example 14.

FIG. 15 shows procedure for preparation of compound CB-19, which is 1-methylenesulfamide-1,7-dicarba-closo-dodecaborane, described in example 15.

FIG. 16 shows procedure for preparation of compound CB-20, which is di(methylenesulfamide)-1,7-dicarba-closo-dodecaborane, described in example 16.

FIG. 17 shows procedure for preparation of compound CB-4Pre, which is reactive bridghe derivative 8,8'-μ-($CH_2O$ ($CH_3$))-(1,2-$C_2B_9H_{10}$)$_2$-3-Co, described in example 17.

FIG. 18 shows procedure for preparation of compound CB-5am, which is 1-methyleneammonio-3,3'-commo-bis (decahydro-1,2-dicarba-3-cobalta(III)-closo-dodecabor)ate (1-), described in example 18.

FIG. 19 shows procedure for preparation of compound CB-19am, which is 7-aminomethyl-8-fenyl-(7,8-nido-dikarbaundekabor)at (1-), described in example 19.

FIG. 20 shows procedure for preparation of compound CB-8am as isomeric mixture containing 1-methyleneamino-12-phenyl-1,2-dicarba-closo-dodecaborane and 1-methyleneamine-9-phenyl-1,2-dicarba-closo-dodecaborane, described in example 20.

FIG. 21 shows procedure for preparation of compound CB-13am, which is 8-propylammonio-7-phenyl-(7,8-nido-dicarbaundecabor)ate (1-), described in example 21.

FIG. 22 shows procedure for preparation of compound CB-15am, which is 8-(2-amineethyl)-ammonio-8'-methoxy-3,3'-commo-bis(1,2-dicarba-3-cobalta(III)-closo-dodecabor)ate (1-), described in example 22.

FIG. 23 shows procedure for preparation of compound CB-16am, which is 8-(5-ammoniopentoxy)-3,3'-commo-bis (1,2-dicarba-3-cobalta(III)-closo-dodecabor)ate (1-), described in example 23.

FIG. 24 shows procedure for preparation of compound CB-2am, 7-methyleneammonio-(7,8-nido-dikarbaundekabor)ate (1-), described in example 24.

FIG. 25 shows procedure for preparation of compound CB-17am, which is 8-(5-ammonio-3-oxa-pentoxy)-3,3'-como-bis(1,2-dicarba-3-cobalta(III)-closo-dodekabor)ate (1-), described in example 25.

FIG. 26 shows interaction of compound CB-1 with the active site of hCA II revealed by X-ray crystallography.

FIG. 27 shows interaction of compound CB-2 with the active site of hCA II revealed by X-ray crystallography.

EXAMPLES

Figure 1:
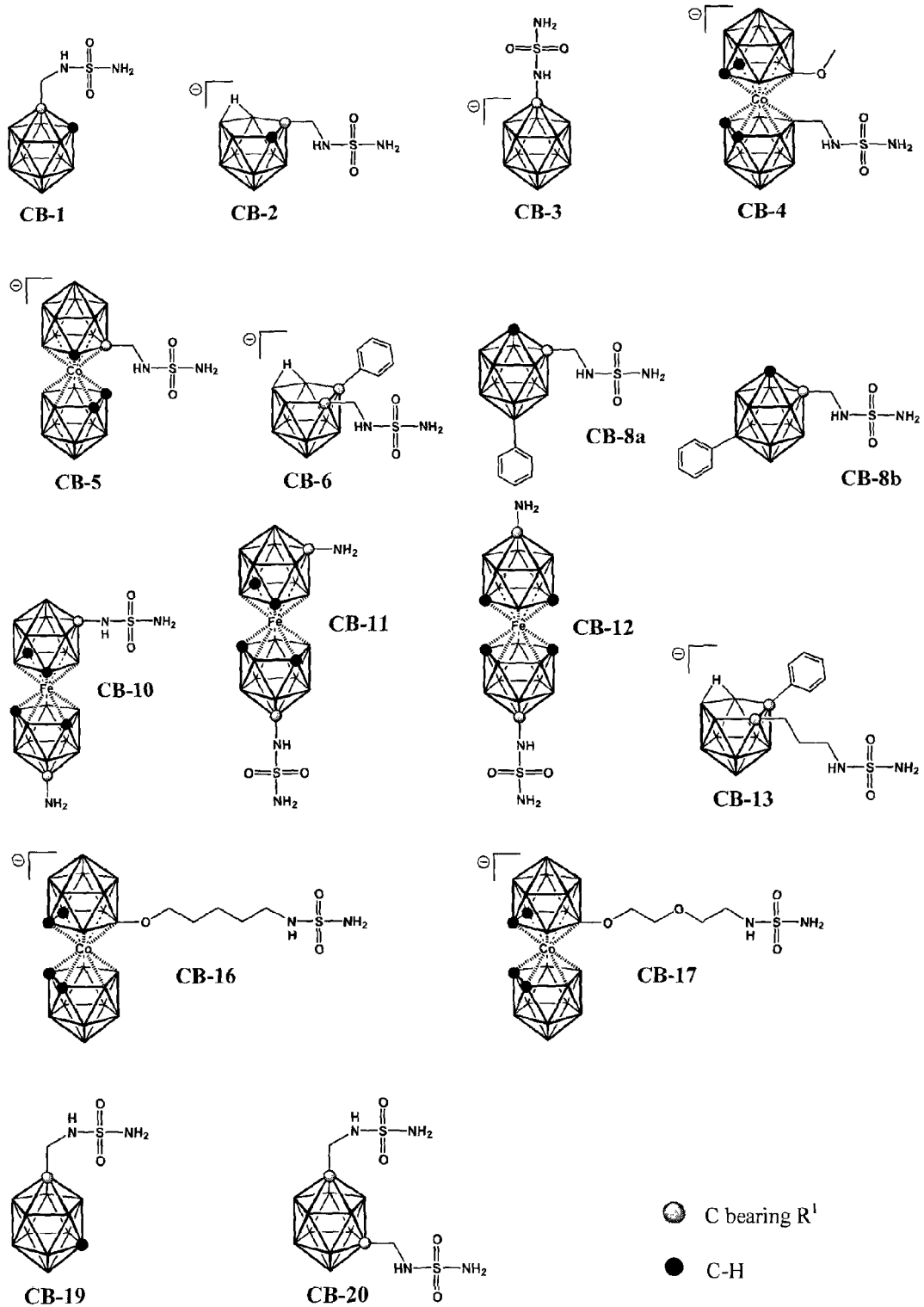
In FIGS. 1 to 25 the substituted carbon atom in the cluster is represented by gray sphere and CH group is represented by black sphere. Each unlabelled vertex is formed by BH group or B atom if it is substituted.

The invention is represented by specific examples below; the examples do not limit the scope of the invention.

List of Abbreviations Used h hour
RT room temperature
NMR Nuclear Magnetic Resonance
ppm Parts Per Million
MS ESI Electrospray Ionisation-Mass Spectrometry
TLC Thin Layer Chromatography
HEPES hydroxyethylpiperazine-N'-2-Ethanesulfonic Acid
DMSO dimethylsulfoxide
Et ethyl
Me methyl
n-BuOH n-butanol
isoPrOH isopropylalkohol
DME dimethyl ether
DMF dimethyl formamide
BNCT Boron Neutron Capture Therapy
MTT (3-(4,5-Dimethylthiazol-2-yl)-2,5-diphenyltetrazolium bromide
SDS sodium dodecyl sulphate
Identification of Compounds and their Purity Control
Multinuclear NMR Spectroscopy and Mass Spectrometry.

$^1$H, $^{13}$C, and $^{11}$B NMR spectra were measured on a Varian Mercury 400$^{Plus}$ Instrument. The spectra of all compounds were measured immediately after dissolution. $^{11}$B NMR (128 MHz) chemical shifts are given in ppm to high-frequency (low field) to $F_3B.OEt_2$ as the external reference. Residual solvent $^1$H resonances were used as internal secondary standards. Coupling constants $^1J(^{11}B-^1H)$ are taken from resolution-enhanced $^{11}$B spectra with a digital resolution of 2 Hz. The NMR data are presented in the text as follows: $^{11}$B NMR (9128 MHz): $^{11}$B chemical shifts δ($^{11}$B) (ppm), multiplicity, coupling J($^{11}B-^1H$) constants are given in Hz. Signal assignments are based on [$^{11}B-^{11}B$] COSY NMR spectroscopy. $^1$H NMR (400 MHz) and $^{13}$C (100 MHz): chemical shifts (δ($^1$H) are given in ppm relative to Me$_4$Si (0 ppm) as the external standard, coupling constants J(H,H) are given in Hz, assignment of δ($^1$H)-{$^{11}$B} resonances corresponds to NMR peaks observed in δ($^1$H)-{$^{11}$B selective} spectra.

Mass spectrometry measurements were performed on a Thermo-Finnigan LCQ-Fleet Ion Trap instrument using electrospray ionization (ESI) for ionic species or atmospheric pressure chemical ionization (APCI) for neural carborane derivatives with detection of negative or positive ions, respectively. Samples dissolved in acetonitrile (concentrations approximately 100 ng·ml$^{-1}$) were introduced to the ion source by infusion of (0.25 ml·h$^{-1}$), drying temperature was 160° C. (ESI) or 300° C. (APCI), drying gas flow 4 L min$^{-1}$, and pressure of nebulizing gas 55.158 kPa.

Synthesis (Method of Preparation) of New Compounds

Example 1

1-methylensulfamide-1,2-dicarba-closo-dodekaborane (compound CB-1)

To a mixture of the starting 1-NH$_2$CH$_2$-1,2-closo-C$_2$B$_{10}$H$_{11}$ (prepared according to Wilson et al., *Inorg. Chem.* 1992, 31, 1955) (144 mg, 0.83 mmol) and solid sulfamide (H$_2$NSO$_2$NH$_2$, 399 mg, 4.16 mmol) 1,4-dioxane (10 ml) was added under nitrogen. The slurry was heated to a reflux temperature under stirring and refluxed for additional 2 h. After cooling down to room temperature the solvent was removed under reduced pressure and a solid residue was extracted with mixture of ethyl acetate and diethyl ether (1:1 b.v.). The organic layer was separated by decantation and then treated with saturated solution o KHSO$_4$ (15 ml), twice with brine (2×15 ml) and the organic layer was separated. After drying over MgSO$_4$ and filtration the organic solvents were evaporated under reduced pressure. The solid residue was dissolved in a minimum volume of CH$_2$Cl$_2$ and CH$_3$OH solvent mixture (95:5), injected atop of a silica gel column (20×1.5 cm) and eluted with the same solvent as the mobile phase. Fractions containing the product were combined, evaporated under reduced pressure and dried in vacuum; yield: 168 mg (80%) white solid.

Found: $^1$H NMR (400 MHz; DMSO-d$_6$, Me$_4$Si) δ$_H$/ppm: 7.52 (1H, t, J=7.5 Hz, CH$_2$NHSO$_2$), 6.81 (2H, s, NHSO$_2$NH$_2$), 4.87 (1H, br. s, CH$_{carborane}$), 3.63 (2H, d, J=7.5 Hz, —CH$_2$—NH), 2.36 (2H, br. s, II), 2.15 (3H, bs, II), 2.05 (4H, br. s, H), 1.99 (1H, br. s, H); $^{11}$B NMR (128 MHz; DMSO-d$_6$; Et$_2$O.BF$_3$) δ$_B$/ppm: −3.19 (1B, d, J=145), −5.76 (1B, d, J=120), −9.83 (2B, d), −11.56 (2B, d), −13.00 (4B, d); $^{13}$C{$^1$H}NMR (100 MHz; DMSO-d$_6$; Me$_4$Si) δ$_C$/ppm: 75.6, 59.7, 49.9; m/z (HR ESI$^-$) found for: C$_3$H$_{15}$O$_2$N$_2$B$_{10}$S$^-$: 253.1788, calcd. 253.1790 [M]$^-$.

Example 2

7-methylensulfamide-(7,8-nido-dicarbaundekaborate) (1-), (compound CB-2)

Figure 3:
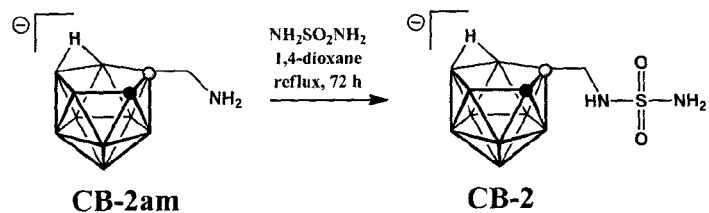

Structural formula of the compound CB-2 is depicted in FIG. 1. Scheme of the procedure used for preparation of the compound CB-2 is shown in FIG. 3.

1,4-dioxane (2 ml) was added to a solid mixture of the starting ammonium derivative 7-H$_3$NCH$_2$-7,8-nido-C$_2$B$_9$H$_{11}$ (50 mg, 0.3 mmol) and sulfamide (145 mg, 1.5 mmol) under nitrogen. The resulting slurry was stirred and heated under reflux for 72 h. After cooling down, silica gel was added (ca. 5 cm$^3$) the volatiles were removed under reduced pressure and solid was dried in vacuum. The solids were poured on a dry silica gel column (20×1.5 cm I.D.) and the products were eluted by chromatography starting from pure CH$_2$Cl$_2$ as the mobile phase to CH$_2$Cl$_2$—CH$_3$CN mixture 1:1 increasing stepwise the acetonitrile content. Yield 56 mg (76%), white solid.

Found: $^1$H {$^{11}$B} (δ$_{B-H}$) NMR (400 MHz; CD$_3$CN, Me$_4$Si) δ$_H$/ppm: 4.31 (1H, s, CH$_{carborane}$), 3.14 (1H, t, NH), 3.05 (2H, s, NH$_2$), 1.89 (2H, s, B9, 11-H), 1.64 (1H, s, B2-H), 1.22 (2H, t, CH$_2$), 1.20 (1H, s, B3-H), 1.18 (1H, s, B4-H), 1.17 (1H, s, B6-H), 1.07 (1H, s, B5H), 0.42 (1H, s, B1-H), −2.80 (1H, s, B(10)H); $^{11}$B NMR (128 MHz; CD$_3$CN; Et$_2$O.BF$_3$) δ$_B$/ppm: −10.97 (1B, d, J 143, B9), −11.31 (1B, d, J 142, B11), −14.90 (1B, d, J 159, B2), −16.94 (1B, d, J=159, B4), −18.39 (1 B, d, J=140, B5), −19.13 (1B, d, J=128, B3), −22.22 (1B, d, J 147, B6), −33.33 (1B, d, J 189, B10), −37.47 (1B, d, J 140, B1); $^{13}$C NMR (100 MHz; CD$_3$CN; Me$_4$Si) δ$_C$/ppm: 68.24 (1C, s, C$_{carborane}$), 52.46 (1C, d, CH$_{carborane}$), 30.14 (1C, t, CH$_2$); m/z (ESI$^-$) found: 242.17 (100%), 244.17 (10%), calcd. 242.18 (100%) 244.18 (10%) [M−H]$^-$.

Example 3

1-sulfamide-closo-1-carbadodecaborate (1-), (compound CB-3)

Figure 4:
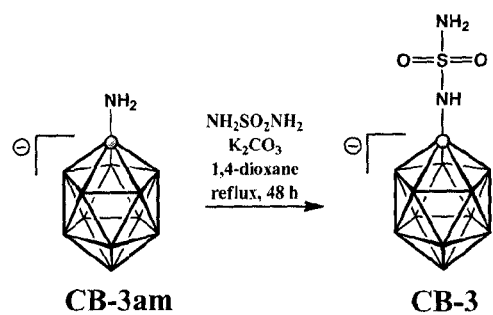

Structural formula of the compound CB-3 is depicted in FIG. 1. Scheme of the procedure used for preparation of the compound CB-3 is shown in FIG. 4.

A suspension was made containing 1-H$_3$N-closo-1-CB$_{11}$R$_{11}$ (220 mg, 1.4 mmol), prepared according to a published procedure (see e.g. Körbe et al., Chem. Rev. 106, 2006, 5208) and anhydrous K$_2$CO$_3$ (382 mg, 2.8 mmol) in 1,4-dioxane (20 ml). The content of the flask was stirred and heated to 100° C. under nitrogen over 1 h period and then solid sulfamide H$_2$NSO$_2$NH$_2$ (665 mg, 6.9 mmol) was added in one portion, and the reaction mixture was refluxed for 48 h. After cooling down, the solvent was removed under reduced pressure and the oily residue was dissolved in acetonitrile (5 ml) and the solution was filtered through a glass filter, which was washed by additional portion of the solvent (2×1 ml). Filtrate was layered with ether (40 ml) and the solvents were left to diffuse slowly. Yellowish crystals of CB-3 (188 mg) were obtained after three days of standing, which were sucked off and dried in vacuum. An additional portion of the pure product (34 mg) was obtained by evaporation of the mother liquors in vacuum and chromatography of the residue upon dissolution in solvent mixture of CH$_2$Cl$_2$ and CH$_3$CN 9:1 b.v. on a silica gel column (20×1 cm) stepwise increasing the content of acetonitrile to 1:1. Fractions containing the pure product were combined. Overall yield: 222 mg (67%).

Found: $^1$H {$^{11}$B}NMR (400 MHz; CD$_3$CN, Me$_4$Si) δ$_H$/ppm: 5.09 (4H, s, NHSO$_2$NH$_3$), 1.94 (5H, s, B7-11H), 1.40 (5H, s, B2-6H), 1.39 (1H, s, B121); $^{11}$B NMR (128 MHz; CD$_3$CN; Et$_2$O.BF$_3$) δ$_B$/ppm: −11.16 (1B, d, J 137, B12), −14.11 (5B, d, J 82, B7-11), −14.56 (5B, d, J 67, B2-6); $^{13}$C NMR (100 MHz; CD$_3$CN; Me$_4$Si) δ$_C$/ppm: 95.48 (1C, S, C$_{carborane}$); m/z (ESI$^-$) 237.30 (100%) 240.22 (5%), calcd. 237.19 (100%), 240.22 (5%), [M−H]$^-$.

Example 4

8-methylensulfamide-8"-methoxy-3,3'-commo-bis(1, 2-dicarba-3-cobalta(III)-closo-dodecabor)ate (1-), (compound CB-4)

Figure 5:
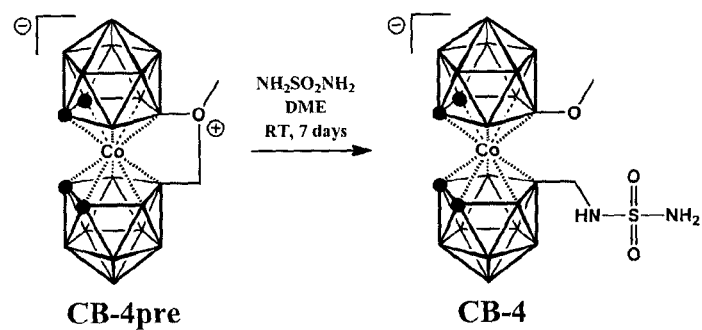

Structural formula of the compound CB-4 is depicted in FIG. 1. Scheme of the procedure used for preparation of the compound CB-4 is shown in FIG. 5.

The starting electroneutral bridged derivative [μ-8-CH$_2$-8"-CH$_3$O-(1,2-C$_2$B$_9$H$_{10}$)$_2$-3,3'-Co(III)] (200 mg, 0.5 mmol) was dissolved in DME (7 ml). Then, sulfamide H$_2$NSO$_2$NH$_2$ (157 mg, 1.6 mmol) was added under nitrogen and the reaction mixture was vigorously stirred at room temperature for 7 days. The reaction course was monitored periodically on TLC and by MS (ESI$^-$) and the stirring was stopped when the starting compound disappeared. The reaction was then quenched by evaporation of the solvent under reduced pressure. An orange solid was treated with 50 ml of CH$_2$Cl$_2$ and resulting slurry was flittered through a glass filter. Filtrate was poured into extraction funnel and shaken with 30 ml of diluted HCl (3 mol·l$^{-1}$). An orange precipitate containing crude zwittrionic product separated out whereas side products remained in the methylene chloride. The precipitate was flittered and dissolved in CH$_2$Cl$_2$ (10 ml) to which CH$_3$OH was added (150 μl), the solution was flittered and orange solution was layered with hexane (60 ml) an left to crystallize for 3 days. Pure crystalline product was obtained after filtration and drying in vacuum; yield 141 mg (55.8%).

Found: $^1$H NMR (400 MHz; CD$_3$CN, Me$_4$Si) δ$_H$/ppm, 3.96 (2H, s, 2 CH carborane), 3.92 (2H, s, 2 CH carborane), 3.46 (3H, s, CH$_3$O), 3.23 (2H, t, SO$_2$NH$_2$), 2.92 (1H, s, B(10)H), 2.91 (2H, s, B(4', 7')H), 2.77 (2H, s, B(4, 7)H), 2.64 (1H, s, B(10')H), 2.60 (1H, t, NH), 2.18 (2H, s, B(9", 12')H), 1.94 (2H, s, B(9, 12)H), 1.61 (1H, s, B(6)H), 1.57 (2H, s, B(5', 11')H), 1.25 (2H, d, CH$_2$NH), 1.54 (2H, s, B(5, 11)H), 1.43 (1H, s, B(6")H); $^{11}$B NMR (128 MHz; CD$_3$CN; Et$_2$O.BF$_3$) δ$_B$/ppm: 25.46 (1B, s, B8'), 9.22 (1B, s, B8), 0.87 (1B, d, J 143, B10), −2.13 (1B, d, J 143, B10"), −4.58 (2B, d, J 140, B9, 12), −6.29 (4B, d, J 137, B4, 7, 9', 12'), −7.74 (2B, d, J 186, B4', 7'), −18.30 (2B, d, J 125, B5, 11), −18.92 (2B, d, J 131, B5', 11), −22.65 (1B, d, J 180, B6), −27.62 (1B, d, J 153, B6"); $^{13}$C NMR (100 MHz; CD$_3$CN; Me$_4$Si) δ$_C$/ppm: 57.84 (1C, t, CH$_2$), 52.58 (2C, d, CH carborane), 49.12 (2C, d, CH carborane), 14.58 (1C, q, CH$_3$); m/z (ESI$^-$) 462.38 (100%), 465.38 (10%), calcd. 462.29 (100%), 465.29 (10%) [M−H]$^-$.

Example 5

1-methylenesulfamide-3,3'-commo-bis(1,2-dicarba-3-cobalta(III)-closo-dodecabor)ate (1-), (compound CB-5)

Figure 6:
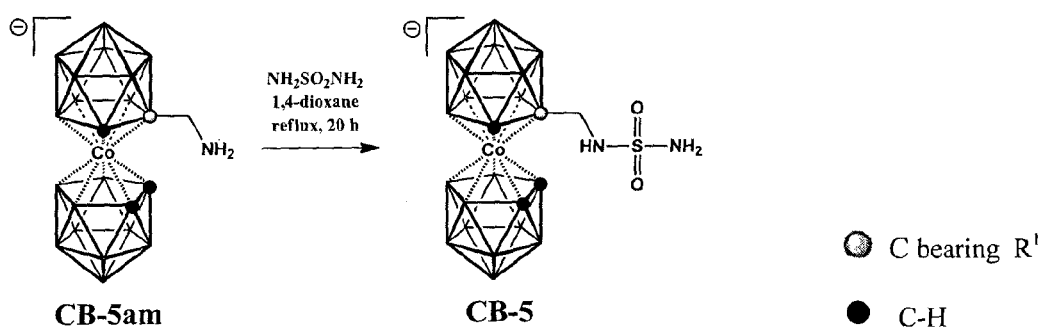

Structural formula of the compound CB-5 is depicted in FIG. 1. The preparative procedure leading to the compound CB-5 is shown in FIG. 6.

A mixture of the solid starting compound [(1-H$_3$N—CH$_2$-1,2-C$_2$B$_9$H$_{10}$)(1',2'-C$_2$B$_9$H$_{10}$)-3,3'-Co] (70 mg, 0.2 mmol) and sulfamide (95 mg, 0.98 mmol) was dried in a Schlenk-type flask for 8 h in vacuum at 50° C. Then 1,4-dioxane (15 ml) was added through a rubber septum and the reaction mixture was heated to reflux temperature under stirring and then heated for additional 20 h. After cooling down dioxane was evaporated under reduced pressure and resulting solid residue was extracted by mixture of CH$_2$Cl$_2$ and CH$_3$CN (3:1 b.v., 3×2 ml). Combined extracts were poured atop of silica gel column (20×1.5 cm) and eluted by CH$_2$Cl$_2$—CH$_3$CN solvent mixture with gradually increasing content of acetonitrile from 15% to 30% b.v. The first collected fraction contained unreacted starting ammonium derivative (15 mg). Other fractions corresponding to product (according to NMR and MS) were combined and evaporated under reduced pressure. The solid orange compound was dissolved in CH$_2$Cl$_2$ (5 ml) by addition of few drop of methanol, resulting solution was carefully layered with hexane and left to crystallize for 3 days. A semi-crystalline product separated, which was decanted, washed with a small amount of hexane and dried 8 h under educed pressure; yield of CB5: 45 mg (43%).

Found: $^1$H NMR (400 MHz; CD$_3$CN, Me$_4$Si) δ$_H$/ppm, 5.233 (2H, s, NHSO$_2$NH$_2$), 5.161 (1H, br, t, CH$_2$NHSO$_2$), 4.011, 3.933, 3.911 (3H, 3 br, s, CH$_{carborane}$), 3.857 (2H, d, J=6.8 Hz, —CH$_2$—NH), 3.557, 3.391 (2H, 2 s, B(8,8')H), 2.903 (2H, s, B(10,10')H); 2.709, 2.652, 2.585, 1.85 (8H, s, B(4,7,4',7',9,12, 9',12)H); 2.084 (8H, s, H$_2$O), 1.624 (1H, s, B(6)H), 1.624 (1H, s, B(6')H), 1.587 (1H, s, B(5)H), 1.554

(1H, s, B(11)H), 1.497 (2H, s, B(5',11')H); $^{11}$B NMR (128 MHz; CD$_3$CN; Et$_2$O,BF$_3$) $\delta_B$/ppm: 6.24 (2B, d, J=153 Hz, B8,8'), 0.988 (2B, d, J=143 Hz, B10,10'), −6.29, −6.86 (8B, 4 d, overlap, B4,7,4',7',9,12, 9',12'), −14.35, −16.97 (2B, 2 d, J=152 Hz, overlap, B5,11), −17.59 (2B, d, J=159 Hz, B5',11'), −20.53 (1B, d, J=171 Hz, B6), −22.72 (1B, d, J=171 Hz, B6'); $^{13}$C NMR (100 MHz; CD$_3$CN; Me$_4$Si) $\delta_C$/ppm: 66.47 (1C, s, C$_{carborane}$), 54.88 (1C, d, C$_{carborane}$), 52.72 (1C, d, C$_{carborane}$), 52.04 (1C, s, C$_{carborane}$), 51.05 (1C, m, CH$_2$NH); m/z (ESI) 432.38 (100%), 436.32 (4%), calcd.: 436.28 (100%), 432.29 (4%) [M−H]$^-$.

Example 6

7-methylensulfamide-8-phenyl-(7,8-nido-dikarbaun-dekabor)ate (1-), (compound CB-6)

Figure 7:
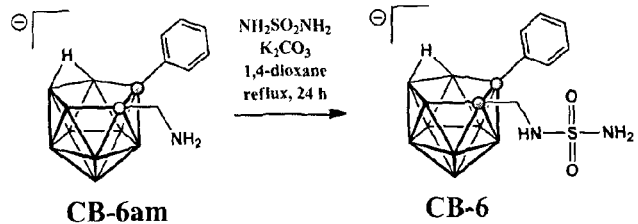

Structural formula of the compound CB-6 is depicted in FIG. 1. The preparative procedure leading to the compound CB-6 is shown in FIG. 7.

The starting 7-NH$_2$CH$_2$-8-C$_6$H$_5$-7,8-nido-C$_2$B$_9$H$_{13}$ (50 mg, 0.15 mmol) was dissolved in 1,4-dioxane (25 ml) and solid sulfamide (0.100 g, 1.04 mmol) was added under nitrogen followed with anhydrous K$_2$CO$_3$ (0.100 g, 0.73 mmol). Reaction mixture was heated up and stirred under reflux for 24 h. After cooling down the volatiles were removed in vacuum and the crude product was isolated by extraction of solids by acetonitrile (2×10 ml) and evaporation of the extracts. The pure compound was obtained by chromatography on a silica gel (20×1.5 cm I.D.) column. Yield: 47 mg (70%), colourless solid.

Found: $^1$H NMR (400 MHz; CD$_3$CN, Me$_4$Si) $\delta_H$/ppm: 7.184 (5H, m, C$_6$H$_5$), 5.26 (1H, t, CH$_2$NH), 3.31 (1H, s, B(9)H), 3.05 (2H, s, SO$_2$NH$_2$), 2.84 (2H, d, CH$_2$N), 2.32 (1H, s, B(11)H), 1.58 (1H, s, B(2)H), 1.55 (1H, s, B(3)H), 1.41 (1H, s, B(6)H), 1.30 (1H, s, B(5)H), 1.20 (1H, s, B(4)H), 0.58 (1H, s, B(1)H); 0.25 (1H, s, B(10)H), −2.22 (1H, br. s, B—H—B); $^{11}$B NMR (128 MHz; CD$_3$CN; Et$_2$O.B F$_3$) $\delta_B$/ppm: −8.62 (1B, d, J 164, B9), −10.59 (1B, d, J 131, B11), −14.11 (1B, d, J 156, B2), −16.63 (1B, d, J 150, B5), −17.94 (1B, d, J 143, B4), −18.91 (2B, d, J 143, B3,6), −33.54 (1B, d, J 92, B10), −36.72 (1B, d, J 137, B1), $^{13}$C NMR (100 MHz; CD$_3$CN; Me$_4$Si) $\delta_C$/ppm: 128.16 (4C, m, C$_6$H$_5$), 127.06 (2C, m, C$_6$H$_5$), 67.47 (1C, s, C(8)$_{carborane}$), 49.23 (1C, s, C(7)$_{carborane}$), 30.14 (1C, t, CH$_2$); m/z (ESI): 318.26 (100%), 320.24 (7%), [M−H]$^-$, calcd. 318.21 (100%), 320.21 (7%).

Example 7

1-methylenesulfamide-9-phenyl-1,2-dicarba-closo-dodecaborane and 1-methylene-sulfamide-12-phenyl-1,2-dicarba-closo-dodecaborane, ekvimolar mixture of both isomers, (compounds CB-8a and CB-8b)

Figure 8:
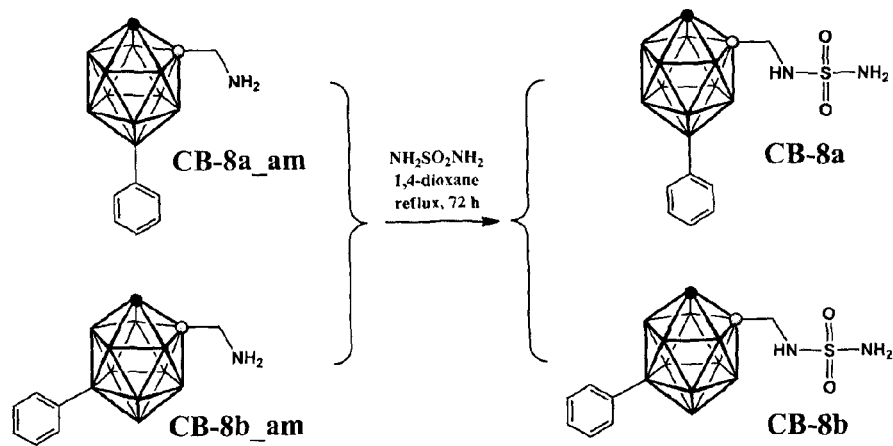

Structural formulae of the compound CB-8a and CB-8b are depicted in FIG. 1. The preparative procedure leading to the compound CB-8a and CB-8b is shown in FIG. 8.

Equimolar mixture (according to $^{11}$B NMR) of isomeric 1-NH$_2$CH$_2$-9-C$_6$H$_5$—C$_2$B$_{10}$H$_{10}$ and 1-NH$_2$CH$_2$-12-C$_6$H$_5$—C$_2$B$_{10}$H$_{10}$ was dissolved under nitrogen in dry 1,4-dioxane (10 ml). Solid, sulfamide (250 mg, 2.6 mmol) was added in one portion and the reaction mixture was refluxed for 72 h. After removal of the solvent in vacuum, ether was added (20 ml) to a semi-solid residue followed with water (10 ml) and diluted HCl (1 M, 20 ml). The ether layer was separated and the water phase was extracted by additional portions of ether (2×20 ml). Combined organic fraction were evaporated under reduced pressure and the residue was dissolved in a minimum volume mixture of CH$_2$Cl$_2$ and CH$_3$CN 95:5 b.v. injected atop of a silica gel column (20×1.5 cm I.D.) and the products were eluted increasing the acetonitrile content to 3:1. Chromatographic fractions corresponding to the product were collected; according to NMR, no separation of the two isomeric species occurred during the chromatography. The resulting solid was crystallized layering its concentrated solution with hexane and leaving to stand it for 3 days. The polycrystalline solid was decanted, washed with hexane and dried 6 h in vacuum; yield 85 mg (61%).

Found: $^1$H{$^{11}$B}NMR (400 MHz; Acetone-d$_6$, Me$_4$Si) $\delta_H$/ppm: 7.462 (2H, br. t, C$_6$H$_5$), 7.247 (2H, m, C$_6$H$_5$), 5.901 (1H, br. t, CH$_2$NHSO$_2$), 5.353 (2H, s, NHSO$_2$NH$_2$), 4.381 a 4,272 (1H, 2 br. s, CH$_{carborane}$), 3.77 (2H, 2 d, 0.7=7.6 Hz, —CH$_2$—NH), 2.744, 1.81 (1H, 2 s, B(9',12)H); 2.312 (2H, s, B(8,10)H), 2.304 (2H, 2 s, B(4,5)H), 2.420, 2.204 (4H, 2 s, B(8,11)H); $^{11}$B NMR (128 MHz; Acetone-d$_6$; Et$_2$O.B F$_3$) $\delta_B$/ppm: 7.29, 4.91 (1B, 2 s, B9,12'), −2.60, −5.29 (1B, 2 d, J=159 Hz, B9',12), −9.16 (2B, d, J=225 Hz, B8,10), −12.16 (2B, d, J=128 Hz, B4,5), −13.11 (4B, d, J=171 Hz, B3,6,7, 11); m/z (APCI$^+$, 5% aqueous K$_2$CO$_3$ was added to acetonitrile solution to improve ionization) 366.40 (100%), 369.38 (10%) [M+K]$^+$, calcd. 366.18 (100%), 369.17 (10%).

Examples 8 and 9

Isomeric 10-sulfamide-9'-amine-2,2'-commo-(1,7, 10-tricarba-1',7',9'-tricarba-2-ferra (II)-closo-dodekabor)ane and 9-sulfamide-10'-amine-2,2'-commo-(1,7, 9-tricarba-1',7', 10'-tricarba-2-ferra(H)-closo-dodekabor)ane, (compounds CB-10 and CB-11)

Figure 9:
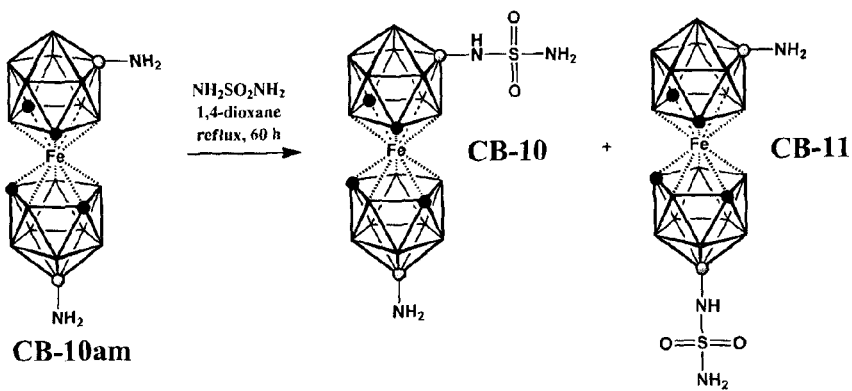

Structural formulae of the compound CB-10 and CB-11 are depicted in FIG. 1. The preparative procedure leading to the compound CB-10 and CB-11 is shown in FIG. 9.

The starting ferratricarbollide sandwich complex [(9-NH$_2$-1,7,9-C$_3$B$_8$H$_{11}$) (10-NH$_2$-1',7',10'-C$_3$B$_8$H$_{11}$)-2,2'-Fe] (CB-10am), prepared according to known procedure (Eur. J. Inorg. Chem.: 1402-1410, 2004), (100 mg, 0.28 mmol) was dissolved under nitrogen in dry 1,4-dioxane (8 ml), and solid sulfamide was added in one portion (270 mg, 2.8 mmol). The resulting slurry was heated and stirred under reflux temperature and then for additional 60 h. After cooling down, silica gel for column chromatography was added (Aldrich, 3 g) and dioxane was evaporated under reduced pressure. The silica gel containing a mixture of the products was poured atop of an chromatographic column (20×1.5 cm). Unreacted starting compound was then eluted with benzene and subsequent elution with ether-benzene mixture 1:1 b.v. led to separation of the two isomeric sulfamides CB10 a CB11, differing by the skeletal geometric position of the sulfamide group. Fractions 2 and 3, which according to TLC (ether-benzene 1:1 b.v.) and NMR corresponded to particular isomeric products were evaporated under reduced pressure and solid red compounds were dissolved in CH$_2$Cl$_2$ (1.5 ml) by addition of few drops of methanol. The resulting solutions were layered with hexane and left to crystallize for 3 days until separation of semi-crystalline compound occurred. The solid products were decanted, washed with small volume of hexane and dried 8 h under reduced pressure; yield Bylo of CB10 40 mg (33%) and CB11 12 mg (10%).

Found for CB-10: $^1$H{$^{11}$B}NMR (400 MHz; CD$_3$CN, Me$_4$Si) $\delta_H$/ppm, 6.275 (1H, s, CH$_2$NHSO$_2$), 5.395 ($^2$H, s, NHSO$_2$NH$_2$), 2.952 (2H, br, s, CH$_{carborane}$), 2.287 (2H, br, s, CH$_{carborane}$), 2.185 (2H, br, s, NH$_2$); 3.867 (2H, s, B(3,3')H), 3.827 (1H, s, B(9)H), 3.273 (2H, s, B(6,11)H), 2.967 (2H, s, B(6',11')H), 2.503, 2.340 (4H, 2 s, B(5,12,5',12")H), 2.153 (1H, s, B(10)H), 1.994, 1.530 (4H, 2 s, (B4,8,4',8')H); $^{11}$B NMR (128 MHz; CD$_3$CN; Et$_2$O.BF$_3$) $\delta_B$/ppm: −6.22 (2B, d, J=170 Hz, B6,11), −7.98 (2B, d, J=152 Hz, B6',11'), −9.81 (1B, d, overlap, B9), −11.90 (2B, d, J=165 Hz, B3,3'), −14.37, −15.07 (4B, 2 d, 166 and 174 Hz, B5,12, 5'12'), −16.04 (1B, d, J=126 Hz, B10'), −21.51, −23.17 (4B, 2 d, J=192 and 177 Hz, B4,8,4',8'); $^{13}$C NMR (100 MHz; CD$_3$CN; Me$_4$Si) $\delta_C$/ppm: 69.22 (1C, s, C$_{carborane}$), 43.58 (2C, d, C$_{carborane}$), 38.82 (2C, d, C$_{carborane}$), 30.14 (1C, s, C$_{carborane}$), m/z (APCI$^+$) 433.27 (100%), 435.26 (20%), calcd. 433.26 (100%), 435.25 (20%) [M+H]$^+$.

Found for CB-11: $^1$H{$^{11}$B}NMR (400 MHz; CD$_3$CN, Me$_4$Si) $\delta_H$/ppm, 5.547 (2H, s, NHSO$_2$NH$_2$), 5.428 (1H, s, CH$_2$NHSO$_2$), 3.865, 3.688 (2H, 2 s, B(3,3')H), 3.18 (2H, s, B(6',11')H), 2.986 (2H, s, B(6,11)H), 2.863 (1H, s, B(9')H), 2.492, 2.367 (4H, 2 s, B(5,12,5',12')H), 2.197 (2H, br, s, CH$_{carborane}$), 2.157 (2H, br, s, CH$_{carborane}$), 2.363 (2H, br, s, NH$_2$), 2.040 (1H, s, B(10)H), 1.459 (4H, s, (B4,8,4',8')H); $^{11}$B NMR (128 MHz; CD$_3$CN; Et$_2$O.BF$_3$) $\delta_B$/ppm: −5.60 (2B, d, J=168 Hz, B6',11'), −6.88 (1B, d, overlap, B9'), −8.22 (2B, d, J=152 Hz, B6,11), −12.26 (2B, d, J=163 Hz, B3,3'), −14.26, −14.92 (4B, 2 d, 167 and 186 Hz, B5,12, 5'12'), −17.66 (1B, d, J=165 Hz, B10), −22.77 (4B, d, J=162 Hz, B4,8,4',8'); $^{13}$C NMR (100 MHz; CD$_3$CN; Me$_4$Si) $\delta_C$/ppm: 78.41 (1C, s, C$_{carborane}$), 42.67 (2C, d, C$_{carborane}$), 39.88 (2C, d, C$_{carborane}$), 30.162 (1C, s, C$_{carborane}$), m/z (APCI$^+$) 433.33 (100%), 435.30 (20%), cald. 433.26 (100%), 435.25 (20%) [M+H]$^+$.

Example 10

9-sulfamide-9'-amine-2,2'-commo-bis(1,7,9-trikarba-2-ferra(II)-kloso-dodekabor)ane, (compound CB-12)

Figure 10:
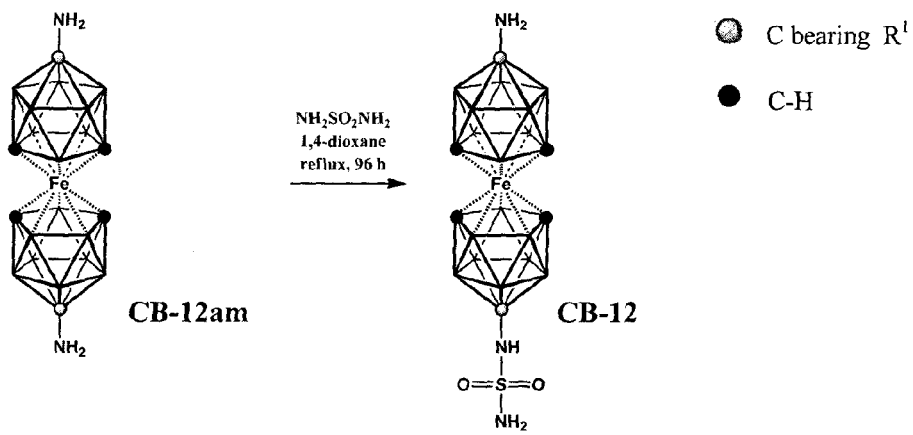

Structural formula of the compound CB-12 is depicted in FIG. 1. The preparative procedure leading to the compound CB-6 is shown in FIG. 10.

The starting ferratricarbollide complex [(9-NH$_2$-1,7,9-kloso-C$_3$B$_8$H$_{11}$)$_2$-2,2'-Fe], prepared according to known procedure (*Eur. J. Inorg. Chem.*: 1402-1410, 2004), (50 mg, 0.14 mmol) was reacted with sulfamide (150 mg) in dioxane under reflux for 96 h, analogously to the above described procedure for compounds CB10 and CB11. Product isolation was done also on a silica gel column (20×1,5 cm) using benzene and ether-benzene solvent mixture 1:1 b.b., followed by the product crystallization from dichloromethane-hexane. Yield CB12: 32 mg (52%).

Found: $^1$H{$^{11}$B}NMR (400 MHz; CD$_3$CN, Me$_4$Si) $\delta_H$/ppm: 6.757 (1H, s, CH$_2$NHSO$_2$), 5.510 (2H, s, NHSO$_2$NH$_2$), 4.067 (2H, s, B(3,3')H), 2.855 (4H, s, B(6,11, 6',11')H), 2.344, 2.22 (4H, 2 s, B(5,12,5',12")H), 2.179 (4H, br, s, CH$_{carborane}$), 1.964, 1.862 (1H, s, B(10,10')H), 2.169 (4H, 2 s, B(B4,8,4',8')H), 1.978 (2H, br, s, NH$_2$); $^{11}$B NMR (128 MHz; CD$_3$CN; Et$_2$O.BF$_3$) $\delta_B$/ppm: −8.07 (4B, d, J=153 Hz, B6,11,6',11'), −11.78 (2B, d, J=168 Hz, B3,3'), −15.02 (4B, d, J=183 Hz, B5,12,5',12'), −16.35, −17.92 (2B, 2 d, overlap and 186 Hz, B10,10'), −21.75, −22.60 (4B, 2 d, J=167 and 135 Hz, B4,8,4',8'); $^{13}$C NMR (100 MHz; CD$_3$CN; Me$_4$Si) $\delta_C$/ppm: 68.52 (1C, s, C$_{carborane}$), 42.68 (2C, d, C$_{carborane}$), 42.04 (2C, d, C$_{carborane}$), 39.41 (1C, S, C$_{carborane}$), m/z (ESI$^-$) 432.32 (100%), 434.30 (M−H$^-$, 20%), calcd. 432.26 (100%), 434.25 (20%) [M−H]$^-$.

Example 11

8-propylenesulfamide-7-phenyl-(7,8-nido-dicarbaundecabor)ate (1-), (compound CB-13)

Figure 11:
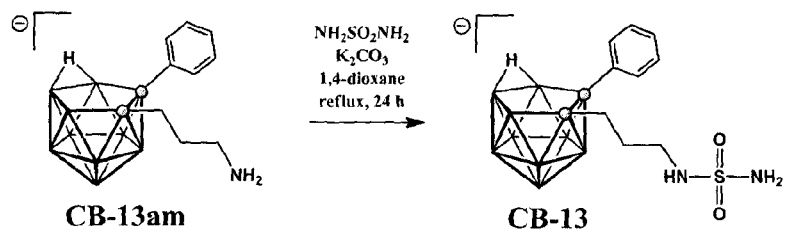

Structural formula of the compound. CB-13 is depicted in FIG. 1. The preparative procedure leading to the compound CB-13 is shown in FIG. 11.

A suspension was made from the starting 11-vertex 7-ammonium-propyl-8-fenyl-7,8-nido-dikarbaundekaborate (0.050 g, 0.14 mmol), sulfamide (0.055 g, 0.57 mmol) and K$_2$CO$_3$ (0.075 g, 0.54 mmol) in 1,4-dioxane (25 ml). Reaction mixture was stirred under reflux for 24 h. After cooling down, the volatiles were then removed under reduced pressure and the crude product was extracted into acetonitrile and purified on a silica gel column using CH$_2$Cl$_2$ and CH$_3$CN 4:1 b.v. as a mobile phase. Colourless solid; yield 0.058 g (77%).

Found: $^1$H{$^{11}$B}NMR (400 MHz; CD$_3$CN, Me$_4$Si) $\delta_H$/ppm: 7.70 (2H, d, C$_6$H$_5$), 7.45 (1H, d, C$_6$H$_5$), 7.32 (2H, d, C$_6$H$_5$), 5.22 (4H, s, NHSO$_2$NH$_3$), 2.73 (2H, m, CH$_2$N), 2.50 (2H, m, CH$_2$), 1.60 (2H, t, BCH$_2$), 2.74 (1H, s, B(4)H), 2.32 (1H, s, B(5)H), 2.25 (1H, s, B(9)H), 2.16 (1H, s, B(11)H), 2.00 (1H, s, B(6)H), 1.45 (1H, s, B(3)H), 1.19 (1H, s, B(2)H), 0.54 (1H, s, B(1)H), 0.07 (1H, s, B(10)H), −2.22 (1H, s, $^{11}$B NMR (128 MHz; CD$_3$CN; Et$_2$O.BF$_3$) $\delta_B$/ppm: −4.24 (1B, d, J 150, B9), −8.90 (1B, d, J 125, B11), −9.80 (1B, d, J 146, B5), −10.83 (1B, d, J 214, B4), −13.66 (1B, d, J 156, B6), −17.77 (1B, d, J 137, B2), −18.91 (1B, d, J 204, B3), −33.94 (1B, d, J 137, B10), −36.70 (1B, d, J 137, B1); $^{13}$C NMR (100 MHz; CD$_3$CN; Me$_4$Si) $\delta_C$/ppm: 132.05 (2C, d, C$_6$H$_5$), 129.91 (1C, d, C$_6$H$_5$), 127.91 (3C, m, C$_6$H$_5$), 44.16 (1C, s, C$_{carborane}$), 42.71 (1C, s, C$_{carborane}$), 33.82 (1C, t, NCH$_2$), 32.73 (1C, t, CH$_2$), 30.68 (1C, t, CH$_2$); m/z (ESI) 348.26 (10%), 346.28 (100%) [M]$^-$, calcd. 346.24 (10%), 346.24 (100%) [M−H]$^-$.

Example 12

8-ethylaminomethylsulfamide-8"-methoxy-3,3'-commo-bis(decahydro-1,2-dicarba-3-cobalta(III)-closo-dodecabor)ate (1-), (compound CB-15)

Figure 12:
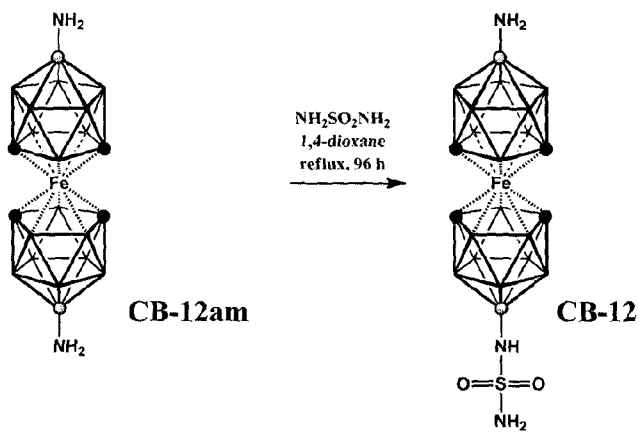

Structural formula of the compound CB-15 is depicted in FIG. 1. The preparative procedure leading to the compound CB-15 is shown in FIG. 12.

The zwitterionic derivative [μ-8-H$_2$NC$_2$H$_4$NH$_2$—CH$_2$-8"-CH$_3$O-(1,2-C$_2$B$_9$H$_{10}$)$_2$-3,3'-Co(III)] (50 mg, 0.12 mmol) was dissolved in 1,4-dioxane (5 ml). The, sulfamide H$_2$NSO$_2$NH$_2$ (112 mg, 1.17 mmol) was added under nitrogen and the resulting slurry was vigorously stirred and heated to reflux temperature and then for additional 2 h. The reaction course was followed using TLC (in CH$_3$CN—CH$_2$Cl$_2$, 1:3) and by MS and when the starting compound disappeared, the solvent was removed under reduced pressure. Dry solid was treated with 5 ml of acetonitrile and a resulting slurry was flittered. Then, solvent was evaporated under reduced pressure until dryness, orange solid orange material was dissolved in diethylether (10 ml) and shaken with diluted HCl (3M, 3×10 ml). The organic layer was separated and evaporated under reduced pressure. The crude product was dissolved in a solvent mixture containing 20 ml of CH$_2$Cl$_2$ and 2 ml of CH$_3$OH and the solution was layered with hexane (80 ml) and left to stand overnight. The solid pure product was was decanted from mother liquor; yield 38 mg (64%).

Found: $^1$H{$^{11}$B}NMR (400 MHz; CD$_3$CN, Me$_4$Si) $\delta_H$/ppm, 7.14 (2H, br, t, NH$_2$), 5.21 (4H, br, s, CH$_2$NH$_2$SO$_2$NH$_2$), 3.89 (2H, s, CH$_{carborane}$), 3.84 (2H, s, CH$_{carborane}$), 3.44 (3H, s, CH$_3$O), 3.27 (2H, q, CH$_2$NH$_2$), 3.13 (2H, p, CH$_2$NH$_2$), 2.98 (2H, t, B(8')H), 2.83 (1H, s, B(10)H), 2.82 (2H, s, B(4', 7")H), 2.72 (2H, s, B(4, 7)H), 2.61 (1H, s, B(10')H), 1.88 (2H, s, B(9, 12)H), 1.76 (2H, s, B(9', 12')H), 1.57 (1H, s, B(6)H), 1.57 (2H, s, B(5', 11')H), 1.54 (2H, s, B(5, 11)H), 1.41 (1H, s, B(6')H); $^{11}$B NMR (128 MHz; CD$_3$CN; Et$_2$O.BF$_3$) δ$_B$/ppm: 26.70 (1B, s, B8'), 9.98 (1B, s, B8), −0.20 (1B, d, J 146, B10), −2.48 (1B, d, J 143, B10'), −5.29 (2B, d, J 153, B9, 12), −6.52 (4B, d, J 162, B4, 7, 9', 12'), −8.16 (2B, d, J 208, B4', 7'), −18.18 (2B, d, J 143, B5, 11), −19.05 (2B, d, J 146, B5', 11'), −23.29 (1B, d, J 198, B6), −28.19 (1B, d, J 183, B6'); $^{13}$C NMR (100 MHz; CD$_3$CN; Me$_4$Si) δ$_C$/ppm: 58.15 (1C, t, CH$_2$), 51.50 (2C, d, CH$_{carborane}$), 50.32 (2C, t, CH$_2$N), 48.42 (2C, d, CH$_{carborane}$), 39.74 (1C, q, CH$_3$); m/z (ESI): 508.25 (15%), 505.25 (100%), calcd. 508.25 (15%) 505.34 (100%) [M−H]$^-$ Example 13

8-butyloxysulfamide-3,3'-commo-bis(decahydro-1,2-dicarba-3-cobalta(III)-closo-dodekabor)ate (1-), (compound CB-16)

Figure 13:
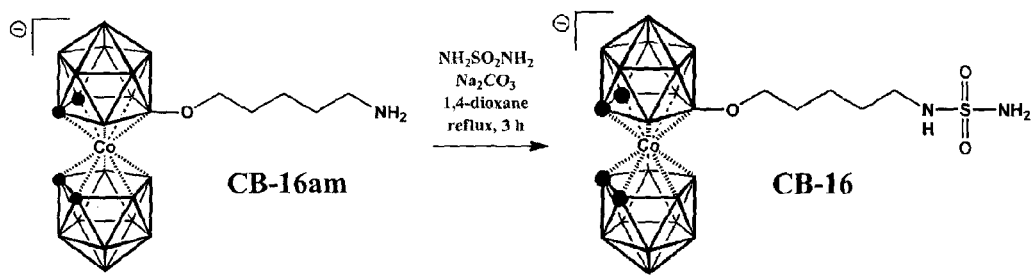

Structural formula of the compound CB-16 is depicted in FIG. 1. The preparative procedure leading to the compound CB-16 is shown in FIG. 13.

The starting ammonium derivative [8-H$_3$N—C$_4$H$_8$O-(1,2-C$_2$B$_9$H$_{10}$)(1',2'-C$_2$B$_9$H$_{11}$)-3,3'-Co(III)], prepared according to known procedure (e.g. *Dalton Trans.* 2008, 977-992), (102 mg, 0.24 mmol) was dissolved in 1,4-dioxane (5 ml). Solid sulfamide H$_2$NSO$_2$NH$_2$ (225 mg, 2.34 mmol), was added under nitrogen followed with anhydrous Na$_2$CO$_3$ (225 mg, 1.63 mmol) and the slurry was intensively stirred and heated under reflux temperature for 3 h. The reaction course was followed on TLC (in CH$_3$CN—CH$_2$Cl$_2$, 1:3) and by MS (ESI−) and when the starting compound disappeared the volatiles were removed under reduced pressure. The resulting solids were treated by acetonitrile (5 ml), the resulting slurry was filtered and filtrate was evaporated under reduced pressure to dryness. Solid residue was dissolved in ethylacetate (10 ml) and treated in extraction funnel with diluted HCl (3M 3×10 ml) to which saturated solution of NaCl (5 ml) was added for salting out of the product. The organic layer was separated and volatiles were removed in vacuum. The crude product was then dissolved in a solvent mixture comprising CH$_2$Cl$_2$ and CH$_3$OH (10:3 b.v., 26 ml). The solution was overlayered with hexane (80 ml) and left to stand for 3 d. Orange solid product was separated by decantation and dried in vacuum; yield 98 mg (82%).

Found: $^1$H NMR (400 MHz; CD$_3$CN, Me$_4$Si) δ$_H$/ppm: 4.10 (2H, s, CH$_{carborane}$), 3.98 (2H, s, CH$_{carborane}$), 3.51 (2H, t, CH$_2$O), 2.92 (2H, m, CH$_2$N), 2.82 (1H, s, B(10)H), 2.78 (1H, s, B(8')H), 2.65 (2H, s, B(9', 12')H), 2.61 (2H, s, B(9, 12)H), 2.58 (1H, s, B(10')H), 2.21 (4H, s, H$_2$NSO$_2$NH$_2$), 1.82 (2H, s, B(4, 7)H), 1.70 (2H, s, B(4', 7')H), 1.66 (1H, s, B(6')H); 1.62 (2H, m, CH$_2$), 1.55 (2H, s, B(5', 11')H), 1.48 (2H, s, B(5, 11)H), 1.43 (2H, m, CH$_2$), 1.41 (1H, s, B(6)H), 1.25 (2H, m, CH$_2$); $^{11}$B NMR (128 MHz; CD$_3$CN; Et$_2$O.BF$_3$) δ$_B$/ppm: 23.87 (1B, s, B8), 5.06 (1B, d, J 140, B8'), −0.29 (1B, d, J 140, B10), −2.88 (1B, d, J 150, B10'), −2.79 (2B, d, J 134, B9, 12), −5.12 (4B, d, J 147, B4, 7, 9', 12'), −6.31 (2B, d, J 192, B4', 7'), −7.48 (2B, d, J 150, B5, 11), −17.51 (2B, d, J 156, B5', 11'), −20.37 (1B, d, J 173, B6), −22.29 (1B, d, J 174, B6'), −28.81 (1B, d, J 143, B6); $^{13}$C NMR (100 MHz; CD$_3$CN; Me$_4$Si) δ$_C$/ppm: 69.31 (1C, t, CH$_2$O), 53.45 (1C, t, CH$_2$N), 47.43 (2C, d, CH$_{carborane}$), 40.93 (2C, d, CH$_{carborane}$), 31.22 (1C, t, CH$_2$), 26.94 (1C, t, CH$_2$), 23.30 (1C, t, CH$_2$); m/z (ESI) 508.33 (10%), 504.42 (100%), calcd 508.33 (10%), 50434 (100%) [M−H]$^-$.

Example 14

8-diethyleneoxysulfamide-3,3'-commo-bis(decahydro-1,2-dicarba-3-cobalta(III)-closo-dodekabor)ate (1-), (compound CB-17)

Figure 14:
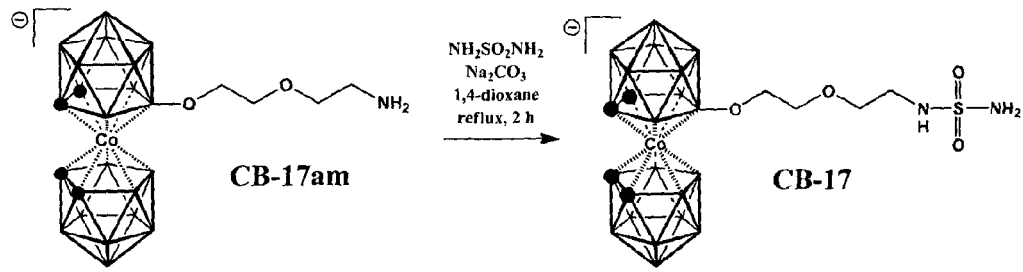

Structural formula of the compound CB-17 is depicted in FIG. 1. The preparative procedure leading to the compound CB-17 is shown in FIG. 14.

The known zwitterionic compound [8-H$_3$N—(C$_2$H$_4$O)$_2$-(1,2-C$_2$B$_9$H$_1$O$_2$-3,3'-Co(III)] (101 mg, 0.23 mmol), prepared however by the new procedure, was dissolved in 1,4-dioxane (5 ml) under nitrogen. Solid sulfamide H$_2$NSO$_2$NH$_2$ (224 mg, 2.33 mmol) was added followed by anhydrous Na$_2$CO$_3$ (246 mg, 2.32 mmol) and the slurry was then vigorously stirred and refluxed for 2 h. The reaction was periodically monitored by TLC (in CH$_3$CN—CH$_2$Cl$_2$, 1:3) and by MS ESI and evaporated under reduced pressure, when the starting derivative disappeared. The solids were treated by acetonitrile (5 ml), the resulting slurry was filtered and the filtrate was evaporated under reduced pressure. The orange solid was dissolved in diethylether (10 ml) and treated in an extraction funnel by diluted HCl (3M, 3×10 ml) and then by water (2×10 ml). The organic layer was separated and the crude was dissolved in a mixture of CH$_2$Cl$_2$ and CH$_3$OH (10:1 b.b., 22 ml) and the resulting solution was layered with hexane and left to crystallize overnight. The semi-solid product was decanted and dried in vacuum what resulted in an orange foamy-like solid. The mother liquors were evaporated as well; yield 110 mg (93%).

Found: $^1$H NMR (400 MHz; CD$_3$CN, Me$_4$Si) δ$_H$/ppm: 4.15 (2H, s, CH$_{carborane}$), 4.06 (2H, s, CH$_{carborane}$), 3.60 (2H, t, CH$_2$O), 3.53 (2H, t, CH$_2$O), 3.49 (2H, t, CH$_2$O), 3.14 (2H, m, CH$_2$N), 2.80 (1H, s, B(10)H), 2.77 (2H, s, B(4', 7')H), 2.66 (1H, s, B(8')H), 2.65 (2H, s, B(4, 7)H), 2.58 (2H, s, B(9, 12)H), 2.57 (1H, s, B(10')H), 2.27 (5H, s, NH$_2$SO$_2$NH$_3$), 1.67 (2H, s, B(9', 12')H), 1.63 (1H, s, B(6')H), 1.54 (2H, s, B(5', 11')H), 1.45 (2H, s, B(5, 11)H), 1.38 (1H, s, B(6)H); $^{11}$B NMR (128 MHz; CD$_3$CN; Et$_2$O.BF$_3$) δ$_B$/ppm: 23.67 (1B, s, B8), 4.77 (1B, d, J 140, B8'), −0.11 (1B, d, J 140, B10), −2.72 (1B, d, J 143, B10'), −5.05 (2B, d, J 153, B4, 7), −7.62 (4B, d, J 146, B9, 12, 9', 12'), −9.07 (2B, d, J 186, B4', 7'), −17.49 (2B, d, J 153, B5, 11), −20.49 (2B, d, J 156, B5', 11'), −22.36 (1B, d, J 167, B6), −28.62 (1B, d, J 168, B6'); $^{13}$C NMR (100 MHz; CD$_3$CN; Me$_4$Si) δ$_C$/ppm: 72.42 (1C, t, CH$_2$O), 70.45 (1C, t, CH$_2$O), 69.19 (1C, t, CH$_2$O), 53.98 (2C, d, CH$_{carborane}$), 47.53 (2C, d, CH$_{carborane}$), 43.98 (1C, t, CH$_2$N); m/z (ESI): 506.42 (100%), 509.33 (14%), calcd. 506.32 (100%), 509.33 (14%)

Example 15

1-methylenesulfamide-1,7-dicarba-closo-dodecaborane, (compound CB-19)

Figure 15:
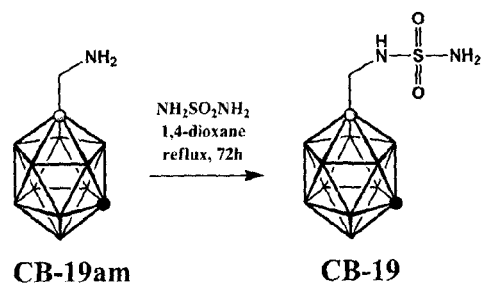

Structural formula of the compound CB-19 is depicted in FIG. 1. The preparative procedure leading to the compound CB-19 is shown in FIG. 15.

1-methyleneamino-1,7-dicarbaborane 1-NH$_2$CH$_2$—C$_2$B$_{10}$H$_{11}$ (65 mg, 0.38 mmol), prepared by known procedure (*Dalton Transactions* 2004: 3669-3677) was dissolved in was dissolved in 1,4-dioxane (10 ml) and dry sulfamide (187 mg, 2.0 mmol) was added and the slurry was stirred under reflux for 72 h. After cooling down, the volatiles were removed in vacuum, water was added (10 ml) and the crude product was extracted into diethylether (3×10 ml), the combined extracts were shaken with diluted hydrochloric acid (3 M, 3×10 ml), washed with water (3×10 ml) and evaporated. The solid was dissolved in ether, injected atop a silica gel column (20×1.5 cm I.D.) and eluted with benzene-ether 1:1 a then with ether. Ether fractions containing the product (according to NMR) were combined, evaporated to dryness and dried 6 h in vacuum. Yield 50 mg (53%).

Found: $^1$H NMR (400 MHz; Aceton-$d_6$, Me$_4$Si) $\delta_H$/ppm: 6.44 (1H, br, t, CH$_2$NHSO$_2$), 6.08 (2H, s, NHSO$_2$NH$_2$), 3.78 (1H, br, s, CH$_{carborane}$), 3.53 (2H, d, J=7.6 Hz, CH$_2$—NH), 2.86 (2H, s, B2,3-H); 2.38 (1H, s, B5-H), 2.27 (1H, s, B12-H), 2.271, 2.09 (4H, 2 s, B4,6,9,10-H), 2.15 (1H, s, B8,11-H); $^{11}$B NMR (128 MHz; Acetone-$d_6$; Et$_2$O.BF$_3$) $\delta_B$/ppm: −4.50 (1B, d, J=159 Hz, B5), −9.40 (1B, d, J=225 Hz, B12), −11.13 (4B, d, J=128 Hz, B4,6,9,10), −13.40 (2B, d, J=171 Hz, B8,11), −15.30 (2B, d, J=183 Hz, B2,3); $^{13}$C NMR (100 MHz; Acetone-$d_6$; Me$_4$Si) $\delta_C$/ppm: 77.45 (1C, s, C$_{carborane}$), 56.72 (IC, d, CH$_{carborane}$), 48.24 (1C, t, CH$_2$); m/z (APCI$^-$) 254.08 (5%), 251.08 (100%), calcd. 254.19 (5%), 251.19 (100%) [M−H]$^-$.

Příklad 16

Di(methylenesulfamide)-1,7-dicarba-closo-dodecaborane, (compound CB-20)

Figure 16:
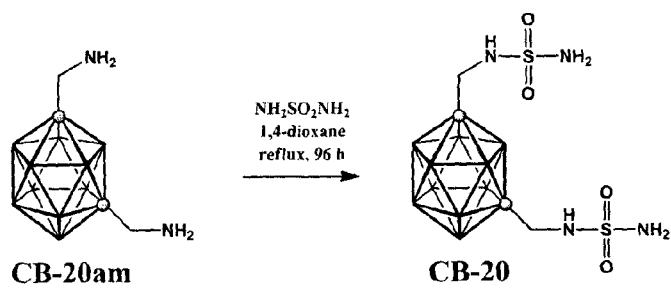

Structural formula of the compound CB-20 is depicted in FIG. 1. The preparative procedure leading to the compound CB-20 is shown in FIG. 16.

1,7-di(methyleneamine)-1,7-dicarbaborane 1,7-(NH$_2$CH$_2$)$_2$—C$_2$B$_{10}$H$_{10}$ (105 mg, 0.51 mmol), prepared according to the reported procedure (*Dalton Transactions* 2004: 3669-3677) was dissolved in 1,4-dioxane (10 ml) and reacted with sulfamide (250 mg, 2.6 mmol) under nitrogen at reflux temperature during 4 days under intensive stirring. After cooling down and removal of volatiles under reduced pressure the crude product was extracted into acetonitrile (3×10 ml) and combined extracts were evaporated in vacuum. The product was purified by chromatography on a silica gel column (20×1,5 cm I.D.) using benzene-ether 1:1 b.v. and then ether-CH$_3$CN solvent mixture 4:1 b.v. as the mobile phase. Ether-acetonitrile fractions containing the product (according to NMR) were combined, evaporated to dryness and dried 6 h in vacuum. The product was further crystallized from ether-hexane. Yield 75 mg (40%).

Found: $^1$H NMR (400 MHz; CD$_3$CN, Me$_4$Si) $\delta_H$/ppm: 5.63 (1H, br, t, CH$_2$NHSO$_2$), 5.23 (2H, s, NHSO$_2$NH$_2$), 3.38 (2H, d, J=7.6 Hz, —CH$_2$—NH), 2.88 (2H, s, B2,3-H); 2.20 (4H, 2 s, B4,6,9,10-H), 2.19 (2H, s, B5,12-H), 1.992 (1H, s, B8,11-H); $^{11}$B NMR (128 MHz; CD$_3$CN; Et$_2$O.BF$_3$) ($\delta_B$/ppm: −7.15 (2B, d, J=162, B5,12), −11.47 (6B, d, J=155, B4,6,9,10,8,11), −14.26 (2B, d, J=180, B2,3); $^{13}$C NMR (100 MHz; CD$_3$CN; Me$_4$Si) $\delta_C$/ppm: 76.34 (2C, S, C$_{carborane}$), 47.83 (2C, t, CH$_2$); m/z (APCI$^-$) 362.17 (5%), 359.33 (100%), calcd. 362.18 (5%), 359.18 (100%) [M−H]$^-$.

Example 17

Synthesis of the reactive brigre derivative [8,8'-µ-(CH$_2$O(CH$_3$))-(1,2-C$_2$B$_9$H$_{10}$)$_2$-3-Co], (compound CB-4-Pre, the intermediate in the preparation of CB-4)

Figure 2:
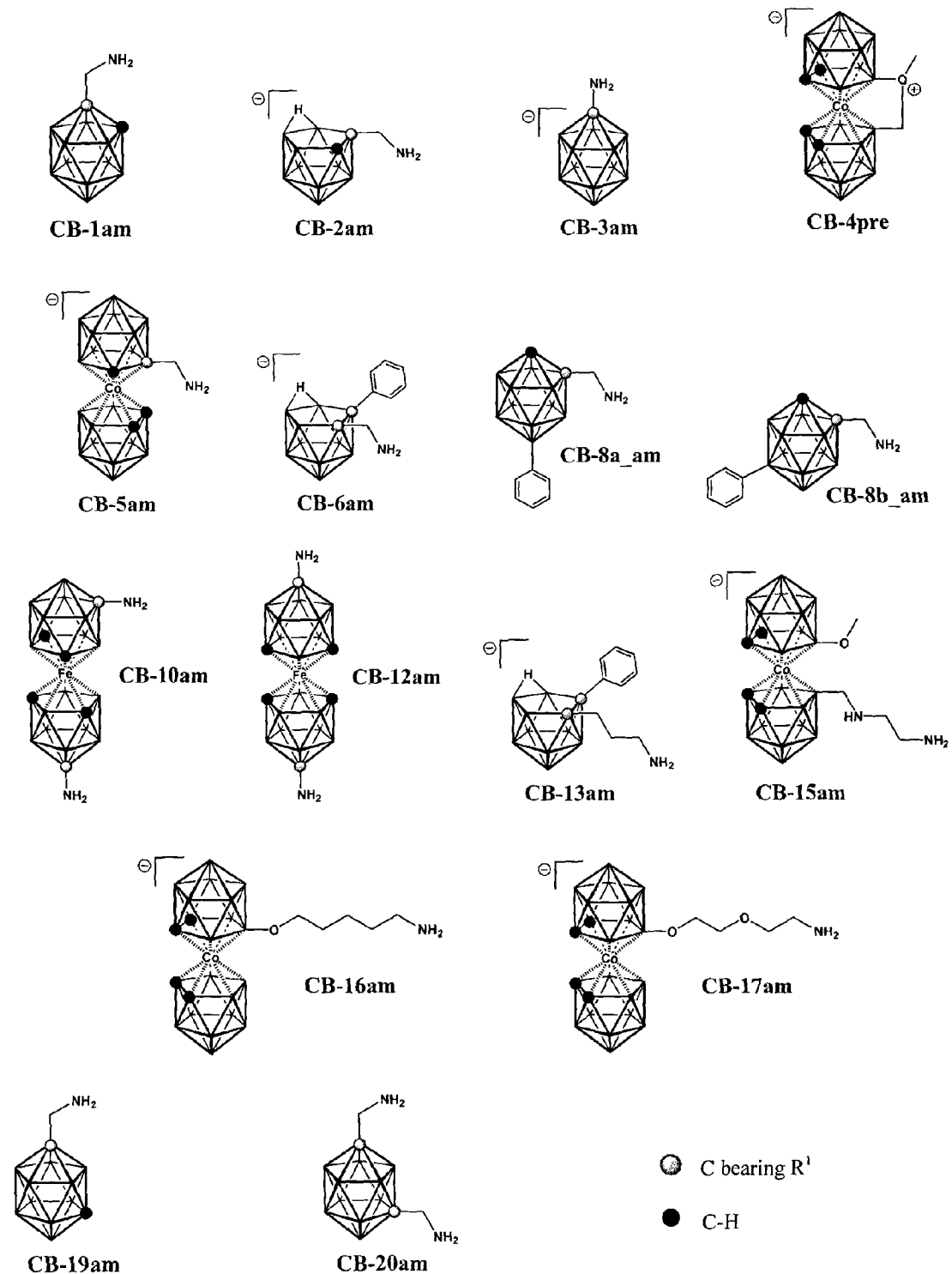
Figure 17:
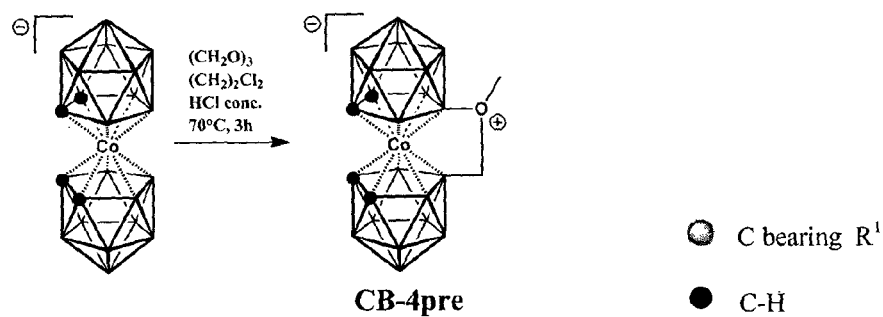

Structural formula of the compound CB-4-Pre is depicted in FIG. 2. The preparative procedure leading to the compound CB-4-Pre is shown in FIG. 17.

To a slurry of Cs$^+$ (or other salt with suitable cation, e.g. Rb$^+$, K$^+$) salt of cobalt bis(dicarbollide) (Katchem, s.r.o., Praha) (2.29 g, 5 mmol) in 1,2-dichloroethane (10 ml) stirred under nitrogen, HCl (35% v.v., 5 ml, 60 mmol) was added followed with byl paraformaldehyde (0.6 g, 20 mmol) and the reaction mixture was heated up to 60° C. (bath temperature) and kept at this temperature for additional 2 h. After cooling down and standing for 2 h, a solid which precipitated out and contained side products was filtered out and washed with 1,2-dichloroethane (2×10 ml). Filtrate was transferred into an extraction and extracted by water (20 ml), then with 5% aqueous Na$_2$CO$_3$ (3×10 ml), water (3×10 ml) and then the organic layer was separated and evaporated to dryness under reduced pressure. This procedure led to isolation of a mixture of two electroneutral species in 1.28 g (70% yield), containing small amount of other compounds (up to 5%). Yellow compound with formula [8,8'-µ-(CH$_2$O(CH$_3$))-(1,2-C$_2$B$_9$H$_{10}$)$_2$-3-Co] can be isolated from the above mixture of zwitterionic products in pure form by chromatography on a silica gel column (2.5×30 cm) using mixture of hexane and acetone 5:1 b.v., isolatable yield 0.39 g, 21%. Alternatively, the mixture of both compounds can be reacted with sulfamide and the pure product CB-4 can be then separated by liquid chromatography on silica gel.

Found for [(8,8'-µ-(CH$_3$OCH$_2$)-(1,2-C$_2$B$_9$H$_{10}$)$_2$-3,3'-Co]$^0$: HPLC purity: 98.4%; R$_f$(CH$_2$Cl$_2$:hexan 3:1) 0.71; $^1$H NMR $\delta_H$ (400 MHz, CD$_3$COCD$_3$, Me$_4$Si): 4.967 (br. s, 2H, CH$_2$), 4.244 (s, 2H, CH$_{carborane}$), 4.208 (s, 3H, CH$_3$O); 3.975 (s, 2H, CH$_{carborane}$); $^{11}$B NMR (128 MHz, CD$_3$COCD$_3$, Et$_2$O.BF$_3$): 30.70 (s, 1B), 13.01 (s, 1B), 0.67 (d, 1B, J=143 Hz), −3.64 (d, 1B, překryv), −5.44 (d, 4B, J=144), −8.82 (d, 4B, =143 Hz), −14.43 (d, 2B, J=159 Hz), −16.77 (d, 2B, J=158 Hz), −23.78 (d, 1B, J=171 Hz), −28.53 (d, 1B, J=174 Hz); $^{13}$C NMR: $\delta_C${$^1$H}(100 MHz, CD$_3$CN, Me$_4$Si): 98.77 (CH$_2$) 72.90 (CH$_3$O), 51.74, 46.99 (CH$_{carborane}$); m/z (APCI$^-$) 366.78 (100%), 370.29 (4%), calcd. 366.78 (100%), 370.29 (4%) [M]$^-$.

Example 18

1-methyleneammonio-3,3'-commo-bis(decahydro-1,2-dicarba-3-cobalta(III)-closo-dodecabor)ate (1−), [(1-H$_3$N—CH$_2$-1,2-C$_2$B$_9$H$_{10}$)(1',2'-C$_2$B$_9$H$_{11}$)-3,3'-Co], (compound CB-5am, the intermediate in the preparation of compound CB-5)

Figure 18:
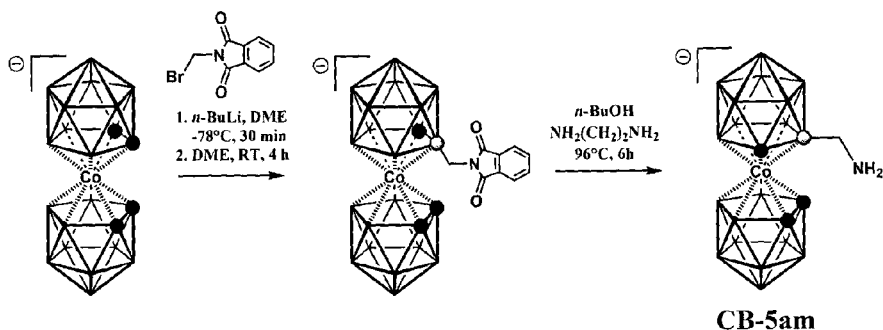

Structural formula of the compound CB-5am is depicted in FIG. 2. The preparative procedure leading to the compound CB-5am is shown in FIG. 18.

Dried caesium salt of cobalt bis(dikarbollide) (Katchem, s.r.o., Praha) 2.71 g (5.9 mmol) was dissolved under argon in ethyleneglycol dimethylether (DME, 40 ml), and cooled down to −78° C. (bath temperature), and then BuLi (4.0 ml BuLi, 1.6 M in hexane; 6.4 mmol) was added from syringe under vigorous stirring. After stirring for 15 min. at low temperature, the flask was left to warm up to room temperature and then cooled down again. Solution of brommethylftalimide (1.50 g, 6.2 mmol) in 15 ml of DME was then slowly added from syringe over 15 min. at −78° C. and the reaction mixture was left to warm up to room temperature over 4 h period. After standing overnight, the solids were filtered under argon, washed with DME (2×10 ml) and a red combined filtrate was evaporated in vacuum. Solid residue was dissolved in CH$_2$Cl$_2$—CH$_3$CN mixture (85:15, b.v.) and injected atom of a silica gel column (2.5×25 cm). Elution using mobile phase of the same composition led to recovery of an orange band containing the starting compound (780 mg). Subsequent elution with the same mixture of solvents in the ration 3:1 to 1:1 b.v. followed by evaporation of volatiles under reduced pressure led to isolation of 1.93 g of red intermediate of the formula [(1-$C_6H_4$—(CO)$_2$—N—$CH_2$-1,2-$C_2B_9H_{10}$)(1',2'-$C_2B_9H_{10}$)-3,3'-Co]Li, according to NMR and MS.

500 mg (1.04 mmol) of the above intermediate was dissolved in 10 ml of n-butanol, ethylendiamine (1.0 ml) was added and the reaction mixture was heated and stirred at 95° C. under nitrogen for 6 h. After cooling down, the volatiles were removed under reduced pressure (heated in a bath at temperature 80° C.). The residue was dissolved in ether, washed with diluted HCl (3 M, 3×30 ml), the organic phase was washed with water and evaporated to dryness. The product was separated from the parent complex, which results from the reaction as side product by chromatography on silica gel using solvent mixture $CH_2Cl_2$—$CH_3CN$ (4:1, b.v.); yield 110 mg (30%).

Found: $^1$H NMR (400 MHz; $CD_3CN$, Me$_4$Si) $\delta_H$/ppm, 4.322 (1H, d, J=14.4 Hz, $CH_2NH_2$), 4.069, 4.030, 3.884 (3H, 3 br.s, CH$_{carborane}$), 3.822 (1H, d, J=14.4 Hz, —$CH_2$—NH), 3.501, 3.258 (2H, 2 s, B(8,8')H), 2.979, 2.918 (2H, 2 s, B(10, 10')H); 2.841, 1.828, 1.811 (8H, s, B(4,7,4',7',9,12, 9',12')H); 1.645 (1H, Is, B(6')H), 1.592 (1H, s, B(6')H), 1.595, 1.592 (4H, 5 s, B(5, 11, 5',11')H); $^{11}$B NMR (128 MHz; $CD_3CN$; Et$_2$O.BF$_3$) $\delta_B$/ppm: 7.05 (2B, d, J=144 Hz, B8,8'), 2.13, 0.774 (2B, 2 d, J=159 a158 Hz, B10,10'), −5.60, −6.55, −4.22 (8B, 3 d, overlap, B4,7,4',7',9,12, 9',12'), −16.92 (4B, d, J=162 Hz, B5,11, 5',11'), −21.51 (1B, d, J=147 Hz, B6), −22.63 (1B, d, J=159 Hz, B6'); $^{13}$C NMR (100 MHz; $CD_3CN$; Me$_4$Si) $\delta_C$/ppm: 66.65 (1C, s, C$_{carborane}$), 53.85 (1C, d, C$_{carborane}$), 52.05 (1C, d, C$_{carborane}$), 51.81 (1C, s, C$_{carborane}$), 38.22 (1C, q, $CH_2NH$); m/z (ESI$^-$) 353.42 (100%), 356.42 (10%), calcd: 353.31 (100%), 356.30 (10%) [M−H]$^-$.

Example 19

7-aminomethyl-8-fenyl-(7,8-nido-dikarbaundekabor)ate (1-), (compound CB-6am, the intermediate in the preparation of compound CB-6)

Figure 19:
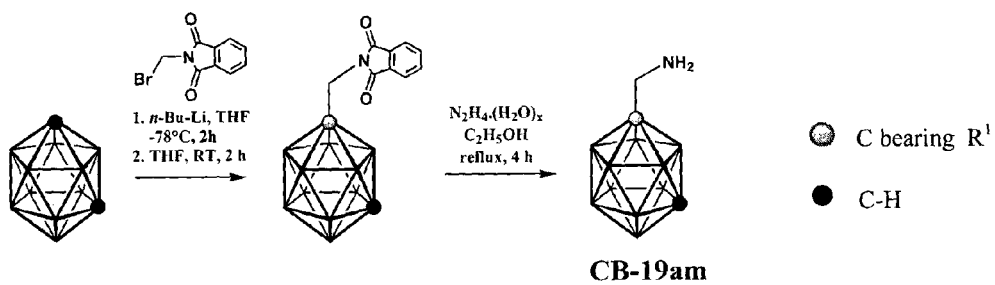

Structural formula of the compound CB-6am is depicted in FIG. 2. The preparative procedure leading to the compound CB-6am is shown in FIG. 19.

The starting carborane, 1-$C_6H_5$-1,2-$C_2B_{10}H_{11}$ 1.00 g (4.53 mmol) dried in vacuum, was dissolved in DME (40 ml) in Schlenk-type flask under argon, and the resulting solution was cooled down to −33° C. and BuLi (2.5 M in hexane, Aldrich, 2.0 ml, 5.0 mmol) was added under stirring from a syringe through septum. The reaction slurry was stirred for 15 min. and then left to warm up to room temperature. The reaction mixture was again cooled down and bromomethyl phtalimide 1.20 g (Aldrich, 5.0 mmol) dissolved in v 15 ml of DME was added dropwise from a syringe. The reaction mixture was stirred for 15 min. −33° C. at and then left slowly to warm up to room temperature over 4 h period. After standing overnight, the solids were filtered off under argon, and washed under argon with two portions of DME (10 ml). Diluted acetic acid (3 M, 0.5 ml) was added to the combined DME extracts and volatiles were removed under reduced pressure. A solid residue was dissolved in benzene and poured atop of a silica gel column (3×25 cm). Elution with benzene led to isolation of the starting 1-Ph-carborane (240 mg), continued elution using benzene-$CH_3CN$ (4:1, b.v.) solvent mixture afforded the methylene-phtalimide substituted intermediate carborane 0.85 g (49%).

To a part of the above intermediate derivative (160 mg, 0.42 mmol) was dissolved in aqueous ethanol (80%, 20 ml) hydrazine hydrate (2.0 ml, 4.12 mmol, Aldrich) was added. The reaction mixture was then stirred at room temperature for 16 h. The crude product was extracted from a mixture of solids into ether, ether was evaporated under reduced pressure and the product was dried in vacuum; yield 78 mg (78%).

Found: TLC ($CH_3CN$:$CH_2Cl_2$, 1:3) $R_F$=0.33; $^1$H NMR (400 MHz; $CD_3CN$, Me$_4$Si) $\delta_H$/ppm: 7.35 (5H, m, $C_6H_5$), 4.11 (3H, t, $CNH_3$), 2.67 (2H, q, $CH_2N$), 2.06 (1H, s, B(11)H), 2.05 (1H, s, B(9)H), 2.02 (1H, s, B(2)H), 1.61 (1H, s, B(4)H), 1.40 (1H, s, B(5)H), 1.33 (1H, s, B(6)H), 1.17 (1H, s, B(3)H), 0.66 (1H, s, B(1)H), 0.22 (1H, s, B(10)H), −2.17 (1H, s, B—H—B); $^{11}$B NMR (128 MHz; $CD_3CN$; Et$_2$O.BF$_3$) $\delta_B$/ppm: −8.76 (1B, d, J 140, B9), −10.45 (1B, d, J 134, B11), −14.23 (1B, d, J 147, B2), −15.15 (1B, d, J 125, B5), −18.51 (2B, d, J 143, B3, 4), −20.13 (1B, d, J 195, B6), −33.09 (1B, d, J 92, B10), −36.25 (1B, d, J 140, B1), $^{13}$C NMR (100 MHz; $CD_3CN$; Me$_4$Si) $\delta_C$/ppm: 128.13 (4C, $C_6H_5$), 127.10 (2C, $C_6H_5$), 67.45 (1C, C$_{carborane}$), 49.19 (1C, C$_{carborane}$), 30.17 (1C, $CH_2$); m/z (ESI) 241.17 (7%), 238.25 (100%), calcd. 238.24 (100%) [M−H]$^-$.

Example 20

1-methyleneamino-12-phenyl-1,2-dicarba-closo-dodecaborane and 1-methyleneamine-9-phenyl-1,2-dicarba-closo-dodecaborane, (compound CB-8am, the intermediate for the preparation of CB-8)

Figure 20:
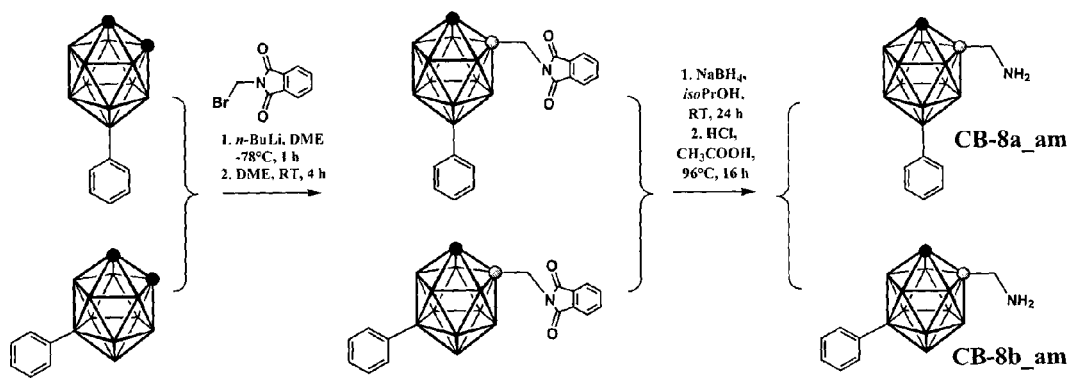

Structural formula of the compound CB-7am is depicted in FIG. 2. The preparative procedure leading to the compound CB-6am is shown in FIG. 20.

The starting 9-phenyl-1,2-carborane 1.29 g (5.9 mmol) dried in vacuum was dissolved under argon in DME (40 ml) in a flask of Schlenk type and the solution was cooled down to −78° C. (bath temperature) and BuLi (1.6 M in hexane, Aldrich), 3.9 ml (6.2 mmol) was added under stirring. The content of the flask was stirred for 15 min. and the reaction mixture was left to warm up slowly to room temperature and then cooled again. Then solution of bromomethyl phtalimide 1.50 g (6.2 mmol) in 15 ml DME was dropwise during 30 min. and the reaction mixture was stirred for additional 15 min. at −78° C. and then left to warm slowly up to ambient temperature during 4 h. After standing overnight the solids were removed by filtration under argon, washed with DME (2×10 ml), and few drops of diluted acetic acid were added (3 M, 0.5 ml). The volatiles were then removed under reduced pressure. A solid residue was dissolved in minimum volume of benzene and this solution was injected atop of a silica gel column (3×25 cm I.D.). Elution with benzene led to isolation of unreacted starting carborane (530 mg); continuing of the elution with benzene-$CH_3CN$ (95:5 b.v.) led to isolation of the intermediate product substituted by methylene phtalimide group, after removal of the solvent in vacuum and drying; yield 1.01 g. A part of this compound (330 mg) was reduced in 2-propanol (25 ml) and water (5 ml) mixture by $NaBH_4$ (1.3 g) and the reaction mixture was stirred for 24 h at room temperature. Volatiles were then removed under reduced pressure and methanol and several drops of diluted HCl (3 M) were added three times and solvents were evaporated to dryness. Concentrated acetic acid (25 ml) and HCl (35%, 2.5 ml) were added and the resulting solution was heated for 16 h at 96° C. (bath temperature). The volatiles were then removed under reduced pressure, water (20 ml) was added and the crude product was extracted into ether (3×20 ml). Combined ether extracts were evaporated under reduced pressure and the unseparable mixture of both isomers was purified by chromatography on a silica gel column (25×1.5 cm I.D.) from the rest of uncleaved by-product and organic impurities using $CH_2Cl_2$—$CH_3CN$ mixture (95:5 to 3:1) as the mobile phase. Fractions corresponding to product were collected, evaporated and crystallized from $CH_2Cl_2$ (with a drop of MeOH for dissolution) by layering with hexane. The product in form of white semi-crystalline solid was obtained by evaporation the mother liquors under reduced pressure; yield 125 mg (58%).

Found $^1$H NMR (400 MHz; $CD_3CN$, $Me_4Si$) $\delta_H$/ppm: 7.417 (2H, br. t, $C_6H_5$), 7.209 (3H, m, $C_6H_5$), 4.338 (2H, 2 br. d, $NH_2$), 4.420 a 4.304 (1H, 2 br. 5, $CH_{carborane}$), 3.347 (2H, d, J=6.0 Hz, $-CH_2-NH$), 2.465, 1.80 (1H, 2 s, B(9',12)H); 2.312 (2H, s, B(8,10)H), 2.273 (2H, s, B(3,6)H), 2.271 (2H, 2 s, B(4,5)H), 2.312, 2.112 (4H, 2 s, B(8,11)H); $^{11}$B NMR (128 MHz; $CD_3CN$; $Et_2O.BF_3$) $\delta_B$/ppm: 6.60, 4.25 (1B, 2 s, B9,12'), −3.25, −5.93 (1B, 2 d, J=143, 150 Hz, B9',12), −9.12 (2B, d, J=146 Hz, B8,10), −11.90, −12.31 (2B, 2 d, overlap., B4,5), −13.47 (4B, d, J=167 Hz, B3,6,7,11); ink (APCI$^+$): 250.42 (100%), 253.33 (4%), calcd. 250.26 (100%), 253.26 (4%) [M+K]$^+$.

Example 21

8-propylammonio-7-phenyl-(7,8-nido-dicarbaundecabor)ate (1-), (compound CB-13am, the intermediate for the preparation of CB-13)

Figure 21:
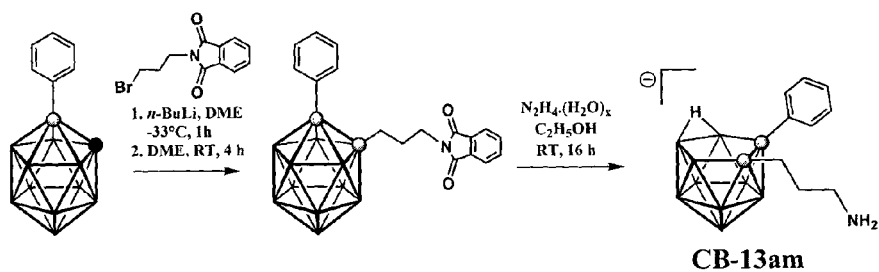

Structural formula of the compound CB-13am is depicted in FIG. 2. The preparative procedure leading to the compound CB-13am is shown in FIG. 21.

Dried $C_6H_5$-closo-1,2-$C_2B_{10}H_{12}$ 2.00 g (9.06 mmol) was dissolved in DME (40 ml) under argon, the solution was then cooled down to −33° C. and BuLi (2.5 M in hexane, 4.0 ml, 10.0 mmol) was added dropwise from a syringe. The reaction mixture was stirred for additional 15 min., then left to warm up to room temperature and cooled down again to −33° C., solution of bromopropyl phtalimide in DME (15 ml) was added slowly, reaction mixture was then kept at low temperature for 15 min. and then left to warm slowly under stirring to room temperature over 4 h and left to stand overnight. Solids were removed by filtration under argon and washed with DME (2×10 ml). Diluted acetic acid (3 M, 0.5 ml) was added to filtrate and the volatiles were removed in vacuum. Solids were dissolved in benzene and the injected atop of a silica gel column (25×3 cm I.D.). The unreacted starting compound (440 mg, 22%) was eluted by benzene, whereas the propyl phtalimide intermediate was isolated by elution with benzene-$CH_3CN$ (95:5) and evaporated to dryness; yield 1.95 g (53%).

The propyl phtalimide derivative 500 mg (1.23 mmol) was dissolved in aqueous ethanol (80%, 50 ml) and treated under stirring with hydrazine hydrate in excess (0.7 ml, 14.4 mmol, Aldrich) 16 h at room temperature and then 4 h under reflux. After cooling down, the volatiles were removed under reduced pressure. Crude product was extracted into ethyl ether from the solid residue. Combined ether extracts were evaporated under reduced pressure, yielding colorless solid (226 mg; 69%).

Found: $R_f$ ($CH_3CN:CH_2Cl_2$ (1:3) 0.17; $^1H\{^{11}B\}$NMR (400 MHz; $CD_3CN$, $Me_4Si$) $\delta_H$/ppm: 7.70 (2H, d, Ph), 7.45 (1H, d, Ph), 7.32 (2H, d, Ph), 3.88 (3H, t, $NH_3$), 2.42 (2H, m, $CH_2N$), 2.15 (1H, s, B(11)H), 2.00 (1H, s, B(9)H), 1.99 (1H, s, B(2)H), 1.92 (2H, p, $CH_2$), 1.50 (2H, s, B(3, 6)H), 1.49 (2H, t, $CH_2$), 1.21 (1H, s, B(4)H), 1.21 (1H, s, B(5)H), 0.55 (1H, s, B(1)H), 0.10 (1H, s, B(10)H), −2.25 (1H, s, B—H—B); $^{11}$B NMR (128 MHz; $CD_3CN$; $Et_2O.BF_3$) $\delta_B$/ppm: −8.95 (1B, d, J 134, B9), −10.83 (1B, d, J 140, B11), −13.61 (1B, d, J 156, B2), −17.34 (1B, d, J 122, B5), −17.91 (1B, d, J 92, B4), −19.05 (2B, d, J 150, B3, 6), −33.85 (1B, d, J 89, B10), −36.60 (1B, d, J 137, B1); $^{13}$C NMR (100 MHz; $CD_3CN$; $Me_4Si$) $\delta_C$/ppm: 133.05 (2C, d, Ph), 129.11 (1C, d, Ph), 127.54 (3C, m, Ph), 44.15 (1C, s, $C_{carborane}$), 42.68 (1C, s, $C_{carborane}$), 33.80 (1C, t, $NCH_2$), 32.66 (1C, t, $CH_2$), 30.82 (1C, t, $CH_2$); m/z (ER) 269.42 (10%), 267.25 (100%), calcd. 269.27 (10%), 267.27 (100%) [M−H]$^-$.

132.57 (2C, d, J=1.60, Ph), 132.04 (1C, t, J=1.69, Ph), 129.97 (1C, t, J=1.55, Ph), 128.05 (2C, t, J=1.60, Ph),

Example 22

8-(2-amineethyl)-ammonio-8'-methoxy-3,3'-commobis(1,2-dicarba-3-cobalta(III)-closo-dodecabor)ate (1-), (compound CB-15am, the intermediate for the preparation of CB-15)

Figure 22:
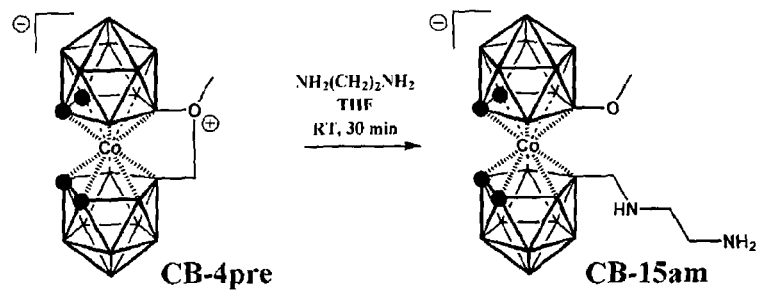

Structural formula of the compound CB-15am is depicted in FIG. 2. The preparative procedure leading to the compound CB-15am is shown in FIG. 22.

The starting electroneutral bridged derivative [μ-8-$CH_2$-8'-$CH_3O$-(1,2-$C_2B_9H_{10}$)$_2$-3,3'-Co(III)] (281 mg, 0.77 mmol) was dried for 12 h and then dissolved in tetrahydrofurane (THF, 5 ml) under nitrogen. Ethylendiamine in excess (0.51 ml, 7.65 mmol, Aldrich) was added to the resulting solution and the reaction mixture was vigorously stirred over 30 min. period. The reaction course was periodically monitored by TLC. The reaction was quenched by addition of diluted HCL (3M, 3 ml) and by removal of the solvent on a rotary evaporator under reduced pressure. The residue was treated by methylene chloride (60 ml) and the solids were removed by filtration. The filtrate was then treated by diluted HCl (3 M, 3×20 ml) and and orange solid that precipitated out was filtered and dried in the air. The crude product was dissolved in ethylacetate (10 ml) and the solution was shaken with 10% aqueous solution of $Na_2CO_3$ (2×20 ml). The organic layer was then separated and evaporated to dryness under reduced pressure. Solids were dissolved in methylene chloride (10 ml) to which few drops of ethylacetate were added, the solution was filtered and layered by hexane (20 ml) and left to stand for 2 days. The orange solid product was recovered by filtration and dried, yield 193 mg (59%).

Found: $^1H\{^{11}B\}$NMR (400 MHz; $CD_3CN$, $Me_4Si$) $\delta_H$/ppm: 6.15 (1H, t, NH), 3.88 (2H, s, $CH_{carborane}$), 3.83 (2H, S, $CH_{carborane}$), 3.41 (3H, s, $CH_3O$), 3.27 (3H, m, $CH_2NH_3$), 2.92 (4H, p, $CH_2N$), 2.87 (4H, s, B(4, 7, 9', 12')H), 2.86 (2H, t, $BCH_2N$), 2.82 (1H, s, B(10)H), 2.74 (2H, s, B(4', 7')H), 2.60 (1H, s, B(10')H), 2.17 (2H, s, B(9, 12)H), 1.92 (3H, s,), 1.87 (2H, s, B(4', 7')H), 1.59 (1H, s, B(6)H), 1.54 (4H, s, B(5, 5', 11, 11')H), 1.40 (1H, s, B(6')H); $^{11}$B NMR (128 MHz; $CD_3CN$; $Et_2O.BF_3$) $\delta_B$/ppm: 26.79 (1B, s, B8'), 10.36 (1B, s, B8), −0.43 (1B, d, J 140, B10), −2.58 (1B, d, J 137, B10), −5.38 (2B, d, J 147, B9, 12), −6.69 (4B, d, J 171, B4, 7, 9', 12'), −8.16 (2B, d, J 183, B4', 7'), −18.13 (2B, d, J 137, B5, 11), −19.10 (2B, d, J 137, B5', 11'), −23.60 (1B, d, J 171, B6), −28.40 (1B, d, J 159, B6'); $^{13}$C NMR (100 MHz; $CD_3CN$; $Me_4Si$) $\delta_C$/ppm: 57.96 (1C, t, $CH_2$), 51.75 (2C, t, $CH_2N$), 51.39 (2C, d, $CH_{carborane}$), 48.36 (2C, d, $CH_{carborane}$), 37.07 (1C, q, $CH_3$); m/z (APCI$^-$): 426.42 (100%), 429.42 (11%), calcd. 426.36 (100%), 429.36 (11%), [M−H]$^-$.

Example 23

8-(5-ammoniopentoxy)-3,3'-commo-bis(1,2-dicarba-3-cobalta(III)-closo-dodecabor)ate (1-), (compound CB-16am, the intermediate for the preparation of CB-16)

Figure 23:
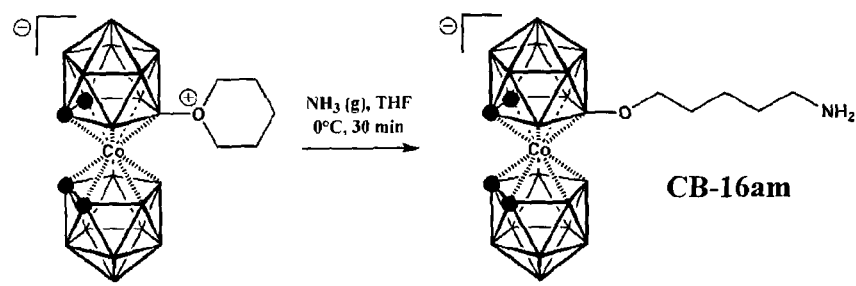

Structural formula of the compound CB-16am is depicted in FIG. 2. The preparative procedure leading to the compound CB-16am is shown in FIG. 23.

The starting zwitterion [8-$O_5H_{10}$O-(1,2-$C_2B_9H_{10}$)(1',2'-$C_2B_9H_H$)-3,3'-Co(III)] (500 mg, 1.22 mmol), prepared according to reported procedure (*Dalton Trans.* 2003, 556-561), was dissolved under nitrogen in THF (20 ml) and the solution was cooled down to 0° C. Then, gaseous ammonia was bubbled through this solution over 5 min. period and the solution was then left to stand for additional 25 min. at room temperature. Reaction was periodically analyzed using TLC (in $CH_3CN$—$CH_2Cl_2$ 3:1 b.v.). The solution was evaporated to dryness under reduced pressure using a rotary evaporator. The crude product was dissolved in $Et_2O$ (30 ml) and then shaken with diluted HCl (3M, 3×20 ml). The organic layer was separated, filtered through paper filter, and the solvent was removed under reduced pressure. The crude product was crystallized by dissolution in methylene chloride (20 ml with addition of 1 ml of methanol) and careful layering with hexane (80 ml). The solid that separated was filtered and dried in vacuum; yield 482 mg (92%).

Found: $^1$H NMR (400 MHz; $CD_3CN$, $Me_4Si$) $\delta_H$/ppm: 4.10 (2H, s, $CH_{carborane}$), 3.98 (2H, s, $CH_{carborane}$), 3.51 (2H, t, $CH_2O$), 2.93 (2H, m, $CH_2N$), 2.80 (1H, s, B(10')H), 2.77 (1H, s, B(8')H), 2.76 (2H, s, B(4, 7)H), 2.59 (2H, s, B(4', 7')H), 2.57 (1H, s, B(10)H), 2.28 (3H, s, $NH_3$), 1.69 (4H, s, B(9, 9', 12, 12)H), 1.63 (1H, s, B(6')H), 1.62 (2H, m, $CH_2$), 1.54 (2H, s, B(5', 11')H), 1.50 (1H, s, B(6)H), 1.48 (2H, m, $CH_2$), 1.45 (2H, s, B(5, 11)H), 1.41 (2H, m, $CH_2$); $^{11}$B NMR (128 MHz; $CD_3CN$; $Et_2O.BF_3$) $\delta_B$/ppm: 23.87 (1B, s, B8), 5.11 (1B, d, J 140, B8'), -0.27 (1B, d, J 143, B10), -2.86 (1B, d, J 146, B10'), -5.21 (2B, d, J 143, B4'7'), -7.55 (4B, d, J 146, B 9, 9', 12, 12'), -9.11 (2B, d, J 201, B4, 7), -17.58 (2B, d, J 153, B5', 11'), -20.43 (2B, d, J 153, B5, 11), -22.50 (1B, d, J 153, B6'), -28.85 (1B, d, J 168, B6); $^{13}$C NMR (100 MHz; $CD_3CN$; $Me_4Si$) $\delta_C$/ppm: 69.33 (1C, t, $CH_2O$), 53.44 (1C, t, $CH_2N$), 47.45 (2C, d, $CH_{carborane}$), 41.00 (2C, d, $CH_{carborane}$), 31.20 (1C, t, $CH_2$), 26.92 (1C, t, $CH_2$), 23.50 (1C, t, $CH_2$); m/z (APCI): 426.42 (100%) 430.42 (8%), calcd. 426.38 (100%) 430.38 (8%) [M–H]$^-$.

Example 24

7-methyleneammonio-(7,8-nido-dikarbaundekabor)ate (1-), (compound CB2-am) by degradation Br—$CH_2$-1,2-carborane ammonia (compound CB-2am, the intermediate for the preparation of CB-2)

Figure 24:
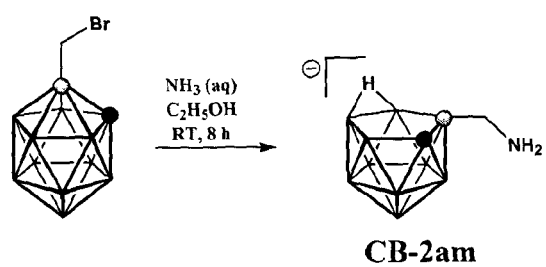

Structural formula of the compound CB-2am is depicted in FIG. 2. The preparative procedure leading to the compound CB-2am is shown in FIG. 24.

The commercially available 1-Br—$CH_2$-1,2-$C_2B_{10}H_{11}$ (1.0 g, 4.2 mmol, purchased from Katchem, Ltd., Prague) was dissolved in aqueous ethanol (96%, 10 ml) and aqueous ammonia (24% b.v., 5 ml) was added. The reaction mixture was stirred under nitrogen for 8 h, when a spot of the starting compound on TLC($R_F$ 0.91, Silufol, $CHCl_3$—$CH_3CN$, 2:1 b.v., detection: iodine vapours and spray with 1% $AgNO_3$ a slow reduction to a grey colour). Volatiles were then removed under reduced pressure. A solid residue was dried dissolved in acetone: $CH_2Cl_2$ mixture (4:1 b.v.), and the product was isolated by chromatography on a silica gel column (20×2 cm I.D.). The course of chromatography was monitored by TLC using the same solvent mixture. The first eluting main band corresponding to $R_F$ 0.33 on TLC was collected. The solvents were immediately removed at cold under reduced pressure and the product was then dried and crystallized by dissolution in $CH_2Cl_2$, layering with hexane and leaving to stand for three days. This reaction can be alternatively carried out with toluene (dry) solution of the starting compound and gaseous 100% ammonia from pressure bottle which is bubbled through. Reaction time was then 3 h providing a similar mixture of identical products, inclusive their mutual ratios; according to TLC and NMR. Yield of 1-$H_3$N—$CH_2$-1,2-$C_2B_{10}H_{11}$ 0.43 g (62%).

Found: $R_F$ 0.33 (Silufol), $^1$H NMR (400 MHz; $CD_3CN$, $Me_4Si$) $\delta_H$/ppm: 3.072 (1H, d, J=13.4 Hz, $CH_2NH_2$), 2.866 (1H, d, J=13.6 Hz, —$CH_2$—NH), 1.855 (114, S, $CH_{carborane}$), 1.988 (2H, s, B11); 1.695, 1.366 (2H, 2 s, BH), 1.281, 1.066 (2H, 2 s, BH), 1.332 (1H, s, B(3)H), 0.553 (1H, s, B(1)H), 0.117 (1H, s, B(10)H), -2.738 (1H, s, μ-BR); $^{11}$B NMR (128 MHz; $CD_3CN$; $Et_2O.BF_3$) $\delta_B$/ppm: –11.09 (2B, d, J 43), –15.16 (2B, d, J 142), –19.79 (2B, d, J 159), –20.06 (1B, d, J 147), –32.85 (1B, d, J 89, B10), –37.16 (1B, d, J 140, B1); m/z (E.I.) 148 [$C_2B_9H_{11}CH_2$] (50), 164 (100), 165 (40), calcd. 163.46, 165.21) [M]. The spectral data are in agreement with these reported previously in the literature (J. G. Wilson et al., *Inorg. Chem.* 36, 4756-4761, 1997).

The disclosed procedure starts from commercially available chemicals and represents simple one step approach, compared to reported three step procedure starting from nido-dekaborane(14) (J. G. Wilson, see above), and provides higher yield of the product.

Example 25

8-(5-ammonio-3-oxa-pentoxy)-3,3'-como-bis(1,2-dicarba-3-cobalta(III)-closo-dodekabor)ate (1-), (compound CB-17am) (compound CB-17am, the intermediate for the preparation of CB-17)

Figure 25:
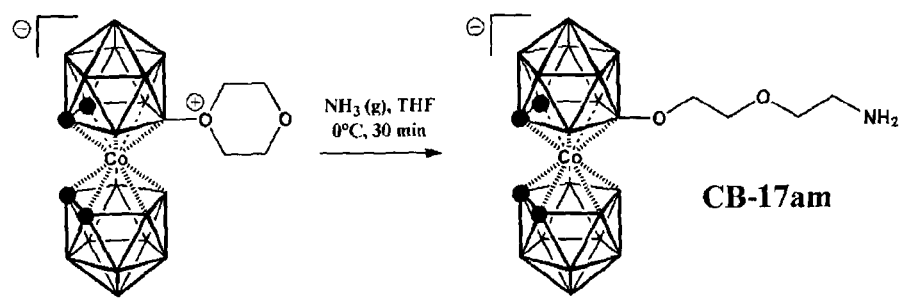

Structural formula of the compound CB-17am is depicted in FIG. 2. The preparative procedure leading to the compound CB-17am is shown in FIG. 25.

The new procedure described above for preparation of CB-16am can be applied in preparation of the compound CB-17am that has been already reported in the literature (*J. Orgmet. Chem.* 2002, 649, 1). The starting derivative [8-$C_4H_8O_2$-(1,2-$C_2B_9H_{10}$)(1',2'-$C_2B_9H_{11}$)-3,3'-Co(III)] (500 mg, 1.22 mmol), prepared according to reported procedure (*Collect. Czech. Chem. Commun.* 62, 1997, 47) (500 mg, 1.22 mmol) was reacted with gaseous ammonia in THF analogously as in the case of CB-16am. Also the isolation was carried out by the same procedure as that used in case of CB-16am; yield 511 mg (98%).

Found: $^1$H NMR (400 MHz; $CD_3CN$, $Me_4Si$) $\delta_H$/ppm: 7.86 (3H, t, $NH_3$), 4.07 (2H, s, $CH_{carborane}$), 3.98 (2H, s, $CH_{carborane}$), 3.92 (2H, t, $CH_2O$), 3.77 (2H, t, $CH_2O$), 3.67 (2H, t, $CH_2O$), 3.50 (2H, m, $CH_2N$), 3.10 (1H, s, B(10)H), 2.86 (2H, s, B(4', 7')H), 2.64 (1H, s, B(8')H), 2.65 (2H, s, B(4, 7)H), 2.10 (1H, s, B(10')H), 2.06 (2H, s, B(9, 12)H), 1.85 (2H, s, B(9', 12')H), 1.62 (1H, s, B(6'')H), 1.55 (2H, s, B(5', 11'')H), 1.48 (2H, s, B(5, 11)H), 1.38 (1H, s, B(6)H); $^{11}$B NMR (128 MHz; $CD_3CN$; $Et_2O.BF_3$) $\delta_B$/ppm: 24.53 (1B, s, B8), 6.91 (1B, d, J 140, B8'), 0.61 (1B, d, J 140, B10), -2.56 (1B, d, J 143, B10''), -5.08 (2B, d, J 195, B4, 7), -6.55 (4B, d, J 147, B9, 9', 12, 12'), −9.24 (2B, d, J 153, B4', 7'), −17.20 (2B, d, J 156, B5, 11), −20.18 (2B, d, J 156, B5', 11'), −22.39 (1B, d, J 162, B6), −28.64 (1B, d, J 168, B6'); $^{13}$C NMR (100 MHz; CD$_3$CN; Me$_4$Si) δ$_C$/ppm: 76.95 (1C, t, CH$_2$O), 74.82 (1C, t, CH$_2$O), 71.89 (1C, t, CH$_2$O), 57.12 (2C, d, CH$_{carborane}$), 52.37 (2C, d, CH$_{carborane}$), 45.705 (1C, t, CH$_2$N); m/z (APCI): 427.42 (100%), 430.50 (14%), calcd 427.35 (100%), 430.34 (14%) [M−H]$^−$. The data are in agreement with those previously published for this compound in the literature. (*J. Orgmet. Chem.* 649, 2002, 1). Compared to the above published method comprising several steps, the procedure disclosed here is distinctly simpler and provides essentially quantitative yields.

Example 26

1-(2-sulfonamidethyl)-1,2-dicarba-closo-dodecaborane (compound CB-23)

Figure 28:
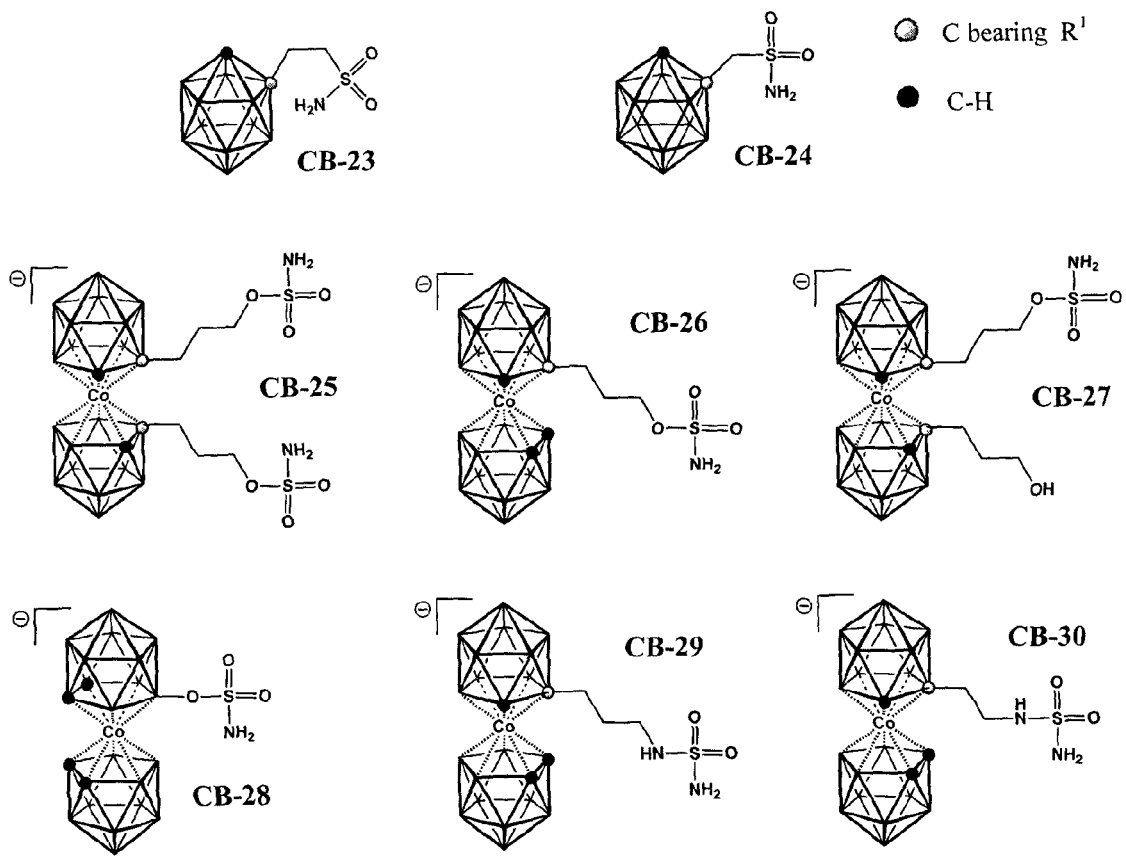
FIG. 28 shows structural formulas of compounds described in examples n. 26-30 (compounds CB-23, 25, 26, 29 and 30)
Figure 30:
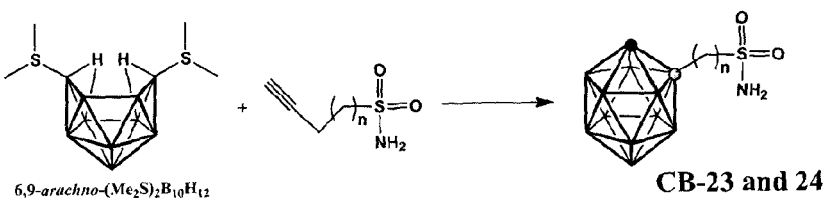
FIG. 30 shows procedure for preparation of compound CB-23, which is 1-(2-sulfonamidethyl)-1,2-dicarba-closo-dodecaborane described in example 26.

Structural formula of the compound CB-23 is depicted in FIG. 28. The preparative procedure leading to the compound CB-5 is shown in FIG. 30.

The known compound 6,9-bis(dimethylsulphide)decaborane (1178 mg, 4.8 mmol), prepared according to procedure described in the literature (Knoth et al., *J. Inorg. Nucl. Chem.* 20, 1961, 66) was heated in dry toluene-acetonitrile mixture (10 ml, 1:1 b.v.) under nitrogen with but-3-yn-1-sulfonamide (130 mg, 1.0 mmol) prepared according to procedure known for this type of acetylenic compounds (see e.g. Benfodda et al., *Heteroatom Chem.* 20, 2009, 355; Benfodda et al., *Eur. J Med. Chem.* 45, 2010, 1225) to a reflux temperature and heating was continued for 48 h. After cooling down, silicagel for chromatography (2 g) was added to the reaction mixture and volatiles were removed under reduced pressure. The solid residue was poured atop of silica gel column (20×1 cm I.D.) and the crude product was isolated by liquid chromatography using diethyl ether as the mobile phase. Repeated chromatography provided the pure compound CB-23, yield 25 mg (10%).

Found: $^1$H NMR (CD$_3$CN, 400 MHz, BF$_3$.Et$_2$O) δ$_H$/ppm: 4.54 (2H, bs, NH$_2$), 4.28 (1H, s, CH$_{carborane}$), 3.21 (2H, t, CH$_2$S), 2.72 (2H, t, CH$_2$), 2.58 (1H, s, B(9)H), 2.56 (2H, s, B(4,5)H), 2.54 (2H, s, B(8,10)H), 1.71 (4H, s, B(3,6,7,1 OH), 1.64 (2H, s, B(4,5)H), 1.58 (1H, s, B(12)H); $^{11}$B NMR (CH$_3$CN, 128 MHz, BF$_3$.Et$_2$O) δ$_B$/ppm: −2.98 (1B, d, J=146, B12), −5.95 (1B, d, J=150, B9), −9.69 (2B, d, J=153, B8,10), −11.92 (4B overlap, d, J=153, B3,6,7,11), −13.04 (2B, d, J=155, B4,5); m/z (APCI$^−$): 251.21 (M−, 100%), 253.16 (5%), calculated 251.19 (M−, 100%), 253.18 (7%).

Example 27

1,1'-bis(3-sulfamoylpropyl)-3,3'-commo-bis(1,2-dicarba-3-cobalta(III)-closo-dodecabor)ate (1−) (compound CB-25)

Figure 31:
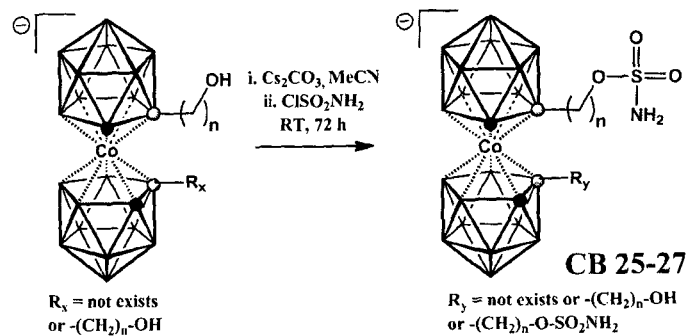
FIG. 31 shows procedure for preparation of compound CB-25, which is 1,1'-bis(3-sulfamoylpropyl)-3,3-commo-bis (1,2-dicarba-3-cobalta(III)-closo-dodecabor)ate and CB-26, which is 1-(3-sulfamoyl-propyl)-3,3'-commo-(decahydro-1, 2-dicarba-3-cobalta(III)-undecahydro-1',2'- -dicarba-closo-dodecabor)ate (1-), sodium salt dihydrate described in example 27.

Structural formula of the compound CB-25 is depicted in FIG. 28. The preparative procedure leading to the compound CB-5 is shown in FIG. 31.

The starting known derivative Cs[HO—(CH$_2$)$_3$)C$_2$B$_9$H$_{10}$)$_2$-3,3'-Co] (500 mg, 0.9 mmol), prepared according to the previously published procedure (Grüner et al., *Dalton Trans.* 41, 2012, 7498), was dried in vacuum for 24 h and then dissolved under argon in 10 ml of dry acetonitrile in a Schlenk-type flask. Solid Cs$_2$CO$_3$ (664 mg, 2.2 mmol) was added in one portion followed, after 30 min of stirring, with solid sulfamoyl chloride (Cl—O—SO$_2$—NH$_2$, 302 mg, 3.0 mmol). The reaction mixture was then stirred for additional 72 h at room temperature. The course of reaction was periodically monitored by TLC in CH$_3$CN:CHCl$_3$ (1:3, b.v.). When the starting compound almost disappeared, the solids were removed by filtration and discarded. The red filtrate was evaporated to dryness under reduced pressure. Resulting crude product was dissolved in CH$_2$Cl$_2$ (20 ml), the resulting solution was layered with hexane and left to crystallize. The solids were filtered and dried in vacuum. The product was obtained in the form of Cs$^+$ salt, yield 561 mg (88%). For purposes of the testing of CA enzymes inhibition, this salt was transferred to hydrated sodium salt by metathesis.

Found: $^1$H NMR (CD$_3$CN, 400 MHz, BF$_3$.Et$_2$O) δ$_H$/ppm: 5.66 (4H, bs, NH$_2$), 4.01 (2H, t, CH$_2$O), 3.96 (2H, t, CH$_2$O), 3.82 (2H, s, B(8,8')H), 3.50 (2H, s, CH$_{carborane}$), 3.13 (2H, s, B(9,9')H), 3.03 (4H, t, CH$_2$), 2.83 (4H, bs, B(4,4',7,7')H), 2.77 (2H, s, B(10,10')H), 2.38 (4H, t, CCH$_2$), 1.72 (2H, s, B(6,6')H), 1.64 (2H, s, B(12,12')H), 1.61 (4H, bs, B(5,5',11,11')H); $^{11}$B NMR (CD$_3$CN, 128 MHz, BF$_3$.Et$_2$O) δ$_H$/ppm: 7.58 (2B, d, J=143, B8,8'), −0.22 (2B, d, J=72, B10,10'), −4.17 (2B, d, J=143, B9,9'), −5.45 (2B, d, J=146, B4,4'), −6.33 (2B, d, J=131, B7,7'), −9.14 (2B, d, J=140, B12,12'), −14.30 (2B, d, J=126, B5,5'), −16.06 (2B, d, J=171, B11,11'), −17.84 (1B, d, J=266, B6'), −19.41 (1B, d, j=156, B6); $^{13}$C NMR (CD$_3$CN, 100 MHz, BF$_3$.Et$_2$O) δ$_C$/ppm: 71.80 (2C, C$_{carborane}$), 57.50 (2C, CH$_{carborane}$), 32.45 (2C, CH$_2$O), 23.20 (2C, CH$_2$), 14.21 (2C, CH$_2$); m/z (ESI): 598.40 (M−, 100%), 602.28 (5%), calculated 598.31 (M−, 100%), 602.30 (5%).

Example 28

1-(3-sulfamoyl-propyl)-3,3'-commo-(decahydro-1,2-dicarba-3-cobalta(III)-undecahydro-1',2"-dicarba-closo-dodecabor)ate (1−), sodium salt dihydrate (compound CB-26)

Structural formula of the compound CB-26 is depicted in FIG. 28. The preparative procedure leading to the compound CB-5 is shown in FIG. 31.

The starting known caesium salt of the formula Cs[1-HO—(CH$_2$)$_3$-1,2-C$_2$B$_9$H$_{10}$)(1',2'-C$_2$B$_9$H$_{11}$)-3,3'-Co] (500 mg, 1.0 mmol), prepared according to the previously published procedure (Grüner et al., *Dalton Trans.* 41, 2012, 7498), was dried in vacuum at room temperature for 24 h and then dissolved under argon in 10 ml of dry acetonitrile in a Schlenk-type flask. Solid Cs$_2$CO$_3$ (370 mg, 1.1 mmol) was added in one portion and then the slurry was vigorously stirred for 30 min. Then the solid sulfamoyl chloride (225 mg, 2.0 mmol) was poured into reaction flask and the stirring at room temperature was continued for additional 72 h at room temperature. The filtrate was evaporated to dryness under reduced pressure. Resulting crude product was dissolved in CH$_2$Cl$_2$ (20 ml), the solution was layered with hexane (40 ml), and left to crystallize. The solids were filtered and dried in vacuum. The product was obtained in the form of the respective Cs$^+$ salt, yield 548 mg (95%). For purposes of the testing of CA isoenzymes inhibition, this salt was transferred to hydrated sodium salt by metathesis.

Found: $^1$H NMR (CD$_3$CN, 400 MHz, BF$_3$.Et$_2$O) δ$_H$/ppm: 5.66 (2H, s, NH$_2$), 4.00 (2H, t, CH$_2$O), 3.94 (1H, s, CH$_{carborane}$), 3.63 (1H, s, CH$_{carborane}$), 3.56 (1H, s, CH$_{carborane}$), 3.55 (2H, s, B(8,8')H), 2.67 (2H, m, CH$_2$), 2.85 (2H, s, B(10,10')H), 2.73 (2H, s, B(9,12)H), 2.71 (2H, s, B(4',7')H), 2.67 (2H, s, B(4,7)H), 2.53 (2H, s, B(9',12')H), 2.30 (2H, t, CCH$_2$), 1.69 (1H, s, B(5)H), 1.64 (1H, s, B(6)H), 1.57 (1H, s, B(11)H), 1.48 (2H, s, B(5',11')HA 1.43 (1H, s, B(6')H); $^{11}$B NMR (CD$_3$CN, 128 MHz, BF$_3$.Et$_2$O) $\delta_B$/ppm: 6.08 (2B, bd, J=146, B8,8'), −0.39 (2B, d, J=140, B10,10'''), −5.40 (2B, d, J=140, B4,7), −6.45 (4B, J=131, B9,9',12,12'), −7.43 (2B, d, J=131, B4',7'), −15.32 (1B, d, J=159, B5), −16.56 (1B, d, J=180, B11), −18.03 (2B, d, J=171, B5',11'), −19.58 (1B, d, J=204, B6'), −23.17 (1B, d, J=174, B6); $^{13}$C NMR (CD$_3$CN, 100 MHz, BF$_3$.Et$_2$O) $\delta_C$/ppm: 84.12 (1C, C$_{carborane}$), 71.18 (1C, CH$_2$O), 56.79 (1C, CH$_{carborane}$), 53.75 (2C, CH$_{carborane}$), 37.20 (1C, CH$_2$), 31.21 (1C, CH$_2$); m/z (ESI): 461.33 (M−, 100%), 465.42 (3%), calculated 461.30 (M−, 100%), 465.29 (5%).

Example 29

1-propylenesulfamide-3,3'-commo-bis(1,2-dicarba-3-cobalta(III)-closo-dodecabor)ate (1-), (compound CB-29)

Figure 32:
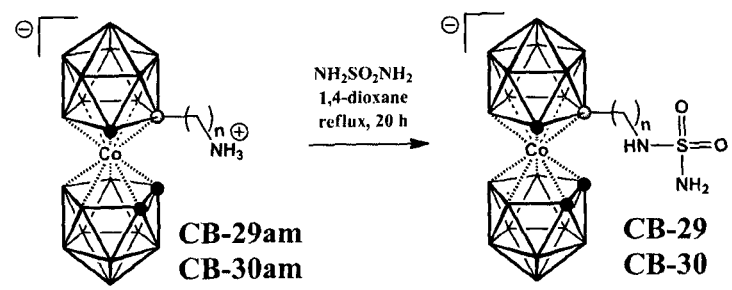
FIG. 32 shows procedure for preparation of compound CB-29, which is 1-propylenesulfamide-3,3'- -commo-bis(1, 2-dicarba-3-cobalta(III)-closo-dodecabor)ate (1-) (example 29) and CB-30, which is 1-ethylenenesulfamide-3,3'-commo-bis(1,2-dicarba-3-cobalta(III)-closo-dodecabor)ate (1-) described in example 30.

Structural formula of the compound CB-29 is depicted in FIG. 28. The preparative procedure leading to the compound CB-5 is shown in FIG. 32.

A mixture of the solid starting compound [(1-H$_3$N—(CH$_2$)$_3$-1,2-C$_2$B$_9$H$_{10}$)(1',2'-C$_2$B$_9$H$_{10}$)-3,3'-Co] (CB29-Am, 50 mg, 0.13 mmol), sulfamide (100 mg, 0.98 mmol) and potassium carbonate (200 mg, 14.4 mmol) was dried in a Schlenk-type flask for 10 h in vacuum at room temperature. Then 1,4-dioxane (10 ml) was added through a rubber septum and the reaction mixture was heated to 85° C. under stirring and then heated at this temperature for 48 h. After cooling down, the solids were filtered out, washed with dioxane (2×2 ml) and discarded. Combined organic phases were evaporated under reduced pressure and resulting solid residue was dissolved in a mixture of CH$_2$Cl$_2$ and CH$_3$CN (4:1 b.v., 2 ml). This solution was injected atop of silica gel column (20×1,5 cm) and eluted by CH$_2$Cl$_2$—CH$_3$CN solvent mixture with gradually increasing content of acetonitrile from 20% to 30% b.v. The first collected fraction contained unreacted starting ammonium derivative (11 mg). Other pure fractions corresponding to product (according to NMR and MS) were combined and evaporated under reduced pressure. The solid orange compound was dissolved in CH$_2$Cl$_2$ (5 ml) by addition of few drop of methanol, resulting solution was carefully layered with hexane and left to crystallize for 2 days. A semi-crystalline product separated, which was decanted, washed with a small amount of hexane and dried 4 h under educed pressure at 50° C.; yield of CB29: 38 mg (43%).

Found: $^1$H NMR (400 MHz; Acetone-d6, Me$_4$Si) $\delta_H$/ppm, 5.82 (2H, s, NHSO$_2$NH$_2$), 5.73 (1H, br, t, CH$_2$NHSO$_2$), 4.028, 3.709, 3.653 (3H, 3 br. s, CH$_{carborane}$), 3.038 (2H, m, J=6.4 Hz, —CH$_2$—NH), 2.845 and 2.781 (2H, 2 m, —CH$_2$—CH$_2$—NH), 3.557, 3.391 (2H, 2 s, B(8,8')H), 3.597 (2H, s, B(10,10')H); 2.877 (2H, H$_2$O), 2.841 (2H, s, B(10,10')H), 2.633, 2.634, 1.958, 1.904 (8H, 4 s, B(4,7,4',7',9,12, 9',12') H); 1.714, 1.659, 1.531 (4H, s, B(5, 11,5',11')H), 1.82 (2H, 2 m, C—CH$_2$), 1.624 1.629 (2H, 2 s, B(6, 6')H); $^{11}$B NMR (128 MHz; Acetone-d6; Et$_2$O,BF$_3$) $\delta_B$/ppm: 6.46 (2B, d, J=141 Hz, B8,8'), 0.56 (2B, d, J=143 Hz, B10,10'), −6.12, −7.022 (8B, 4 d, overlap, B4,7,4',7',9,12, 9',12'), −14.94, −16.37 (2B, 2 d, J=177 Hz, B5,11), −17.84 (2B, d, J=180 Hz, −19.25 (1B, d, J=200 Hz, B6), −22.98 (1B, d, J=179 Hz, B6'); $^{13}$C{$^1$H}NMR (100 MHz; Acetone-d6; Me$_4$Si) $\delta_C$/ppm: 69.53 (1C, C$_{carborane}$), 58.03 (1C, C$_{carborane}$), 54.13 (1C, C$_{carborane}$), 51.63 (1C, C$_{carborane}$), 43.72 (1C, CH$_2$NH), 38.12 (1C, CH$_2$—CH$_2$NH), 31.55 (1C, C—CH$_2$); m/z (ESI$^-$) 460.33 (100%), 463.33 (12%), calcd.: 460.30 (100%), 463.30 (14%) [M]

Example 30

1-ethylenenesulfamide-3,3'-commo-bis(1,2-dicarba-3-cobalta(III)-closo-dodecabor)ate (1-), (compound CB-30)

Structural formula of the compound CB-30 is depicted in FIG. 28. The preparative procedure leading to the compound CB-30 is shown in FIG. 32.

A mixture of the solid starting compound [(1-H$_3$N—(CH$_2$)$_2$-1,2-C$_2$B$_9$H$_{10}$)(1',2'-C$_2$B$_9$H$_{10}$)-3,3'-Co] (CB30-Am, 80 mg, 0.22 mmol) was reacted with sulfamide (225 mg, 2.20 mmol) and potassium carbonate (305 mg, 22.0 mmol) in 1,4-dioxane (15 ml) under stirring in nitrogen at 85° C. for 48 h. The compound was isolated by an identical procedure to that described for Compound CB-29 in Example 29.; yield of CB30: 75 mg (69%).

Found: $^1$H NMR (400 MHz; Acetone-d6, Me$_4$Si) $\delta_H$/ppm, 5.88 (2H, br. s, NHSO$_2$NH$_2$), 5.71 (1H, br, t, CH$_2$NHSO$_2$), 4.08, 3.704, 3.591 (3H, 3 br. s, CH$_{carborane}$), 3.218 (2H, m, J=6.4 Hz, —CH$_2$—NH), 3.013, 2.950 (2H, 2 m, —CH$_2$—CH$_2$—NH), 3.785, 3.295 (2H, 2 s, B(8,8')H), 3.295, 2.934 (2H, s, B(10,10')H); 3.031 (2H, H$_2$O), 2.841 (2H, s, B(10,10') H), 2.645, 2.494, 1.910, 1.844 (8H, 4 s, B(4,7,4',7',9,12, 9',12')H); 1.911, 1.875, 1.847, 1.659, (4H, 4 s, B(5, 11,5',11') H), 1.783 1.788 (2H, 2 s, B(6, 6')H); $^{11}$B NMR (128 MHz; Acetone-d6; Et$_2$O,BF$_3$) $\delta_B$/ppm: 6.53 (2B, d, J=146 Hz, B8,8'), 0.85 (2B, d, J=140 Hz, B10,10'), −5.33, −6.05, −6.89 (8B, 4 d, overlap, B4,7,4',7',9,12, 9',12'), −15.44, −16.37 (2B, 2 d, J=161 Hz, B5,11), −17.82 (2B, d, J=171 Hz, B5',11'), −19.72 (1B, d, overlap, B6), −22.98 (1B, d, J=180 Hz, B6'); $^{13}$C{$^1$H}NMR (100 MHz; Acetone-d6; Me$_4$Si) $\delta_C$/ppm: 67.01 (1C, C$_{carborane}$), 57.95 (1C, CH$_{carborane}$), 54.30 (1C, CH$_{carborane}$), 51.87 (1C, CH$_{carborane}$), 44.85 (1C, CH$_2$NH), 40.00 (1C, CH$_2$—CH$_2$NH), mz (ESI$^-$) 446.50 (100%), 449.33 (14%), calcd.: 446.29 (100%), 449.29 (14%) [M]$^-$.

Example 31

1-propyleneammonio-3,3'-commo-bis(decahydro-1, 2-dicarba-3-cobalta(III)-closo-dodecabor)ate (1-), [(1-H$_3$N—(CH$_2$)$_3$-1,2-C$_2$B$_9$H$_{10}$)(1',2'-C$_2$B$_9$H$_{11}$)-3, 3'-Co], (compound CB-29am, the intermediate in the preparation of compound CB-29)

Figure 29:
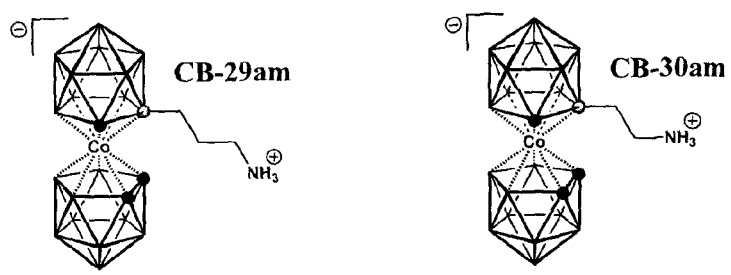
FIG. 29 shows structural formulas of precursors described in examples n. 31, 32 (compounds CB-29am a 30am)
Figure 33:
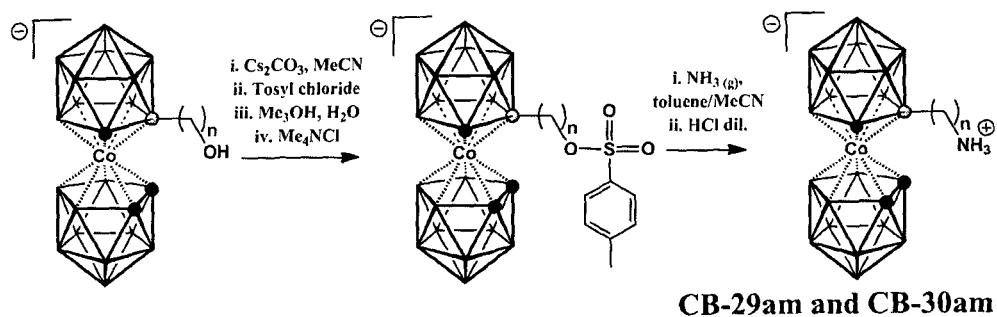
FIG. 33 shows procedure for preparation of compound CB-29am, which is 1-propyleneammonio- -3,3'-commo-bis (decahydro-1,2-dicarba-3-cobalta(III)-closo-dodecabor)ate (1-), and CB-30am, which is 1-ethyleneammonio-3,3'-commo-bis(decahydro-1,2-dicarba-3-cobalta(III)-closo-dodecabor)ate (1-), described in examples 31 and 32.
Figure 34A:
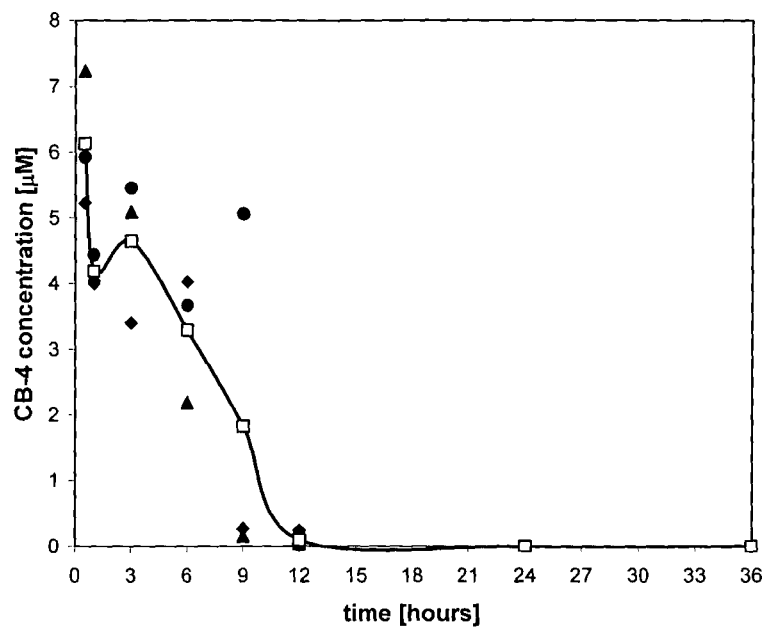
FIG. 34 shows individual mouse and average serum concentrations of compounds CB-4 (panel A) and CB-16 (panel B) during 0.5-36 hours after administration (IC 50 CAIX=50 nm in 28A, IC CAIX=280 nm in 28B). Marks ●, ▲, ♦ stand for mouse 1, 2 and 3, □ stands for average values.
Figure 34B:
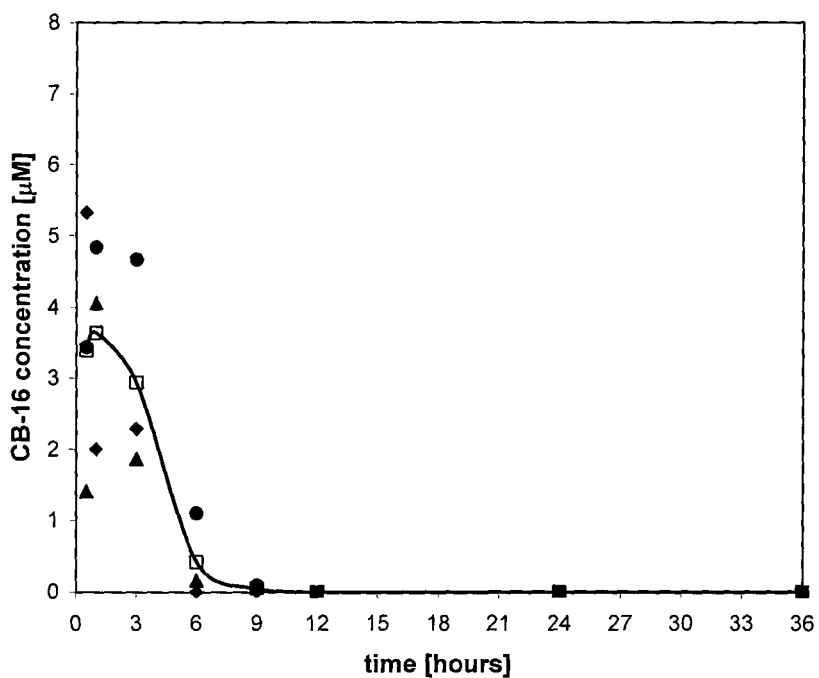

Structural formula of the compound CB-29am is depicted in FIG. 29. The preparative procedure leading to the compound CB-29am is shown in FIG. 33.

A dried trimethylammonium salt of 1-propylenehydroxy-1,2-cobalt bis(dicarbollide), prepared according to known procedure (Grüner et al., *Dalton Trans.* 41, 2012, 7498) 0.50 g (1.13 mmol) was dried 5 h at 80° C. and then was dissolved under nitrogen in dry CH$_3$CN (15 ml). Solid Cs$_2$CO$_3$ (400 mg, 1.23 mmol) was added and the slurry was stirred at 80° C. for 30 min. Then, solution of toluenesulfonyl chloride in acetonitrile (480 mg, 2.51 mmol in 10 ml) was added from syringe and the stirring and heating was continued for additional 2.5 h. After cooling down, the volatiles were removed under reduced pressure. The solid residue was dissolved rapidly in a smallest volume of methanol, then water (25 ml) was added and the crude product was precipitated by addition of an excess of aqueous solution of Me$_4$NCl and rapidly filtered after short standing for 5 min. The orange solid was washed with water and several portions of hexane (3×15 ml) and immediately dried in vacuum at room temperature for 1 h, then dissolved in CH$_2$Cl$_2$, layered with hexane and left to crystallize overnight. The semi-crystalline product was decanted, washed with hexane and dried in vacuum for 8 h.

This procedure furnished essentially pure tosylate of the formula [(1-CH$_3$—C$_6$H$_4$—SO$_2$—O—(CH$_2$)$_3$-1,2-C$_2$B$_9$H$_{10}$(1',2'-C$_2$B$_9$H$_{10}$)-3,3'-Co]Me$_4$N, according to NMR and MS, which can be used as the intermediate for preparation of the ammonium derivative CB-29am; yield 0.66 g (96%).

Found: $^1$H NMR (400 MHz; Acetone-d6, Me$_4$Si) δ$_H$/ppm, 7.782 (2H, d, J=6.8 Hz, ArH), 7.473 (2H, d, 0.1=5.2 Hz, ArH), 4.031 (2H, 2 m, —CH$_2$—O), 3.694, 3.530, 3.402 (3H, 3 br. s, CH$_{carborane}$), 3.791, 3.726 (2H, 2 s, B(8,8')H), 3.447 (12H, s, NMe$_4^+$), 2.934 (2H, s, B(10,10')H), 2.698 and 2.359 (2H, 2 m, —CH$_2$—CH$_2$—O), 2.808, 2.636, 1.948, 1.920 (8H, 4 s, B(4,7,4',7',9,12, 9',12')H); 2.373 (3H, s, CH$_3$), 1.843 (2H, m, C—CH$_2$), 1.63, 1.62 (2H, 2 s, B(5, 11)H), 1.582 (2H, s, B(5',11')H), 1.618 (1H, s, B(6')H), 1.605 (1H, s, B(6)H); $^{11}$B NMR (128 MHz; Acetone-d6; Et$_2$O,BF$_3$) δ$_B$/ppm: 6.44 (2B, d, J=162 Hz, B8,8'), 0.80 (2B, d, J=143 Hz, B10,10'), −6.02, −7.04 (8B, 4 d, overlap, B4,7,4',7',9,12, 9',12'), −15.20, −16.37 (2B, 2 d, J=150 and 177 Hz, B5,11), −17.84 (2B, d, J=171 Hz, B5',11'), −19.43 (1B, d, J=200 Hz, B6), −23.05 (1B, d, J=171 Hz, B6'); $^{13}$C{$^1$H}NMR (100 MHz; Acetone-d6; Me$_4$Si) δ$_C$/ppm: 145.91 (1C, C$_{Ar}$), 134.14 (1C, C$_{Ar}$), 130.92 (2C, C$_{Ar}$), 128.60 (2C, C$_{Ar}$), 71.14 (1C, —CH$_2$—O), 68.81 (1C, C$_{carborane}$), 57.96 (1C, CH$_{carborane}$), 56.07 (4C, Me$_4$N$^+$), 55.99 (1C, —CH$_2$—CH$_2$-0), 53.99 (1C, CH$_{carborane}$), 51.74 (1C, CH$_{carborane}$), 37.34 (1C, C—CH$_2$), 21.61 (1C, CH$_3$); m/z (ESI$^-$) 536.42 (100%), 539.33 (14%), calcd.: 536.34 (100%), 539.33 (16%) [M]$^-$.

100 mg (0.14 mmol) of the above tosylate was dissolved under nitrogen in a solvent mixture composed of dry toluene (5 ml) and acetonitrile (10 ml) in a Ace pressure tube (Aldrich) equipped with a rubber septum with two stainless needles and a stirring bar. Then, the stirred solution was cooled down to −33° C. (bath temperature) and an excess of ammonia (1 ml) was condensed to this tube through a needle). The septum was then replaced with a tight screw cap and the solution was left to warm to room temperature and the tube was then poured into an oiled bath 80° C. warm and the reaction mixture was kept was kept under pressure of ammonia and stirring at this temperature for 48 h. After cooling down to −33° C., the volatiles were removed under reduced pressure (under slow heating to room temperature and then to 40° C.). The residue was dissolved in ether, washed with diluted HCl (3 M, 3×30 ml), the organic phase was washed with water and evaporated to dryness. The product was isolated by chromatography on silica gel using solvent mixture CH$_2$Cl$_2$—CH$_3$CN (4:1, b.v.); yield 55 mg (87%).

Found: $^1$H NMR (400 MHz; Acetone-d6, Me$_4$Si) δ$_H$/ppm, 7.741 (3H, br. s, NH$_3$), 4.031, 3.761, 3.656 (3H, 3 br.s, CH$_{carborane}$), 3.822 (2H, d, J=14.4 Hz, —CH$_2$—NH), 3.767, 3.602 (2H, 2 s, B(8,8')H), 2.935 (2H, s, B(10,10')H); 2.937, 2.663, 1.971, 1.936 (8H, 4 s, B(4,7,4',7',9,12, 9',12')H); 2.751 and 2.473 (2H, 2 m, CH$_2$CH$_2$NH$_2$), 1.998, 1.659 (4H, 2 s, B(5,11)H) 1.744 (2H, br. t, C—CH$_2$), 1.658 (1H, 1 s, B(6)H), 1.611 (1H, s, B(6')H), 1.522 (4H, s, B(5',11')H); $^{11}$B NMR (128 MHz; Acetone-d6; Et$_2$O.BF$_3$) δ$_B$/ppm: 6.51 (2B, d, J=149 Hz, B8,8'), 0.707 (2B, d, J=144 Hz, B10,10'), −6.02, (8B, 4 d, overlap, B4,7,4',7',9,12, 9',12'), −14.70, −16.37 (2B, 2 d, overlap, B5,11), −17.865 (2B, d, J=190 Hz, B 5',11'), −19.221 (1B, d, J=177 Hz, B6), −23.12 (1B, d, J=165 Hz, B6'); $^{11}$C{$^1$H}NMR (100 MHz; Acetone-d6; Me$_4$Si) δ$_C$/ppm: 68.71 (1C, C$_{carborane}$), 57.71 (1C, CH$_{carborane}$), 53.82 (1C, CH$_{carborane}$), 51.74 (1C, CH$_{carborane}$), 48.39 (1C, —CH$_2$—NH$_3$), 41.21 (1C, CH$_2$—CH$_2$—NH$_3$), 37.57 (1C, C—CH$_2$); m/z (ESI$^-$) 381.42 (100%), 385.42 (10%), calcd: 381.34 (100%), 385.34 (10%) [M−H]$^-$.

Example 32

1-ethyleneammonio-3,3'-commo-bis(decahydro-1,2-dicarba-3-cobalta(III)-closo-dodecabor)ate (1-), [(1-H$_3$N—(CH$_2$)$_2$-1,2-C$_2$B$_9$H$_{10}$)(1',2'-C$_2$B$_9$H$_{11}$)-3,3'-Co], (compound CB-30am, the intermediate in the preparation of compound CB-30)

Structural formula of the compound CB-29am is depicted in FIG. 29. The preparative procedure leading to the compound CB-29am is shown in FIG. 33.

Dried trimethylammonium salt of 1-ethylenehydroxy-1,2-cobalt bis(dicarbollide), prepared according to known procedure (Grüner et al., *Dalton Trans.* 41, 2012, 7498) 0.50 g (1.17 mmol) was dried 5 h at 80° C. and then was dissolved under nitrogen in dry CH$_3$CN (15 ml). Solid Cs$_2$CO$_3$ (400 mg, 1.53 mmol) was added and the slurry was stirred at 80° C. for 30 min. Then, solution of toluenesulfonyl chloride in acetonitrile (490 mg, 2.56 mmol in 10 ml) was added from syringe and the stirring and heating was continued for additional 1.5 h. After cooling down, the volatiles were removed under reduced pressure. The solid residue was treated by the same procedure as that described above in the Example 31 for compound CB-29am. Similarly as in the above case, the essentially pure tosylate of the formula [(1-CH$_3$—C$_6$H$_4$—SO$_2$—O—(CH$_2$)$_2$-1,2-C$_2$B$_9$H$_{10}$)(1',2'-C$_2$B$_9$H$_{10}$)-3,3'-Co]Me$_4$N, was obtained, according to NMR and MS, which can be used as the intermediate for preparation of the ammonium derivative CB-30am; yield 0.58 g (83%).

Found: $^1$H NMR (400 MHz; Acetone-d6, Me$_4$Si) δ$_H$/ppm, 7.799 (2H, d, J=7.32 Hz, ArH), 7.497 (2H, d, J=7.5 Hz, ArH), 4.155 (2H, 2 q, —CH$_2$—O), 3.728, 3.557, 3.456 (3H, 3 br. s, CH$_{carborane}$), 3.735, 3.668 (2H, 2 s, B(8,8')H), 3.456 (12H, s, NMe$_4^+$), 2.97, 2.877 (2H, 2 s, B(10,10')H), 3.046 and 2.706 (2H, 2 m, —CH$_2$—CH$_2$O), 2.671, 2.656, 2.009, 1.963 (8H, 4 s, B(4,7,4',7',9,12, 9',12')H); 2.472 (3H, s, CH$_3$), 1.617, 1.485 (2H, 2 s, B(5, 11)H), 1.53 (2H, s, B(5',11')H), 1.618 (1H, s, B(6')H), 1.557 (1H, s, B(6)H); $^{11}$B NMR (128 MHz; Acetone-d6; Et$_2$O,BF$_3$) δ$_B$/ppm: 6.77 (2B, d, J=144 Hz, B8,8'), 1.11, 0.78 (2B, 2 d, J=147 and 149 Hz, B10,10'), −5.76, −6.99 (8B, 4 d, overlap, B4,7,4',7',9,12, 9',12'), −15.65, −16.42 (2B, 2 d, J=150 and 146 Hz, B5,11), −17.58 (2B, d, J=156 Hz, B5',11'), −19.91 (1B, d, J=180 Hz, B6), −23.00 (1B, d, J=169 Hz, B6'); $^{13}$C{$^1$H}NMR (100 MHz; Acetone-d6; Me$_4$Si) δ$_C$/ppm: 146.07 (1C, C$_{Ar}$), 134.08 (1C, C$_{Ar}$), 131.01 (2C, C$_{Ar}$), 128.63 (2C, C$_{Ar}$), 70.88 (1C, —CH$_2$—O), 64.94 (1C, C$_{carborane}$), 57.29 (1C, CH$_{carborane}$), 56.07 (4C, Me$_4$N$^+$), 53.95 (1C, 51.94 (1C, CH$_{carborane}$), 38.78 (1C, C—CH$_2$), 21.58 (1C, CH$_3$); m/z (ESI$^-$) 522.25 (100%), 525.17 (15%), calcd.: 522.32 (100%), 525.31 (16%) [M]$^-$.

150 mg (0.25 mmol) of the above tosylate was dissolved under nitrogen in a solvent mixture composed of dry toluene (5 ml) and acetonitrile (10 ml) in a Aldrich pressure glass tube equipped with a rubber septum with two stainless needles and a stirring bar. Then, the stirred solution was cooled down to −33° C. (bath temperature) and an excess of ammonia (1 ml) was condensed to this tube through a needle). The septum was then replaced with a tight screw cap and the solution was left to warm to room temperature and the tube was then poured into an oiled bath 85° C. warm and the reaction mixture was kept under pressure of ammonia and stirring at this temperature for 48 h. After cooling down to −33° C., the volatiles were removed under reduced pressure (under slow heating to room temperature). The residue was dissolved in ether, washed with diluted HCl (3 M, 3×30 ml), the organic phase was washed with water and evaporated to dryness. The product was isolated by chromatography on silica gel using solvent mixture $CH_2Cl_2$—$CH_3CN$ (4:1, b.v.); yield 85 mg (92%).

Found: $^1H$ NMR (400 MHz; Acetone-d6, $Me_4Si$) $\delta_H$/ppm, 7.8 (3H, br. s, $NH_3$), 4.156, 3.843, 3.714 (3H, 3 br.s, $CH_{carborane}$), 3.983 and 3.464 (2H, 2 q, —$CH_2$—NH), 3.768, 3.558 (2H, 2 s, B(8,8)H), 3.411, 2.928 (2H, 2 q, $CH_2CH_2NH_2$), 3.080, 3.004 (2H, 2 s, B(10,10')H); 2.731, 2.705, 1.923, 1.875 (8H, 4 s, B(4,7,4',7',9,12, 9',12')H); 1.989, 1.849 (2H, 2 s, B(5,11)H), 1.748 (1H, Is, B(6)H), 1.611 (1H, s, B(6')H), 1.626 (2H, s, B(5',11')H); $^{11}B$ NMR (128 MHz; Acetone-d6; $Et_2O.BF_3$) 4/ppm: 6.99 (2B, d, J=140 Hz, B8,8'), 1.35, 0.66 (2B, 2 d, J=143 and 144 Hz, B10,10'), −5.60, −7.00 (8B, 4 d, overlap, B4,7,4',7',9,12, 9',12'), −15.58, −16.32 (2B, 2 d, overlap, B5,11), −17.45 (2B, d, J=156 Hz, B 5',11'), −19.67 (1B, d, J=178 Hz, B6), −23.00 (1B, d, J=171 Hz, B6'); $^{13}C$ NMR (100 MHz; $CD_3CN$; $Me_4Si$) $\delta_C$/ppm: 65.50 (1C, $C_{carborane}$), 57.58 (1C, $CH_{carborane}$), 53.59 (1C, $CH_{carborane}$), 51.85 (1C, $CH_{carborane}$), 49.35 (1C, —$CH_2$—$NH_3$), 37.77 (1C, C—$CH_2$) m/z (ESI⁻) 367.33 (100%), 370.33 (10%), calcd: 367.32 (100%), 370.31 (10%) [M–H]⁻.

Example 33

Testing the Effectiveness of Substances In Vitro

The compounds were assayed for inhibition activity of two isoforms of human carbonic anhydrase: hCA II and hCA IX. The human carbonic anhydrase II (HCA II) was purchased from Sigma Aldrich (Cat. No. C6165) in the form of lyophilized protein, which was dissolved before use in 10 mmol·l⁻¹ HEPES pH 7.0 to a concentration of 300 µmol·l⁻¹ and further diluted as required. Human carbonic anhydrase IX (HCA IX) was prepared by recombinant expression system in insect (*Drosophila* expression system, Invitrogen). Construct contained the extracellular CA domain (amino acid residues 139-390) cloned into the pMT/BiP/V5-His vector (Invitrogen) and the target protein was expressed in serum-free media SF 900 II (Gibco, Invitrogen). This protein was further purified from media by chelating chromatography carrier His-Select Nickel Affinity Gel (Sigma, Cat No. P6611) and gel chromatography (Superdex 200 GL 30/300, GE Healthcare) according to the manufacturer's recommendations.

Testing of the inhibitory efficiency of compounds in vitro were performed using conventional colorimetric method (Maren, T H, Ellison, A C, Mol. Pharmacol. 3, 1967, 503-508) with some modifications according: (Brion, L P et al., Anal. Biochem. 175, 1988, 289-297). The principle of the method is based on measuring the rate of acidification of the solution that is observed as the color-shift of the acid-base-indicator (fenol red). The reaction was conducted in a glass tube placed in an ice bath (0° C., all stock solutions and enzymes were kept at the same temperature). In a typical experiment, a 5 µmol·l-1 enzyme (HCA HCA II and IX) in 10 ml of 10 mmol·l⁻¹ HEPES, pH 7.0 added varying amounts of test inhibitor dissolved in DMSO (so that the final concentration of DMSO did not exceed 2% vol./vol.). The volume of a sample was added to 100 ml of water and the mixture was added to a solution of 800 ml of 1 mmol·l⁻¹ $NaHCO_3$, pH 10.2 containing 0.01% (wt./vol.) of Fenol red. This was followed by a $CO_2$ saturation (stream flow 50 ml/min.) using a needle (18 G) up to color transition of fenol-red from red to yellow (typically 60 seconds by default). After saturation was added to the mixture of 100 ml of $NaHCO_3$ concentration of 500 mmol·l⁻¹ and pH 10.2 (accompanied by a color transition back to a reddish-purple color), then the saturation of $CO_2$ was continued under the same conditions, and the time of color change go back to the yellow color was measured. End point of reaction was determined by visual comparison with reference tube containing acid-base indicator (0.01% (wt./vol.) Fenol-red) and the pH adjusted to 7.0. The negative control (no added enzyme) achieved endpoint typically within 58±2 s in the presence of enzymatic activity was measured correspondingly shorter time. Enzyme activity unit (EU), carbonic anhydrase is defined as the amount of enzyme required to reduce the time by half, compared to the negative control (Brion, L P, et al., Anal. Biochem. 175, 1988, 289-297). Molar activity was calculated according to the formula:

$$CA(EU/\text{mol protein}) = \frac{\log(t_B/t_S)}{n_{prot}\log 2}$$

where $t_B$ is the time of negative control without enzyme and $t_S$ is the time measured with an enzyme sample (and inhibitor), $n_{prot}$ is the number of moles of protein present in the sample. The value of $IC_{50}$ for the inhibitor concentration corresponds inhibitor contraction required to decrease the specific activity to half of the value of non-inhibited enzyme. Selectivity towards CA IX inhibitor was calculated as the ratio of $IC_{50}$ values for inhibition of HCA II against the value of $IC_{50}$ for inhibition CA IX enzyme. The results are shown in Table 1.

TABLE 1

$IC_{50}$ values for individual substances with enzymes hCA II and hCA IX.

| | $IC_{50}$ (hCA II) [µmol·l⁻¹] | $IC_{50}$ (hCA IX) [µmol·l⁻¹] | Selectivity to hCA IX $IC_{50}$ (hCA II)/$IC_{50}$ (hCA IX) |
|---|---|---|---|
| CB-1 | 2.40 | 0.37 | 6.49 |
| CB-2 | 4.60 | 2.60 | 1.77 |
| CB-3 | 21.00 | 3.60 | 5.83 |
| CB-4 | 5.00 | 0.05 | 100 |
| CB-5 | 3.70 | 0.04 | 92.5 |
| CB-6 | 39.10 | 1.08 | 36.2 |
| CB-8 | 2.44 | 0.37 | 6.59 |
| CB-10 | 67.9 | 9.68 | 7.0 |
| CB-11 | 83.90 | 1.50 | 55.9 |
| CB-12 | 14.90 | 1.49 | 10.0 |
| CB-13 | 4.00 | 0.08 | 48.8 |
| CB-15 | 14.00 | 2.00 | 7.00 |
| CB-16 | 0.68 | 0.28 | 2.43 |
| CB-17 | 12.00 | 0.35 | 34.3 |
| CB-19 | 8.90 | 2.00 | 4.45 |
| CB-20 | 1.60 | 0.49 | 3.27 |
| CB-23 | 0.4 | 0.38 | 1.05 |
| CB-25 | 0.04 | 0.004 | 10 |
| CB-26 | 0.11 | 0.014 | 7.9 |
| CB-29 | 3.9 | 0.022 | 177 |
| CB-30 | 0.57 | 0.0007 | 814 |

Examples 34 and 35

The Crystal Structures of HCA II Complexed with Substances CB-1 and CB-2

The complex of human carbonic anhydrase II (HCA II) with a compound of the CB-1 was prepared by adding 1.1 molar excess of CB-1 (20 mmol·l⁻¹ stock solution in DMSO) in a solution of HCA II protein concentration of 10 mg/ml (Sigma, cat. No. C6165) in a buffer composed of 100 mmol·l⁻¹ Tris-HCl, pH 8.5. Complex was prepared identically for HCA II with a compound CB-2.

Crystals with dimensions 0.4×0.2×0.1 mm were prepared by diffusion in the gas phase (hanging drops method) according to the following instructions: 2 µl of complex were mixed with 2 µl of precipitant solution composed of 2.5 mol·l⁻¹ (NH4) 2SO4, 0.3 mol·l⁻¹NaCl, 100 mmol·l⁻¹ Tris-C1, pH 8.2. The crystallization drop was equilibrated in a closed container (EasyXtal Tool, Quiagen) against 1 ml precipitant solution of identical composition.

For diffraction experiments the crystals were washed with a precipitation solution with 20% glycerol (volume percent) and frozen in liquid nitrogen. Diffraction data for the crystals of the complex were collected at a temperature of −173.15° C. on the synchrotron source BESSY, Berlin), used wavelength was 0.09537 nm and the detector MAR Mosaic 225 CCD. Diffraction data were processed with the programs MOSFLM (Leslie, Acta Crystallogr. D Biol. Crystallogr., 62, 2006, 48-57) and SCALA (Evans, Acta Crystallogr. D Biol. Crystallogr., 62, 2006, 72-82). The structure was solved by difference Fourier methods, where as the initial model was used HCA II crystal structure with the access code 1H9N from the Protein Data Bank. The models were refined using rigid body refinement and then by restrained refainment of individual atoms while maintaining the proper stereochemistry using REFMAC (Murshudov et al., Acta Crystallogr. D Biol. Crystallogr., 53, 1997, 240-255), which is part CCP4 programs (CCP4, Acta crystallographic Section D, 50, 1994, 760-763).

Figure 26:
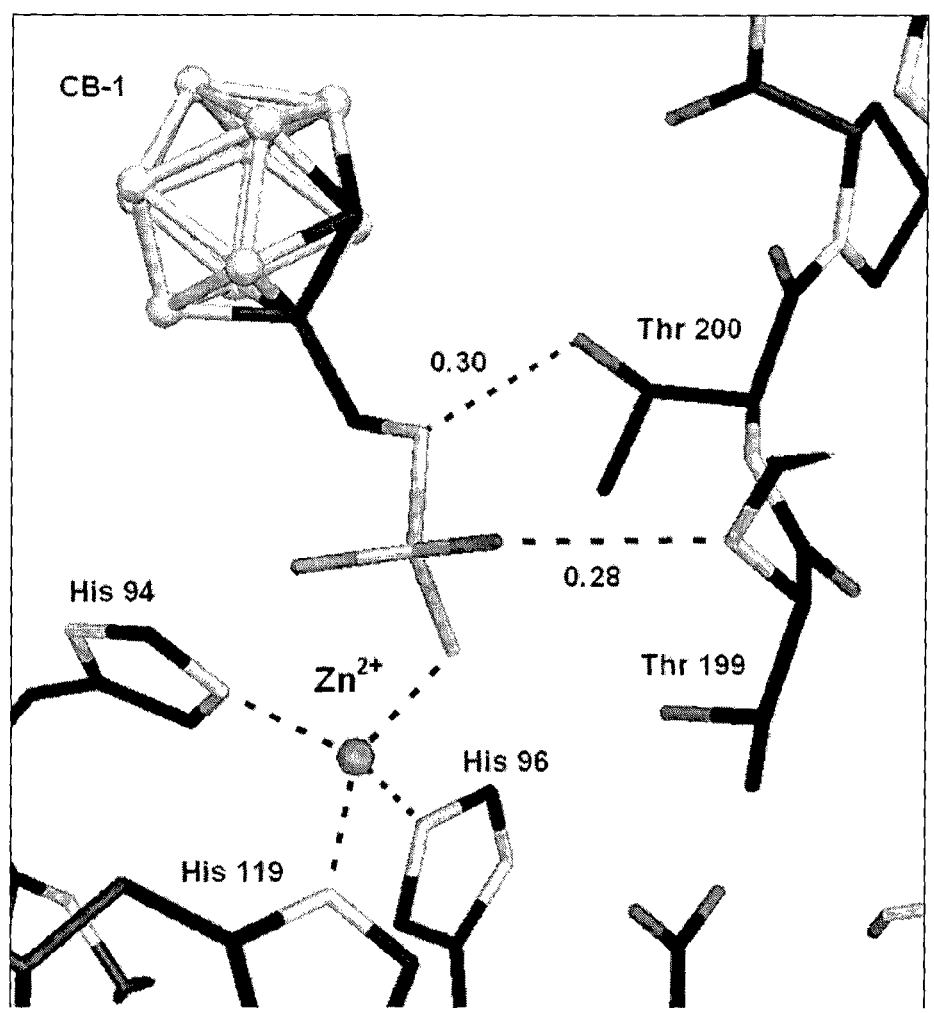
In FIGS. 26 and 27 individual atoms are joined by sticks (stick model representation; stick represents covalent bond; bond multiplicity is not shown). Black dotted lines without numbers represent coordination bonds of nitrogen atoms to the zinc cation (grey sphere), black dotted lines with number represent hydrogen bonds, the number corresponds to a distance between hydrogen donor and acceptor in nanometers. Atom color coding: carbon atoms are shown in black, nitrogen atoms are shown in white, oxygen atoms are shown in dark grey, sulfur atoms are shown in light grey and $Zn^{2+}$ cation is represented as gray sphere.
Figure 27:
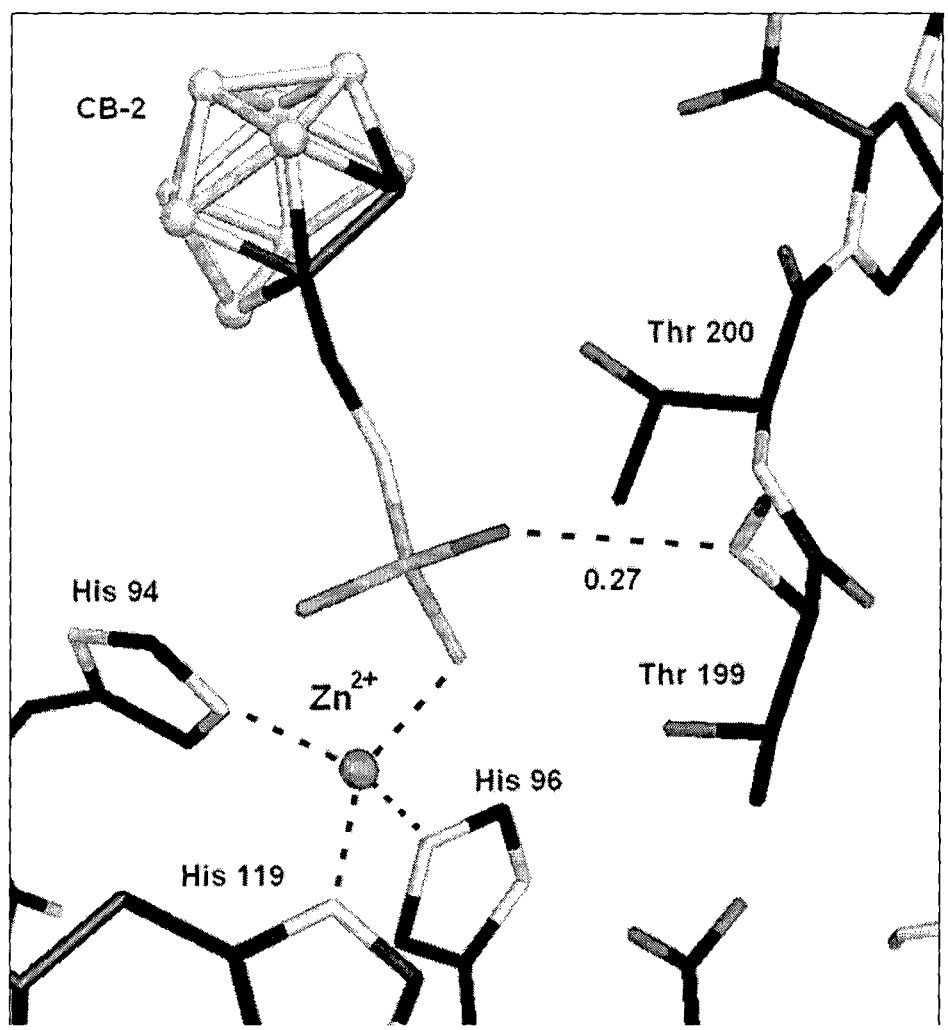

X-ray structural analysis carried out on single crystals described above showed at the resolution of 0.145 nm for the complex of HCA II+CB-1 and at the resolution of 0.160 nm for the complex of HCA II+CB 2 that the molecule of the substance CB-1 and CB-2 binds tightly to the active site of HCA II and effectively blocks the activity of enzyme. Interaction CB-1 molecule in the active site of HCA II are shown in FIG. 26, the interaction of molecules CB-2 in FIG. 27 and described below.

Binding of CB-1 molecule is very complex, the strongest interaction is coordinate covalent bond of deprotonated amino group of sulphonamide moiety to the catalytic $Zn^{2+}$ cation, which is tightly bound through three histidine side chains (His 94, His 96 and His 119) of enzyme. The resulting tetrahedral coordination of catalytic $Zn^{2+}$ cation with lone electron pairs of nitrogen atoms is characteristic for sulfonamide inhibitors of carbonic anhydrase. The oxygen atom of the sulphonamide group form a hydrogen bond with a hydrogen atom bonded to the nitrogen atom of the main chain of threonine 199. This interaction is typical for binding sulfonamide groups in the binding site of HCA II. Newly formed hydrogen bond interactions bridging NH group of CB-1, which connects the sulphonamide group to carborane cage with Oγ1 side chain atom of threonine 200. In addition, to the bond strength of inhibitor binding contribute multiple dihydrogen bonds H—H (interaction of protein hydrogen atoms with a partial positive charge and hydrogen atoms bound to the boron atom with a partial negative charge (see Fanfrlik et al., Physical Chemistry Chemical Physics 9 (17), 2085-2093) as well as multiple van der Waals interactions of carborane cage with cavity of the active site (Gln 92, His 94, Phe 131, Leu 198 and Thr 200). Binding is also stabilized by entropy contribution, several water molecules bound in the active site of free enzyme in a complex pushed back into solvent.

Binding of CB-2 molecule is very similar to CB-1 interaction. The main difference in the interaction of HCA II with CB-2 is increase of strengthen of the hydrogen bonds between the hydrogen atom bonded to the nitrogen atom of the main chain of threonine 199 and the oxygen atom of the sulphonamide group at the expense of hydrogen bonds of bridging NH group, which connects with a sulphonamide group carborane cage with Oγ1 atom at the side chain of threonine 200 in the case of complex HCA II+CB-1. And as the complex HCA II+CB-1, an inhibitor bond strength is enhanced by multiple dihydrogen H—H bonds and also multiple van der Waals interactions with active carbon cage recesses active site (His 64, Gln 92, His 94, Leu 198, Thr 200 and to 201). Also, in this case, the binding entropy stabilized interaction, several water molecules bound in the active site of free enzyme molecule is released upon CB-2 binding to the solvent.

Example 36

Testing of Cytotoxic Activity on Malignant Versus Non-Malignant Cell Lines

One of the parameters used as the basis for colorimetric assays is the metabolic activity of viable cells. For example, a microtiter assay which uses the tetrazolium salt MTT is now widely used to quantitate cell proliferation and cytotoxicity (Hájduch et al., Cytotechnology, 19, 1996, 243-245). For instance, this assay is used in drug screening programs and in chemosensitivity testing. Because tetrazolium salts are cleaved only by metabolically active cells, these assays exclusively detect viable cells. In the case of the MTT assay, yellow soluble tetrazolium salt is reduced to a coloured water-insoluble formazan salt. After it is solubilized, the formazan formed can easily and rapidly be quantified in a conventional ELISA plate reader at 570 nm (maximum absorbancy). The quantity of reduced formazan corresponds to the number of vital cells in the culture.

Cell Lines

All cells were purchased from the American Tissue Culture Collection (ATCC), unless otherwise indicated: the CEM line are highly chemosensitive T-lymphoblastic leukemia cells, K562 cells were derived from patient with acute myeloid leukemia with bcr-abl translocation, A549 line is lung adenocarcinoma, HCT116 is colorectal tumor cell line and its p53 gene knock-down counterpart (HCT116p53−) is a model of human cancers with p53 mutation frequently associated with poor prognosis. The daunorubicin resistant subline of CEM cells (CEM-DNR bulk) and paclitaxel resistant subline K562-tax were selected in our laboratory by the cultivation of maternal cell lines in increasing concentrations of daunorubicine or paclitaxel, respectively (Noskova et al., *Neoplasma* 49, 2002, 418). The CEM-DNR bulk cells overexpress MRP-1 protein, while K562-tax cells overexpress P-glycoprotein, both proteins belong to family of ABC transporters and are involved in primary and/or acquired multidrug resistance phenomenon (Noskova et al., *Neoplasma* 49, 2002, 418). The cells were maintained in Nunc/Corning 80 cm² plastic tissue culture flasks and cultured in cell culture medium (DMEM/RPMI 1640 with 5 g/l glucose, 2 mM glutamine, 100 U/ml penicillin, 100 µg/ml streptomycin, 10% fetal calf serum, and $NaHCO_3$).

MTT Assay

This assay was performed according to Hajduch et al., *Anti-Cancer Drugs* 10, 1997, 1007. Cell suspensions were prepared and diluted according to the particular cell type and the expected target cell density (2 500-30 000 cells/well based on cell growth characteristics). Cells were added by pipette (80 µl) into 96-well microtiter plates. Inoculates were allowed a pre-incubation period of 24 h at 37° C. and 5% $CO_2$ for stabilization. Four-fold dilutions, in 20-µl aliquots, of the intended test concentration were added to the microtiter plate wells at time zero. All test compound concentrations were examined in duplicate. Incubation of the cells with the test compounds lasted for 72 h at 37° C., in a 5% $CO_2$ atmosphere at 100% humidity. At the end of the incubation period, the cells were assayed using MTT. Aliquots (10 µl) of the MTT stock solution were pipetted into each well and incubated for a further 1-4 h. After this incubation period the formazan produced was dissolved by the addition of 100 µl/well of 10% aq SDS (pH=5.5), followed by a further incubation at 37° C. overnight. The optical density (OD) was measured at 540 nm with a Labsystem iEMS Reader MF. Tumor cell survival (TCS) was calculated using the following equation: TCS= $(OD_{drug-exposed\ well}/\text{mean } OD_{control\ wells}) \times 100\%$. The $TCS_{50}$ value, the drug concentration lethal to 50% of the tumor cells, was calculated from appropriate dose-response curves.

Example 37

Pharmacology of the Compounds

Dose Finding Study

In order to demonstrate pharmaceutical exploitation of our compounds, we have determined maximum tolerated dose (MTD) and dose limiting toxicity (DLT) of two promising carbonic anhydrase IX inhibitors (CB-4 and CB-16) after single dose administration. Both compounds were dissolved in 10% dimethylsulfoxide/water (vol/vol) at stock concentration of 10 mg/ml and applied intraperitoneally to NMRI female mice (minimum 3/group) in ascending doses until the MTD was reached. Animals were housed in specific pathogen free conditions, water and food ad libitum. Treated mice were observed clinically every hour in the first 8 hours, then every 12 hours until potential side effects resolved. Finally, the MTD was estimated as 125 mg/kg for CB-4 and 166 mg/kg for CB-16, respectively. The dose limiting toxicity was similar for both of these compounds and included somnolence, apathy and local irritation. Overall, the MTD achieved and MDT observed support for further pharmaceutical use of the carbonic anhydrase IX inhibitors.

Orientational Pharmacokinetics

The ability of compounds to achieve therapeutically relevant concentrations in biological fluids was tested in orientational pharmacokinetics experiment. The compounds CB-4 and CB-6 were administered intraperitoneally to female NMRI mice at the MTD (125 and 166 mg/kg respectively).

TABLE 2

$IC_{50}$ values for individual compounds determined for nine types of (non)-malignant cell lines.

| | IC50 [µM · l⁻¹] | | | | |
|---|---|---|---|---|---|
| Cell line | CCRF-CEM | CEM-DNR | A549 | K562 | K562-TAX |
| CB-1 | 61.8 ± 10.6 | 79.0 ± 8.9 | 94.9 ± 4.3 | 60.1 ± 3.0 | 81.5 ± 11.0 |
| CB-2 | 98.3 ± 3.8 | 96.7 ± 3.8 | 100.0 ± 0.0 | 100.0 ± 0.0 | 99.9 ± 0.2 |
| CB-3 | 100.0 ± 0.0 | 99.9 ± 0.2 | 100.0 ± 0.0 | 100.0 ± 0.0 | 100.0 ± 0.0 |
| CB-4 | 61.7 ± 17.8 | 74.5 ± 2.8 | 95.5 ± 3.7 | 74.3 ± 3.7 | 55.2 ± 4.7 |
| CB-5 | 85.4 ± 22.6 | 99.8 ± 0.4 | 100.0 ± 0.0 | 98.6 ± 2.2 | 66.4 ± 8.0 |
| CB-6 | 20.2 ± 1.7 | 98.1 ± 3.0 | 77.8 ± 10.8 | 27.5 ± 7.1 | 56.9 ± 15.1 |
| CB-8 | 73.4 ± 6.8 | 96.8 ± 3.3 | 96.0 ± 6.2 | 71.3 ± 4.2 | 79.6 ± 10.9 |
| CB-10 | 79.5 ± 22.7 | 100.0 ± 0.0 | 100.0 ± 0.0 | 99.6 ± 1.1 | 73.6 ± 11.1 |
| CB-12 | 100.0 ± 0.0 | 100.0 ± 0.0 | 100.0 ± 0.0 | 100.0 ± 0.0 | 100.0 ± 0.0 |
| CB-13 | 62.0 ± 3.0 | 68.0 ± 1.6 | 86.5 ± 4.6 | 71.8 ± 1.4 | 64.2 ± 4.5 |
| CB-15 | 17.3 ± 1.2 | 47.9 ± 7.6 | 33.7 ± 7.7 | 17.7 ± 0.7 | 16.6 ± 1.2 |
| CB-16 | 89.9 ± 6.0 | 95.1 ± 7.9 | 100.0 ± 0.0 | 98.6 ± 2.1 | 95.8 ± 4.4 |
| CB-17 | 95.1 ± 5.0 | 100.0 ± 0.0 | 100.0 ± 0.0 | 100.0 ± 0.0 | 100.0 ± 0.0 |
| CB-19 | 71.9 ± 3.7 | 100.0 ± 0.1 | 100.0 ± 0.0 | 81.0 ± 3.3 | 86.7 ± 12.7 |
| CB-20 | 84.5 ± 5.3 | 99.6 ± 1.1 | 100.0 ± 0.0 | 98.8 ± 2.9 | 96.3 ± 5.8 |

| | IC50 [µM · l⁻¹] | | | |
|---|---|---|---|---|
| Cell line | HCT116 | HCT116p53−/− | BJ | MRC-5 |
| CB-1 | 63.9 ± 5.7 | 62.0 ± 2.7 | 100.0 ± 0.0 | 22.1 ± 1.1 |
| CB-2 | 100.0 ± 0.0 | 99.9 ± 0.3 | 100.0 ± 0.0 | 100.0 ± 0.0 |
| CB-3 | 100.0 ± 0.0 | 100.0 ± 0.0 | 100.0 ± 0.0 | 100.0 ± 0.0 |
| CB-4 | 69.2 ± 3.0 | 71.9 ± 3.4 | 76.4 ± 3.3 | 77.9 ± 1.0 |
| CB-5 | 75.3 ± 4.1 | 64.7 ± 9.1 | 100.0 ± 0.0 | 93.2 ± 7.0 |
| CB-6 | 78.4 ± 17.0 | 24.2 ± 3.2 | 100.0 ± 0.0 | 99.7 ± 0.7 |
| CB-8 | 97.4 ± 3.4 | 86.6 ± 7.5 | 100.0 ± 0.0 | 100.0 ± 0.0 |
| CB-10 | 96.4 ± 4.5 | 99.6 ± 0.9 | 100.0 ± 0.0 | 100.0 ± 0.0 |
| CB-12 | 100.0 ± 0.0 | 100.0 ± 0.0 | 100.0 ± 0.0 | 100.0 ± 0.0 |
| CB-13 | 55.5 ± 1.8 | 61.3 ± 4.9 | 88.4 ± 6.1 | 75.6 ± 1.5 |
| CB-15 | 16.6 ± 0.2 | 17.6 ± 0.9 | 65.2 ± 4.4 | 27.0 ± 4.8 |
| CB-16 | 84.8 ± 3.0 | 78.4 ± 3.9 | 100.0 ± 0.0 | 100.0 ± 0.0 |
| CB-17 | 100.0 ± 0.0 | 100.0 ± 0.0 | 100.0 ± 0.0 | 100.0 ± 0.0 |
| CB-19 | 89.3 ± 3.3 | 78.3 ± 6.5 | 100.0 ± 0.0 | 100.0 ± 0.0 |
| CB-20 | 99.6 ± 1.1 | 100.0 ± 0.0 | 100.0 ± 0.0 | 100.0 ± 0.0 |

Consistently with the proposed mechanism of action (carbonic anhydrase IX inhibition), there was only moderate cytotoxic activity observed in tumor cells regardless histogenetic origin, genetic and drug resistance characteristics. However, the compounds were consistently less cytotoxic in non-malignant fibroblast cell lines BJ and MRC-5, thus demonstrating favorable in vitro toxicology profile.

Animals were sacrificed in anesthesia by bleeding from brachial plexus after 0.5, 1, 3, 6, 9, 12, 24 and 36 hours (3 mice per group). The blood was collected on ice and processed for serum separation within 60 minutes after sampling. Serum was evaporated to dryness on a device ThermoScientific SPD SpeedVac (72 h, 50° C.) until analyzed. Residues were precipitated by the 225 µl of acetonitrile with an addition of 25 µl of 10% SDS (w/w in water), then vortexed for 5 min and centrifuged 5 min at 14000 RPM at a room temperature. Aliquot of the supernatant was transferred into a 250 µl autosampler vial. The CB-4 or CB-16 concentrations in serum were determined by the HPLC chromatograph Merck-Hitachi system LaChrom 7000 equipped with Diode Array 7450 detector (DAD) and an Intelligent Injector L7250 on the column Merck LichroCART® Purospher® STAR RP-8e, 250×2 mm, 5 µm particle size. HPLC conditions: a mobile phase contains 6.25 mmol/l hexylamine acetate (adjusted to pH 6.25) in 72% aqueous acetonitrile. Detection DAD (220-600 nm) fixed wavelengths 312, 315, 318 and 286 nm. Sensitivity range 0.2 or 0.02 A.U.F.S. (Absorbance Units Full Scale). An Ion-pair reverse phase chromatographic method with an isocratic elution 300 µl/min was used. Sample injection: 20 µl. The FIG. 28 shows individual mouse and average serum concentrations of compounds 0.5-36 hours after administration. Data suggest that both CB-4/CB-16 showed under in vivo conditions linear pharmacokinetics with serum concentrations overcoming 120-12× carbonic anhydrase IX in vitro $IC_{50}$ (calculated from the $c_{max}$ values) with $T_{1/2}$ being 6.5-5 hours, thus suggesting significant potential for their pharmacological use.

Example 38

The Effect of CAIX Inhibitors on Intracellular pH (pHi) in Tumor Cells (Non)Expressing CA IX The effect of carborane CAIX (carbonic anhydrase IX) inhibitors was evaluated on colorectal cancer cell line HCT116 expressing CAIX enzyme versus CA IX negative cell line of T-lymphoblastic leukemia CCRF-CEM. Acetazolamide, a known inhibitor of CAIX, was used as a standard. HCT116/CCRF-CEM cells were cultivated in McCoy/RPMI Media supplemented with 10% FCS and antibiotics and seeded at high density (1.5$^6$ cells per 3.5 cm dish) to induce pericellular hypoxia and thus stimulate CA IX expression. Measurement of pHi was assessed as described in Cianchi et al. [Cianchi F., et al. Selective inhibition of carbonic anhydrase IX decreases cell proliferation and induces aramide-mediated apoptosis in human cancer cells. The Journal of Pharmacology and Experimental Therapeutics, 2010, Vol. 334, No. 3, 710-719].

In brief, the cells were treated by carboranes/acetazolamide for 24 hours at 150 µM sub-cytotoxic concentration. The pHi was measured by flow cytometry in cell cultures pretreated with 10 µM of pH sensitive probe carboxyseminaphtorhoda-fluor-1-acetoxymethyl ester (SNARF, Invitrogen, CA) for 15 min at 37° C. After incubation, the cells were washed twice with PBS. Because the addition of bicarbonate can affect pHi, all incubation and cell washes were performed in bicarbonate-free buffer. SNARF was excited at 488 nm and emitted at 580 and 640 nm. The ratio of the emission wavelengths at 640/580 nm was then used to estimate the pHi from a calibration curve. The calibration curve was prepared by nigericin clamp technique. In this method, after the SNARF labeling of untreated cells, aliquots of cell suspensions were re-suspended in a high potassium containing buffer at specific pH (usually 6.8, 7.0, 7.2, 7.4, 7.6 and 7.8). The cell suspensions were then clamped at a specific pH value by the addition of 0.03 µM nigericin (Sigma-Aldrich). Nigericin is a ionophore that allows the exchange of H for K ions, thus abolishing the pH gradient across the cell membrane. When the internal and external K concentrations are approximately equal, the pH rapidly equilibrates to the pH of the bathing solution. A total of 20,000 events were acquired on a FACS ARIA II flow cytometer (Becton. Dickinson) for further analysis.

The fluorescent ratio values (640/580 nm) calculated for each pH point were further used to construct calibration curve in Prism software (GraphPad Software, Inc., San Diego, Calif.), from which the pHi values in treated cells were determined (Table 3).

Our data suggest that the control CAIX inhibitor acetazolamide induced mild intracellular acidification, while several carborane derivatives (CB-6, CB-8, CB-15) were better than acetazolamide at 50× lower concentrations (50 versus 1 µM). However, the compounds were not active in CCRF-CEM cells with no expression the CAIX, this demonstrating the specificity of the inhibition. Interestingly, there was no straight correlation in between enzymatic and cellular CAIX assays (see Example 26), suggesting complex pharmacology, most probably involving stability, protein binding and metabolism of the compounds exposed to living cells/organisms.

TABLE 3

Flow cytometric measurement of pHi. Effects of 50 µM acetazolamide and individual carboranes at 1 µM on HCT116 cells following 24 hour incubation. Bold values indicate the compounds with higher inhibitory activity than acetazolamide in HCT116 cells.

| Compound | pHi | |
|---|---|---|
| | HCT116 | CCRF-CEM |
| control | 7.516 | 7.362 |
| acetazolamide | 7.47 | 7.34 |
| CB-1 | 7.561 | 7.429 |
| CB-2 | 7.572 | 7.308 |
| CB-3 | 7.479 | 7.362 |
| CB-4 | 7.538 | 7.385 |
| CB-5 | 7.483 | 7.378 |
| CB-6 | 7.192 | 7.352 |
| CB-8 | 7.112 | 7.427 |
| CB-10 | 7.688 | 7.328 |
| CB-12 | 7.704 | 7.395 |
| CB-13 | 7.51 | 7.452 |
| CB-15 | 7.343 | 7.472 |
| CB-16 | 7.563 | 7.442 |
| CB-17 | 7.571 | 7.412 |
| CB-19 | 7.542 | 7.319 |
| CB-20 | 7.561 | 7.422 |

INDUSTRIAL APPLICABILITY

The invention can be used in pharmaceutical industry and in medicine for treatment of tumor diseases.

The invention claimed is:
1. A compound of general formula I

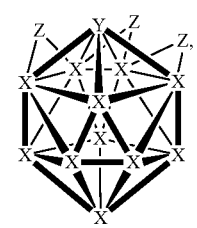

(I)

wherein
- substituent X can be selected independently from a group comprising BH, CH, $BR^1$ and $CR^1$, whereas concurrently at most four X can be CH or $CR^1$ and whereas at least one group $BR^1$ or $CR^1$ is present;
- $R^1$ in at least one substituent X is selected from a group comprising $A-NHSO_2NH_2$, $A-SO_2NH_2$ and $A-O-SO_2NH_2$, and
- $R^1$ in other substituents X can be selected independently from a group comprising $A-NHSO_2NH_2$, $A-SO_2NH_2$, $A-O-SO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing a heteroatom O, S or N, $C_1-C_8$ alkoxy, $C_1-C_8$ alkylhydroxy, $C_1-C_8$ alkylmercapto, OH, $NH_2$, $NH_3^+$, $C_1-C_8$ alkylammonium, $C_1-C_8$ alkylamino, halogen;
- A is selected from a group comprising a single bond or bivalent linear $C_1-C_{10}$ hydrocarbon chain, wherein at least one carbon atom can optionally be replaced by heteroatoms selected from a group comprising N, S, O, or by $C_4-C10$ heteroarylene, wherein the heteroatom is selected from O, N and S;

Y is $MR^2$, or Y is not present;
M is a metal of VIB or VIIIB group of periodic table;
$R^2$ is selected from a group comprising
a structure of general formula II

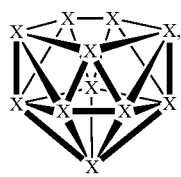

(II)

wherein X is as defined above whereas concurrently at most three X can be CH or $CR^1$; $R^1$ is selected independently from a group comprising $A-O-SO_2NH_2$, $A-SO_2NH_2$, $A-NHSO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing O, S or N as heteroatom, $C_1-C_8$ alkoxy, $C_1-C_8$ alkylhydroxy, $C_1-C_8$ alkylmercapto, OH, $NH_2$, $NH_3^+$, $C_1-C_8$ alkylammonium, $C_1-C_8$ alkylamino, halogen,
and A is as described above,
$\eta^5$-bonded cyclopentadienyl, optionally substituted by 1 to 5 methyls, and
$\eta^6$-bonded phenyl ring, optionally bearing from 1 to 6 C1-C6 alkyl groups;
Z is H or is not present; whereas from one to three Z are H only when Y is not present;
wherein
alkyl denotes a linear or branched $C_1-C_8$ hydrocarbon moiety not comprising multiple bonds, which can optionally be substituted by one or more substituents selected from a group comprising OH, halogen, $NH_2$, COOH, $CONH_2$, CN, $NO_2$, SH;
alkenyl denotes a linear or branched $C_2-C_8$ hydrocarbon chain, comprising at least one double bond, which can optionally be substituted by one or more substituents selected from a group comprising OH, halogen, $NH_2$, COOH, $CONH_2$, CN, $NO_2$, SH, $SO_3H$;
alkynyl denotes a linear or branched $C_2-C_8$ hydrocarbon chain, comprising at least one triple bond and optionally also at least one double bond, which can be optionally substituted by one or more substituents selected from a group comprising OH, halogen, $NH_2$, COOH, $CONH_2$, CN, $NO_2$, SH, $SO_3H$;
aryl denotes a $C_6-C_{10}$ aromatic carbocyclic group, comprising at least one aromatic ring or condensed aromatic rings, which can be optionally substituted by one or more substituents selected from a group comprising OH, halogen, $NH_2$, COOH, $CONH_2$, CN, $NO_2$, SH, $SO_3H$;
heteroaryl denotes a $C_4-C_{10}$ aromatic carbocyclic group, comprising at least one aromatic ring or condensed aromatic rings, in which at least one carbon atom is replaced by a heteroatom selected from a group comprising N, S, O, which can be optionally substituted by one or more substituents selected from a group comprising OH, halogen, $NH_2$, COOH, $CONH_2$, CN, $NO_2$, SH, $SO_3H$;
alkoxyl denotes a monovalent group derived from $C_1-C_8$ alcohol by the separation of a hydrogen atom from hydroxygroup;
alkylamino is a group, created by a substitution of one or two hydrogen atoms of aminogroup by $C_1-C_8$ alkyl;
alkylmercapto is a monovalent group derived from $C_1-C_8$ thiol by the cleavage of a hydrogen atom from SH group;
halogen is fluorine, chlorine, bromine or iodine atom;
bivalent linear $C_1-C_{10}$ hydrocarbon chain refers to a chain containing single bonds, optionally also double bonds, which binds oneself by terminal carbons;
and their pharmaceutically acceptable salts and solvates.

2. A compound according to claim 1 of formulae $[7-CB_{10}H_{13}]^-$, $[7,8-C_2B_9H_{12}]^-$, $[7,9-C_2B_9H_{12}]^-$, $[7,8,9-C_3B_8H_{11}]^-$, $[7,8,10-C_3B_8H_{11}]^-$, wherein one hydrogen atom is replaced by selected from the group comprising $A-SO_2NH_2$, $A-O-SO_2NH_2$, $A-NHSO_2NH_2$ and further at most three hydrogen atoms can be replaced by $R^1$ selected independently from a group comprising $A-SO_2NH_2$, $A-O-SO_2NH_2$, $A-NHSO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing heteroatom O, S or N, $C_1-C_8$ alkoxy, $C_1-C_8$ alkylmercapto, $C_1-C_8$ alkylhydroxy, OH, $NH_2$, $NH_3^+$, $C_1-C_8$ alkylamino, $C_1-C_8$ alkylammonium, halogen.

3. A compound according to claim 1 of formula $[C_2B_9H_{10}R^1Y]$ or $[C_3B_8H_{10}R^1Y]$, wherein substituent $R^1$ is selected from the group comprising $A-SO_2NH_2$, $A-O-SO_2NH_2$, $A-NHSO_2NH_2$, and Y is $MR^2$, whereas M is Co and $R^2$ is $[7,8-C_2B_9H_{11}]^{2-}$, $[7,9-C_2B_9H_{11}]^{2-}$, $[7,8-C_2B_9H_{10}R^1]^{2-}$ or $[7,9-C_2B_9H_{10}R^1]^{2-}$, wherein the substituent $R^1$ is selected independently from a group comprising $A-SO_2NH_2$, $A-O-SO_2NH_2$, $A-NHSO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing heteroatom O, S or N, $C_1-C_8$ alkoxy, $C_1-C_8$ alkylmercapto, $C_1-C_8$ alkylhydroxy, OH, $NH_2$, $NH_3^+$, $C_1-C_8$ alkylamino, $C_1-C_8$ alkylammonium, halogen.

4. A compound according to claim 1 of formula $[C_3B_8H_{10}R^1Y]$, wherein substituent $R^1$ is selected from the group comprising $A-SO_2NH_2$, $A-O-SO_2NH_2$, $A-NHSO_2NH_2$, and Y is $MR^2$, whereas M is Fe and $R^2$ is $[C_3B_8H_{10}R^1]^-$ or $[C_3B_8H_{11}]^-$, wherein the substituent $R^1$ is selected independently from a group comprising $A-SO_2NH_2$, $A-O-SO_2NH_2$, $A-NHSO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing heteroatom O, S or N, $C_1-C_8$ alkoxy, $C_1-C_8$ alkylmercapto, $C_1-C_8$ alkylhydroxy, OH, $NH_2$, $NH_3^+$, $C_1-C_8$ alkylamino, $C_1-C_8$ alkylammonium, halogen.

5. A compound according to claim 1 of formula $[C_3B_8H_{10}R^1Y]$, wherein substituent $R^1$ is selected from the group comprising $A-SO_2NH_2$, $A-O-SO_2NH_2$, $A-NHSO_2NH_2$, and Y is $MR^2$, whereas A has the meaning described above, M is Fe and $R^2$ is $\eta^5$-bonded cyklopentadienyl, optionally substituted by 1 to 5 methyls.

6. A compound according to claim 1, wherein $R^1$ consists of group A-NHSO$_2$NH$_2$ for at least one X and $R^1$ for another one or more X can be selected independently from a group comprising A-SO$_2$NH$_2$ or A-O—SO$_2$NH$_2$, A-NHSO$_2$NH$_2$, phenyl and $C_1$-$C_4$ alkoxy, whereas A is a bond or bivalent linear $C_1$-$C_6$ hydrocarbon chain, in which optionally from 1 to 2 carbon atoms are replaced by oxygen atoms.

7. A compound of general formula I according to claim 1, wherein $R^1$ consists of group A-SO$_2$NH$_2$ or A-O—SO$_2$NH$_2$ for at least one X and $R^1$ for another one or more X can be selected independently from a group comprising A-SO$_2$NH$_2$ or A-O—SO$_2$NH$_2$, A-NHSO$_2$NH$_2$, phenyl and $C_1$-$C_4$ alkoxy, whereas A is a bond or bivalent linear $C_1$-$C_6$ hydrocarbon chain, in which optionally from 1 to 2 carbon atoms are replaced by oxygen atoms.

8. A medicament comprising a compound according to claim 1 and at least one excipient.

9. A method of at least one of treating and diagnosing a condition, the condition being at least one of cancer, a proliferative disease, and a hypoxic disease, the method comprising administering at least one compound according to claim 1 to a subject.

10. A method of producing a medicament, the method comprising combining one or more compounds according to claim 1 and one or more excipients.

11. Method of preparation of a compound of general formula I described in claim 1, characterized in that compounds of formula III

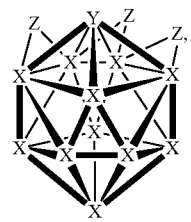

(III)

wherein

X is independently selected from a group comprising BH, CH, BR$^3$ and CR$^3$, whereas concurrently at most four X can be CH or CR$^3$ and at least one group BR$^3$ or CR$^3$ is present;

$R^3$ consists of group A-NH$_2$ or A-NH$_3^+$ at least for one X and further substituents $R^3$ can be selected independently from a group comprising A-NH$_2$ or A-NH$_3^+$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing a heteroatom O, S or N, $C_1$-$C_8$ alkoxy, $C_1$-$C_8$ alkylhydroxy, $C_1$-$C_8$ alkylmercapto, OH, NH$_2$, NH$_3^+$, $C_1$-$C_8$ alkylammonium, $C_1$-$C_8$ alkylamino, halogen;

A is selected from a group comprising a bond or linear $C_1$-$C_{10}$ hydrocarbon chain, wherein some carbon atoms can be replaced by heteroatoms chosen from a group comprising N, S, O, or $C_4$-$C_{10}$ heteroarylene, wherein a heteroatom is chosen from O, N or S;

Y is MR$^3$, or Y is not present;

M is a metal of VIB or VIIIB group of periodic table;

$R^2$ is selected from a group comprising a structure of general formula II

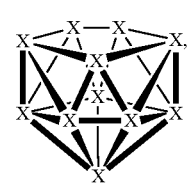

(II)

wherein X is as defined above, whereas at most three X can be concurrently CH or CR$^1$; $R^1$ is selected independently from a group comprising A-O—SO$_2$NH$_2$, A-SO$_2$NH$_2$, A-NHSO$_2$NH$_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing O, S or N as heteroatom, $C_1$-$C_8$ alkoxy, $C_1$-$C_8$ alkylhydroxy, $C_1$-$C_8$ alkylmercapto, OH, NH$_2$, NH$_3^+$, $C_1$-$C_8$ alkylammonium, $C_1$-$C_8$ alkylamino, halogen, wherein A is as described above, $\eta^5$-bonded cyklopentadienyl, optionally substituted by 1 to 5 methyls and $\eta^6$-bonded phenyl ring, optionally bearing from 1 to 6 $C_1$-$C_6$ alkyl groups;

Z is H or is not present; whereas from one to three Z are H only when Y is not present, are treated by a sulfamide of formula H$_2$NSO$_2$NH$_2$.

12. Method of preparation according to claim 11, characterized in that the reaction is carried out in an organic solvent, whereas the aminogroup is replaced by sulfamide group.

13. Method of preparation according to claim 12, characterized in that the organic solvent is selected from a group comprising dioxane, dimethylformamide, dimethylether and dimethylether of diethylenglycol.

14. Method of preparation of a compound [8,8'-μ-(CH$_2$O (CH$_3$))-(1,2-C$_2$B$_9$H$_{10}$)$_2$-3-Co] as an intermediate for a preparation of compounds of general formula I described in claim 1, characterized in that a suspension of cobalt-bis(dicarbollide) salt in organic solvent is treated by para-formaldehyde or formaldehyde in presence of strong anorganic acid and the product is isolated or used in mixture with other electroneutral products of the reaction directly for a production of compounds of general formula I.

15. Method of preparation of a compound of general formula I described in claim 1, characterized in that compounds of formula [(HO—(CH$_2$)$_n$)$_m$(C$_2$B$_9$H$_{11-p}$)$_2$Co]$^-$ where n=1-3, m=1 or 2, p=0 or 1 deprotoned by Cs$_2$CO$_3$, sodium hydride or potassium tert-butoxide, are treated by sulfamoyl chlorid of general formula Cl—SO$_2$NH$_2$ in organic solvent selected from dioxane, dimethylformamide, tetrahydrofurane, dialkylether of ethylenglycol and dialkylether of diethylenglycol, or in mixture of organic solvent with toluene, xylene, cymene or cumene, where terminal oxygen atoms are substituted by sulfamoyl group.

16. Method of preparation of compounds of general formula I described in claim 1 characterized in that the compound of formula [8,8'-μ-(CH$_2$O(CH$_3$))-(1,2-C$_2$B$_9$H$_{10}$)$_2$-3-Co], bearing biatomic bridge substituent {—O$^+$ (CH$_3$)—CH$_2$-} between two atoms of boron in metallacarborane, or compounds substituted by dioxane or tetrahydropyrane ring, being [(8-O(CH$_2$CH$_2$)$_2$O)-(1,2-C$_2$B$_9$H$_{10}$)(1',2'-C$_2$B$_9$H$_{11}$)-3,3'-Co] or [(8-(CH$_2$)$_5$O-(1,2-C$_2$B$_9$H$_{10}$)(1',2'-C$_2$B$_9$H$_{11}$)-3,3'-Co], comprising also a reactive oxonium atom, are treated by sulfamide in an organic solvent or in a mixture of an organic solvent with toluene, xylene, cymene or cumene, in the process an opening of the ring occurs as well as a terminal position substitution by a sulfamide group.

17. Method of preparation of compounds of general formula I described in claim 1 characterized in that the icosaedric carborane $1,2-C_2B_{10}H_{12}$ having carbon atoms in vicinal position, from which at least one is substituted by amino group, is treated by a sulfamide in an organic solvent where Y being BH is splited off and concurrently a terminal amino group is substituted by sulfamide group and boron atom is substituted by a bridge group Z where Z is H.

18. Method of preparation of C-aminoderivatives of formula $[(H_2N—(CH_2)_n—C_2B_9H_{10})(C_2B_9H_{11})Co]$ as precursors of compounds of general formula I described in claim 1, characterized in that an anhydric salt of icosaedric metallacarborane $[(C_2B_9H_{11})_2Co]$ is treated by $R^3Li$, where $R^3$ is selected from methyl, butyl, phenyl and tert-butyl, in dimethylether or diethylether of ethylenglycol and then by bromo- or iodo-alkylamine with protected amino group, where the protecting group is phtalimide, bis(trimetyl silyl) or t-Bu-carbonyl, the products are isolated and then the protecting group is cleaved using ethylenediamine or by action of reduction agent, acid or alkaline reagent.

19. Method of preparation of C-aminoderivatives of formula $[(H_3N—(CH_2)_n)_m(C_2B_9H_{11-p})Co]$, where n is n=1 to 3, m=1 or 2, p=0 or 1, as precursors of compounds of general formula I described in claim 1, characterized in that C-hydroxyalkyl derivatives of icosahedral cobaltacarborane $[(HO—(CH_2)_n)_m(C_2B_9H_{11-p})_2—Co]^-$, where n is n=1 to 3, m=1 or 2, p=0 or 1, in the form of trimethyl ammonium salts or cesium salts, are treated in presence of trimethylamine hydrochloride by toluene sulfonyl chloride or by trifluoromethyl sulfonyl chloride or by trifluoromethyl sulfonyl anhydride in acetonotrile, tetrahydrofurane or diethylether of ethyleneglycol in presence of carbonate of alkali metal; the resulting esters are isolated by recrystalization or by dissolution of product in aqueous methanol or ethanol, then precipitation of the tetramethyl ammonium salts and drying under vacuum and thus obtained salts are heated in acetonitrile, tetrahydrofurane or dioxane with excess of ammonia and finally isolated using a crystallization, precipitation in form of low soluble salts such as $R_4N^+$, where R is $C_1$ to $C_4$ alkane, and recrystallization or by liquid chromatography.

20. Method of preparation of C-aminoderivative of formula $7-H_2N—(CH_2)—C_2B_9H_{10}$ as precursor of compounds of general formula I described in claim 1, characterized in that icosahedric carborane of formula $1-Br—CH_2-1,2-C_2B_{10}H_{11}$ is treated by aqueous ammonia in ethanol or by aqueous ammonia in toluene and the product is then isolated.

21. A method of at least one of treating and diagnosing a condition, the condition being a tumor disease characterized by hyperexpresion of carbonic anhydrase IX, the method comprising administering at least one compound according to claim 1 to a subject.

22. A method of at least one of treating and diagnosing a condition, the condition being selected from colorectal, lung, breast, prostate, cervical, ovary, oesophageal, or brain cancers, the method comprising administering at least one compound according to claim 1 to a subject.

23. A compound according to claim 1, wherein no more than three X can concurrently be CH or $CR^1$.

24. A method of at least one of treating and diagnosing a condition, the condition being at least one of cancer, a proliferative disease, and a hypoxic disease, the method comprising administering at least one compound according to general formula I to a subject;

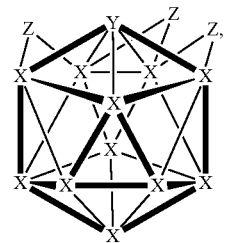

(I)

wherein:
substituent X can be selected independently from a group comprising BH, CH, $BR^1$ and $CR^1$, whereas concurrently at most four X can be CH or $CR^1$ and whereas at least one group $BR^1$ or $CR^1$ is present;
$R^1$ in at least one substituent X is selected from a group comprising $A-NHSO_2NH_2$, $A-SO_2NH_2$ and $A-O—SO_2NH_2$, and
$R^1$ in other substituents X can be selected independently from a group comprising $A-NHSO_2NH_2$, $A-SO_2NH_2$, $A-O—SO_2NH_2$, $C_1-C_8$ alkyl, $C_2-C_8$ alkenyl, $C_6-C_{10}$ aryl, $C_2-C_8$ alkynyl, $C4-C_{10}$ heteroaryl containing a heteroatom O, S or N, $C_1-C_8$ alkoxy, $C_1-C_8$ alkylhydroxy, $C_1-C_8$ alkylmercapto, OH, $NH_2$, $NH_3^+$, $C_1-C_8$ alkylammonium, $C_1-C_8$ alkylamino, halogen;
A is selected from a group comprising a single bond or bivalent linear $C_1-C_{10}$ hydrocarbon chain, wherein at least one carbon atom can optionally be replaced by heteroatoms selected from a group comprising N, S, O, or by a group selected from $C_6-C_{10}$ arylene and $C_4-C_{10}$ heteroarylene, wherein the heteroatom is selected from O, N and S;
Y is selected from a group comprising BH, CH, $BR^1$, $CR^1$, $MR^2$, or Y is not present;
M is a metal of VIB or VIIIB group of periodic table;
$R^2$ is selected from a group comprising
a structure of general formula II

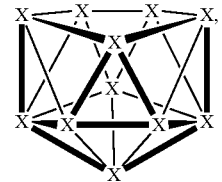

(II)

wherein X is as defined above whereas concurrently at most three X can be CH or $CR^1$; $R^1$ is selected independently from a group comprising $A-O—SO_2NH_2$, $A-SO_2NH_2$, $A-NHSO_2NH_2$, $C_1-C_8$ alkyl, $C_2-C_8$ alkenyl, $C_6-C_{10}$ aryl, $C_2-C_8$ alkynyl, $C_4-C_{10}$ heteroaryl containing O, S or N as heteroatom, $C_1-C_8$ alkoxy, $C_1-C_8$ alkylhydroxy, $C_1-C_8$ alkylmercapto, OH, $NH_2$, $NH_3^+$, $C_1-C_8$ alkylammonium, $C_1-C_8$ alkylamino, halogen,
and A is as described above,
$\eta^5$-bonded cyclopentadienyl, optionally substituted by 1 to 5 methyls, and
$\eta^6$-bonded phenyl ring, optionally bearing from 1 to 6 $C_1-C_6$ alkyl groups;
Z is H or is not present; whereas from one to three Z are H only when Y is not present;

wherein
alkyl denotes a linear or branched $C_1$-$C_8$ hydrocarbon moiety not comprising multiple bonds, which can optionally be substituted by one or more substituents selected from a group comprising OH, halogen, $NH_2$, COOH, $CONH_2$, CN, $NO_2$, SH;
alkenyl denotes a linear or branched $C_2$-$C_8$ hydrocarbon chain, comprising at least one double bond, which can optionally be substituted by one or more substituents selected from a group comprising OH, halogen, $NH_2$, COOH, $CONH_2$, CN, $NO_2$, SH, $SO_3H$;
alkynyl denotes a linear or branched $C_2$-$C_8$ hydrocarbon chain, comprising at least one triple bond and optionally also at least one double bond, which can be optionally substituted by one or more substituents selected from a group comprising OH, halogen, $NH_2$, COOH, $CONH_2$, CN, $NO_2$, SH, $SO_3H$;
aryl denotes a $C_6$-$C_{10}$ aromatic carbocyclic group, comprising at least one aromatic ring or condensed aromatic rings, which can be optionally substituted by one or more substituents selected from a group comprising OH, halogen, $NH_2$, COOH, $CONH_2$, CN, $NO_2$, SH, $SO_3H$;
heteroaryl denotes a $C_4$-$C_{10}$ aromatic carbocyclic group, comprising at least one aromatic ring or condensed aromatic rings, in which at least one carbon atom is replaced by a heteroatom selected from a group comprising N, S, O, which can be optionally substituted by one or more substituents selected from a group comprising OH, halogen, $NH_2$, COOH, $CONH_2$, CN, $NO_2$, SH, $SO_3H$;
alkoxyl denotes a monovalent group derived from $C_1$-$C_8$ alcohol by the separation of a hydrogen atom from hydroxygroup;
alkylamino is a group, created by a substitution of one or two hydrogen atoms of aminogroup by $C_1$-$C_8$ alkyl;
alkylmercapto is a monovalent group derived from $C_1$-$C_8$ thiol by the cleavage of a hydrogen atom from SH group;
halogen is fluorine, chlorine, bromine or iodine atom;
bivalent linear $C_1$-$C_{10}$ hydrocarbon chain refers to a chain containing single bonds, optionally also double bonds, which binds oneself by terminal carbons;
and their pharmaceutically acceptable salts and solvates.

25. A method of producing a medicament, the method comprising combining one or more compounds according to general formula I and one or more excipients;

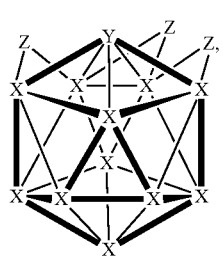

(I)

wherein
substituent X can be selected independently from a group comprising BH, CH, $BR^1$ and $CR^1$, whereas concurrently at most four X can be CH or $CR^1$ and whereas at least one group $BR^1$ or $CR^1$ is present;
$R^1$ in at least one substituent X is selected from a group comprising A-$NHSO_2NH_2$, A-$SO_2NH_2$ and A-O—$SO_2NH_2$, and $R^1$ in other substituents X can be selected independently from a group comprising A-$NHSO_2NH_2$, A-$SO_2NH_2$, A-O—$SO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing a heteroatom O, S or N, $C_1$-$C_8$ alkoxy, $C_1$-$C_8$ alkylhydroxy, $C_1$-$C_8$ alkylmercapto, OH, $NH_2$, $NH_3^+$, $C_1$-$C_8$ alkylammonium, $C_1$-$C_8$ alkylamino, halogen;
A is selected from a group comprising a single bond or bivalent linear $C_1$-$C_{10}$ hydrocarbon chain, wherein at least one carbon atom can optionally be replaced by heteroatoms selected from a group comprising N, S, O, or by a group selected from $C_6$-$C_{10}$ arylene and $C_4$-$C_{10}$ heteroarylene, wherein the heteroatom is selected from O, N and S;
Y is selected from a group comprising BH, CH, $BR^1$, $CR^1$, $MR^2$, or Y is not present;
M is a metal of VIB or VIIIB group of periodic table;
$R^2$ is selected from a group comprising
a structure of general formula II

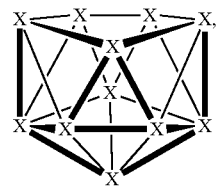

(II)

wherein X is as defined above whereas concurrently at most three X can be CH or $CR^1$; $R^1$ is selected independently from a group comprising A-O—$SO_2NH_2$, A-$SO_2NH_2$, A-$NHSO_2NH_2$, $C_1$-$C_8$ alkyl, $C_2$-$C_8$ alkenyl, $C_6$-$C_{10}$ aryl, $C_2$-$C_8$ alkynyl, $C_4$-$C_{10}$ heteroaryl containing O, S or N as heteroatom, $C_1$-$C_8$ alkoxy, $C_1$-$C_8$ alkylhydroxy, $C_1$-$C_8$ alkylmercapto, OH, $NH_2$, $NH_3^+$, $C_1$-$C_8$ alkylammonium, $C_1$-$C_8$ alkylamino, halogen,
and A is as described above,
$\eta^5$-bonded cyclopentadienyl, optionally substituted by 1 to 5 methyls, and
$\eta^6$-bonded phenyl ring, optionally bearing from 1 to 6 $C_1$-$C_6$ alkyl groups;
Z is H or is not present; whereas from one to three Z are H only when Y is not present;
wherein
alkyl denotes a linear or branched $C_1$-$C_8$ hydrocarbon moiety not comprising multiple bonds, which can optionally be substituted by one or more substituents selected from a group comprising OH, halogen, $NH_2$, COOH, $CONH_2$, CN, $NO_2$, SH;
alkenyl denotes a linear or branched $C_2$-$C_8$ hydrocarbon chain, comprising at least one double bond, which can optionally be substituted by one or more substituents selected from a group comprising OH, halogen, $NH_2$, COOH, $CONH_2$, CN, $NO_2$, SH, $SO_3H$;
alkynyl denotes a linear or branched $C_2$-$C_8$ hydrocarbon chain, comprising at least one triple bond and optionally also at least one double bond, which can be optionally substituted by one or more substituents selected from a group comprising OH, halogen, $NH_2$, COOH, $CONH_2$, CN, $NO_2$, SH, $SO_3H$;
aryl denotes a $C_6$-$C_{10}$ aromatic carbocyclic group, comprising at least one aromatic ring or condensed aromatic rings, which can be optionally substituted by one or more substituents selected from a group comprising OH, halogen, $NH_2$, COOH, $CONH_2$, CN, $NO_2$, SH, $SO_3H$;

heteroaryl denotes a $C_4$-$C_{10}$ aromatic carbocyclic group, comprising at least one aromatic ring or condensed aromatic rings, in which at least one carbon atom is replaced by a heteroatom selected from a group comprising N, S, O, which can be optionally substituted by one or more substituents selected from a group comprising OH, halogen, $NH_2$, COOH, $CONH_2$, CN, $NO_2$, SH, $SO_3H$;

alkoxyl denotes a monovalent group derived from $C_1$-$C_8$ alcohol by the separation of a hydrogen atom from hydroxygroup;

alkylamino is a group, created by a substitution of one or two hydrogen atoms of aminogroup by $C_1$-$C_8$ alkyl;

alkylmercapto is a monovalent group derived from $C_1$-$C_8$ thiol by the cleavage of a hydrogen atom from SH group;

halogen is fluorine, chlorine, bromine or iodine atom;

bivalent linear $C_1$-$C_{10}$ hydrocarbon chain refers to a chain containing single bonds, optionally also double bonds, which binds oneself by terminal carbons;

and their pharmaceutically acceptable salts and solvates.

* * * * *